US008620595B2

(12) United States Patent
Krokhin et al.

(10) Patent No.: US 8,620,595 B2
(45) Date of Patent: Dec. 31, 2013

(54) METHODS FOR DETERMINING THE RETENTION OF PEPTIDES IN REVERSE PHASE CHROMATOGRAPHY USING LINEAR SOLVENT STRENGTH THEORY

(75) Inventors: Oleg V. Krokhin, Winnipeg (CA); Vic Spicer, Winnipeg (CA)

(73) Assignee: University of Manitoba, Winnipeg, MB (CA)

( * ) Notice: Subject to any disclaimer, the term of this patent is extended or adjusted under 35 U.S.C. 154(b) by 200 days.

(21) Appl. No.: 13/072,877

(22) Filed: Mar. 28, 2011

(65) Prior Publication Data

US 2011/0245461 A1 Oct. 6, 2011

Related U.S. Application Data

(60) Provisional application No. 61/318,037, filed on Mar. 26, 2010.

(51) Int. Cl.
*G01N 31/00* (2006.01)
(52) U.S. Cl.
USPC .......................................................... 702/23
(58) Field of Classification Search
USPC .......................................................... 702/23
See application file for complete search history.

(56) References Cited

PUBLICATIONS

Aguilar, M.I. et al. "High-Performance Liquid Chromatography of Amino Acids, Peptides and Proteins. LXV*. Studies on the Optimisation of the Reversed-Phase Gradient Elution of Polypeptides: Evaluation of Retention Relationships with β-Endorphin-Related Polypeptides." J. Chromatogr. 1985, 327, 115-138.
Dwivedi, R.C. et al. "Practical Implementation of 2D HPLC Scheme with Accurate Peptide Retention Prediction in Both Dimensions for High-Throughput Bottom-Up Proteomics." Anal Chem. 2008, 80, 7036-7042.
Gilar, M. et al. "Peptide Retention Prediction Applied to Proteomic Data Analysis." Rapid Commun Mass Spectrom. 2007, 21, 2813-2821.
Glaich J.L. et al. "Separation of Peptide Mixtures by Reversed-Phase Gradient Elution. Use of Flow Rate Changes for Controlling Band Spacing and Improving Resolution." Anal. Chem. 1986, 58, 280-285.
Gorshkov, A.V. et al. "Liquid Chromatography at Critical Conditions: Comprehensive Approach to Sequence-Dependent Retention Time Prediction." Anal Chem. 2006, 78, 7770-7777.
Guo, D. et al. "Prediction of Peptide Retention Times in Reversed-Phase High-Performance Liquid Chromatography. I. Determination of Retention Coefficients of Amino Acid Residues of Model Synthetic Peptides." J. Chromatogr. 1986, 359, 499-517.
Guo, D.C. et al. "Effects of Ion-Pairing Reagents on the Prediction of Peptide Retention in Reversed-Phase High-Performance Liquid Chromatography." J Chromatogr 1987, 386, 205-222.
Hearn, M.T.W. and Aguilar, M.I., "High-Performance Liquid Chromatography of Amino Acids, Peptides and Proteins. LXVIII*. Evaluation of Retention and Bandwidth Relationships of Peptides Related to Luteinishing Hormone-Releasing Hormone and Growth Hormone-Releasing Factor, Separated by Gradient Elution Reversed-Phase High-Performance Liquid Chromatography." J. Chromatogr. 1986, 359, 31-54.
Hearn, M.T.W. and Aguilar, M.I., "High-Performance Liquid Chromatography of Amino Acids, Peptides and Proteins. LXIX*. Evaluation of Retention and Bandwidth Relationships of Myosin-Related Peptides Separated by Gradient Elution Reversed-Phase High-Performance Liquid Chromatography." J. Chromatogr. 1987, 392, 33-49.
Houghten, R.A. and Degraw, S.T. J., "Effect of Positional Environmental Domains of the Variation of High-Performance Liquid Chromatographic Peptide Retention Coefficients." Chromatogr. 1987, 386, 223-228.
Klammer, A.A. et al. "Improving Tandem Mass Spectrum Identification Using Peptide Retention Time Prediction Across Diverse Chromatography Conditions." Anal Chem. 2007, 79, 6111-6118.
Krokhin, O.V. et al. "An Improved Model for Prediction of Retention Times of Tryptic Peptides in Ion Pair Reversed-Phase HPLC." Mol Cell Proteomics 2004, 3, 908-919.
Krokhin, O.V., "Sequence-Specific Retention Calculator. Algorithm for Peptide Retention Prediction in Ion-Pair RP-HPLC: Application to 300- and 100-Å Pore Size C18 Sorbents." Anal. Chem. 2006, 78, 7785-7795.
Krokhin, O.V. and Spicer, V., "Peptide Retention Standards and Hydrophobicity Indexes in Reversed-Phase High-Performance Liquid Chromatography of Peptides." Anal Chem 2009, 81, 9522-9530.
Lambert, J.P. et al. "Proteomics: From Gel Based to Gel Free." Anal Chem, 2005, 77, 3771-3788.
Mant, C.T. et al. "Effect of Peptide Chain Length on Peptide Retention Behaviour in Reversed-Phase Chromatography." J. Chromatogr. 1988, 458, 193-205.
Meek, J.L., "Prediction of Peptide Retention Times in High-Pressure Liquid Chromatography on the Basis of Amino Acid Composition." Proc. Natl. Acad. Sci. USA, 1980, 77, 3, 1632-1636.
Petritis, K. et al. "Improved Peptide Elution Time Prediction for Reversed-Phase Liquid Chromatography-MS by Incorporating Peptide Sequence Information." Anal Chem. 2006, 78, 5026-5039.
Sandra, K. et al. "Highly Efficient Peptide Separations in Proteomics Part 1. Unidimensional High Performance Liquid Chromatography." Chromatogr B Analyt Technol Biomed Life Sci. 2008, 866, 48-63.
Shinoda, K. et al. "Prediction of Liquid Chromatographic Retention Times of Peptides Generated by Protease Digestion of the *Escherichia coli* Proteome Using Artificial Neural Networks." Proteome Res. 2006, 5, 3312-3317.
Shinoda, K. et al. "Aligning LC Peaks by Converting Gradient Retention Times to Retention Index of Peptides in Proteomic Experiments." Bioinformatics 2008, 24, 14, 1590-1595.

(Continued)

*Primary Examiner* — Jerry Lin
(74) *Attorney, Agent, or Firm* — Bereskin & Parr LLP/S.E.N.C.R.L., s.r.l.; Noel Courage

(57) ABSTRACT

The present disclosure relates to methods for separating or isolating a peptide using reverse phase chromatography. The disclosure also relates to methods for calculating or determining the slope S of a peptide, wherein S is defined according to the Linear-Solvent-Strength equation $\log k = \log k_0 - S*\phi$. Also provided are a set of peptides with known S values suitable for use in the described methods.

11 Claims, 13 Drawing Sheets

(56) References Cited

PUBLICATIONS

Snyder, L.R. and Dolan J.W. High-Performance Gradient Elution: The Practical Application of the Linear-Solvent-Strength Model. Wiley; New York: 2006.

Spicer, V. et al. "Sequence-Specific Retention Calculator. A Family of Peptide Retention Time Prediction Algorithms in Reversed-Phase HPLC: Applicability to Various Chromatographic Conditions and Columns." Anal Chem. 2007, 79, 8762-8768.

Stadalius, M.A. et al. "Optimization Model for the Gradient Elution Separation of Peptide Mixtures by Reversed-Phase High-Performance Liquid Chromatography. Verification of Retention Relationships." J. Chromatogr. 1984, 296, 31-59.

Strittmatter, E.F. et al. "Application of Peptide LC Retention Time Information in a Discriminant Function for Peptide Identificaiton by Tandem Mass Spectrometry." J Proteome Res 2004, 3, 760-769.

Vu, H. et al. "A Model for Predicting Slopes S in the Basic Equation for the Linear-Solvent Strength Theory of Peptide Separation by Reversed-Phase High-Performance Liquid Chromatography." J Chromatogr A, 2010, 1217, 489-497.

Washburn, M.P. et al. "Large-scale analysis of the yeast proteome by multidimensional protein identification technology." Nat Biotechnol. 2001, 19, 242-247.

Optimization parameters (in BOLD):

SF1=0.41           SF2=0.75
GORF=0.04          GFEEL=0.49
HWT=2.5            HWT_SF=2.8
SHORT=4.5          DCORR=1.1            ECORR=0.8
GBASH=0.55         DEPBASH=0.05
HICUTOFF=1.25      HISCALE=1.1
GCC=0.164
DZAP=0.12          EZAP=0.02
D4=0.2             E4=0.5
D3=0.3             E3=-0.2

PLUS Si for each amino acid (in Table 2 of text)

FIG. 5 (CONT.)

METHODS FOR DETERMINING THE RETENTION OF PEPTIDES IN REVERSE PHASE CHROMATOGRAPHY USING LINEAR SOLVENT STRENGTH THEORY

CROSS REFERENCE TO RELATED APPLICATIONS

This application claims priority to U.S. Application No. 61/318,037 filed on Mar. 26, 2010, which is incorporated by reference herein in its entirety.

INCORPORATION OF SEQUENCE LISTING

A computer readable form of the Sequence Listing "9157-95_SequenceListing.txt" (62,034 bytes), submitted via EFS-WEB and created on Mar. 25, 2011, is herein incorporated by reference.

FIELD

The present disclosure relates to reversed-phase chromatography, and more specifically to methods and compositions for separating peptides using reversed-phase high performance liquid chromatography (RP-HPLC).

BACKGROUND

Despite being an important part of bottom-up proteomic protocols, RP-HPLC is still viewed as a "simple sample preparation technique" employed prior to mass spectroscopy (MS) analysis. Recent trends in the development of proteomic procedures have shown the growing utility of peptide RP retention prediction for protein identification and quantification (for example, in scheduled multiple reaction monitoring/selected reaction monitoring (MRM/SRM) protocols). A number of peptide retention prediction models have been recently developed.[8,9] However, future advances in this direction still require a better understanding of a peptide's RP LC separation mechanism. This is particularly true for "bottom-up" proteomic approaches, where separation of thousands (if not millions) of peptides is required.[1]

Reversed-phase chromatography and MS separation techniques utilize different properties of the species for fractionation. MS possesses much higher separation power and is based on the well-studied principles of "gaseous" ion chemistry. The same can't be said about peptide RP-LC: the very basic principles of separation are still unknown despite years of intensive study and application. The separation process is often viewed in a simplified form as "catch and release" of peptide species when the critical concentration of organic solvent is reached. The real picture, however, is much more complex: under gradient conditions, peptides are constantly "on the move" with different accelerations which are based on the intrinsic molecular features encoded in the slopes S in the basic equation of the linear-solvent strength (LSS) theory.[17] Separation selectivity is affected by the value of slope S in the basic LSS equation:

$$\log k = \log k_0 - S^*\phi; \quad (1)$$

where k is the retention factor at an organic solvent volume fraction $\phi$ (such as $\phi$=ACN %/100) and $k_0$ is the retention factor at $\phi$=0.

Peptides can exhibit unexpected and generally unpredictable changes in relative peptide retention when the physical parameters of a LC system (gradient slope, flow rate, column size) are altered. For example, running identical samples with a 4-times difference in gradient slope (for example, 1% and 0.25% acetonitrile per minute) will change retention time correlation from the ideal 1.00 to a ~0.99 $R^2$-value. Calculations suggest that retention time vs. retention time correlations of ~0.95 and ~0.92 will be observed for 32-x and 100-x changes in the gradient slope, respectively. Some species will even change their retention order. Such a dramatic variation in separation selectivity threatens to make the application of retention time prediction protocols, the transfer of scheduled MRM(SRM) procedures between LC systems, and inter-laboratory data collection and comparison very problematic.

Classical LSS theory suggests a direct correlation between slopes S in the basic LSS equation and the molecular weight of peptides and proteins[17]. This theory, however, doesn't work for the typical peptide mixtures that proteomics researchers are dealing with; the suggested formula $S=a(MW)^b$ gives at best an $R^2$-value correlation of ~0.3. Dealing with real tryptic peptides introduces significant variability in peptide structures, which strongly affects the accuracy of predictions made using this model.

In chromatography, retention times represent the affinity of peptides to the stationary phase; the precise calculation of these affinities has proven to be a very complicated task. So far attempts have been limited mostly to RP-HPLC, where retention correlates linearly with peptide hydrophobicity. It was postulated in early 1980's that peptide hydrophobicity could be calculated as a sum of hydrophobicities of the constituent amino acid residues.[4] Several similar models were developed,[4-6] some of which featured introduction of correction factors for peptide length. These additive approaches remained state-of-the-art until around 2004, despite compelling evidence that peptide retention in RP-HPLC should also possess sequence-dependent features.[7] The situation changed dramatically with the development of new ionization techniques for biological macromolecules, such as ESI and MALDI, accompanied by rapid improvements in new mass measurement techniques. Abundant data sets of peptides with their measured retention times became available, rejuvenating the interest in peptide retention modeling. Several research groups have used proteomics-derived data to develop peptide retention prediction models.[8-13] While the typical additive models were able to reach correlation of experimental vs. predicted retention times of ~0.90, the best sequence-specific models have showed ~0.97-0.98 correlations.[8,9]

Despite the progress in modeling peptide retention in RP HPLC, some fundamental challenges still remain unanswered. Retention prediction algorithms have generally been optimized for a specific set of chromatographic conditions: the type of the sorbent, the ion-pairing modifier, column size, flow-rate, gradient slope. Previously, there have been no quantitative models developed for predicting S for peptidic compounds. This may be due in part to peptidic compounds being in a category of "irregular compounds" from the point of view of LSS theory.[22] Peptides exhibit significant not predictable variation of S and resulting separation selectivity in reverse phase chromatography. Understanding the factors that control the retention of peptides in reverse phase chromatography, such as S, will result in improved separation selectivity and methods for the analysis and isolation of peptides.

Accordingly, there is a need for improved methods and compositions for predicting S and separating peptides using RP-HPLC.

SUMMARY

In one aspect, the present disclosure provides a method for calculating the slope S of a peptide based on sequence-specific features of the peptide. The disclosure also provides a method for determining S for one or more peptides in a sample wherein a set of calibrating peptides with known values of S are used to determine retention time shifts for the peptides in the sample with respect to a reference peptide at two different solvent gradients in a reverse phase chromatography column. In another aspect the disclosure provides methods for separating or isolating a peptide using reverse phase chromatography by determining the retention time of the peptide using the value of S for that peptide.

Accordingly, in one aspect of the present disclosure there is provided a method for determining the slope S for a peptide comprising:

(a) providing a test sample comprising one or more peptides, (b) combining a set of calibrating peptides comprising a reference peptide with the test sample to form, together with the test sample, a combined test sample, wherein a slope S for each peptide in the set of calibrating peptides is known and the slope S represents a change in retention of the peptide in a reverse phase chromatography column with respect to a change in a mobile phase solvent gradient, (c) measuring a plurality of first retention times by, for each peptide in the combined test sample, measuring a first retention time for the peptide to travel through the reverse phase chromatography column at a first solvent gradient, wherein a solvent gradient represents an increase in solvent concentration in the reverse phase chromatography column over time, (d) measuring a plurality of second retention times by, for each peptide in the combined test sample, measuring a second retention time for the peptide to travel through the reverse phase chromatography column at a second solvent gradient different from the first solvent gradient, (e) calculating a plurality of retention time shifts, by, for each peptide in a plurality of peptides in the set of calibrating peptides, calculating a corresponding retention time shift relative to the reference peptide based on the first retention time and the second retention time for the peptide, and the first retention time and the second retention time for the reference peptide, (f) for at least one peptide in the test sample, calculating a corresponding retention time shift relative to the reference peptide based on the first retention time and the second retention time of the peptide, and the first retention time and the second retention time of the reference peptide as measured in steps (c) and (d), (g) determining a function F for determining S based on the retention time shifts for a plurality of the peptides in the set of calibrating peptides; and (h) for at least one peptide in the test sample, determining the value of S for the peptide using the function F and the retention time shift for the peptide calculated in (f).

In one embodiment, the method includes using mass spectroscopy to determine the retention times of the peptides, or to determine mass or sequence information about the peptides. In one embodiment the slope S for each peptide in the set of calibrating peptides is determined by isocratic elution using a similar column matrix and mobile phase as used to measure the retention times in steps (c) and (d) as set out above. Optionally, the methods described herein use a set of calibrating peptides comprising at least one of the peptides listed in Table 1. In one embodiment, the S values for each of the peptides in the set of calibrating peptides is between 10 and 50 or between 15 and 45.

In another aspect of the disclosure, there is provided a method for calculating a slope S for a peptide. In one embodiment, the slope S represents a change in retention of the peptide in a reverse phase chromatography column with respect to a change in a mobile phase gradient slope during reversed-phase chromatographic separation. In one embodiment, the method comprises:

(a) determining a peptide length, a peptide charge, a hydrophobicity and an amino acid sequence for the peptide; and (b) using a function F for calculating the slope S based on the peptide charge, the peptide length, the hydrophobicity and the amino acid sequence of the peptide.

In one embodiment, the slope S for a peptide is calculated using the function:

$$S=C1*Z^{C2}+C3*N^{C4}+C5*HI^{C6}+C7/Z+C8/N+C9/HI+ C10*ZN+C11*ZHI+C12*NHI+ C13*Z*N*HI^{C14}+B+S_{aa}+SSSF;$$

where N is the peptide length, Z is the peptide charge, HI is the hydrophobicity of the peptide, $S_{aa}$ is calculated based on the number of occurrences of each amino acid in the peptide, SSSF is calculated based on the sequence of the peptide and where constant B and coefficients C1 to C14 are empirically determined.

In one embodiment, the term $S_{aa}$ is calculated by (a) identifying the number of occurrences of each amino acid in the peptide;

b) multiplying the number of occurrences of each amino acid in the peptide by a corresponding coefficient for that amino acid ($S_i$) listed in Table 2; and c) summing each of the products determined in step b) to give a value for $S_{aa}$.

In one embodiment, the term SSSF is calculated based on distribution of hydrophobic amino acid residues within the peptide. In one embodiment, a uniform distribution of hydrophobic amino acid residues increases the value of S for the peptide. In one embodiment the hydrophobic amino acid residues are leucine, isoleucine, phenylalanine, tryptophan, tyrosine, valine and methionine.

In one embodiment, the term SSSF is calculated based on positioning of acidic amino acids within the peptide adjacent to residues carrying positively charged amino groups. In one embodiment, the presence of neighboring acidic amino acids and positively charged amino groups decreases the value of S for the peptide. In one embodiment, the acidic amino acids are glutamic acid and aspartic acid and the positively charged amino groups are arginine, lysine, histidine and the N-terminus of the peptide.

In one embodiment, the value of the slope S determined or calculated for a peptide can be used to predict the chromatographic behavior of the peptide. For example, the slope S can be used to determine an expected retention time for the peptide at a first set of chromatographic conditions based on a measured retention time for the peptide at a different set of chromatographic conditions. In one embodiment, the slope S is used to determine a retention time shift of the peptide in response to variation of gradient slope, flow rate or column size. In one embodiment, slope S can be used to determine a retention time for the peptide and isolate the peptide by collecting an eluant from a reverse phase chromatography column at the retention time.

According to another aspect of the present disclosure there is provided a method for separating or isolating a peptide from a sample, the method comprising:

(a) providing a sample comprising the peptide;

(b) calculating a slope S for the peptide, wherein the slope S is calculated based on peptide charge, peptide length, hydrophobicity and amino acid sequence of the peptide;

(c) introducing the sample into a reverse phase chromatography column with a mobile phase;
(d) determining a retention time for the peptide in the reverse phase chromatography column based on the slope S; and
(e) collecting an eluent out of the column at the predicted retention time for the peptide calculated in (e), wherein the eluent comprises the peptide.

In one embodiment, the slope S is calculated using one of the embodiments for determining or calculating a slope S as described herein. In one embodiment, the step of calculating the slope S comprises summing of the product of the number of occurrences for each amino acid in the peptide by the corresponding coefficient ($S_i$) in Table 2. In another embodiment, the step of calculating the slope S comprises including a factor based on the distribution of hydrophobic amino acids (L, I, F, W, Y, V, M) within the peptide chain wherein uniform distribution of these residues increases S. In one embodiment, the step of calculating the slope S comprises including a factor based on the positioning of acidic amino acids (E, D) within the peptide chain adjacent to the residues carrying positively charged amino groups at the pH of the eluent (R, K, H, N-terminus) wherein the presence of neighboring acidic amino acids and positively charged amino groups decreases the value of S. In one embodiment, the value of S is determined based on a retention time for the peptide measured at a different set of chromatographic conditions than those used in for separating the peptide in a reverse phase chromatography column with a mobile phase.

In one embodiment, the method comprises using the slope S to determine a retention time for the peptide and separating or isolating the peptide by collecting an eluant from a reverse phase chromatography column at the retention time. In one embodiment, the method comprises using the slope S to determine a retention time shift of the peptide in response to variation of gradient slope, flow rate or column size in a reverse phase chromatography column. In one embodiment, the method includes adjustment of the retention times for the transfer of scheduled MRM/SRM protocols between different RP-LC systems. In one embodiment, adjustment of retention times provides optimal performance for peptide retention prediction protocols and corresponding isolation or identification of proteins. In another embodiment, the methods described herein include methods to predict selectivity variation upon changing the "physical" parameters of RP-HPLC system for selectivity optimization in analytical and preparative-scale peptide chromatography.

In one aspect of the disclosure, there is provided one or more of the synthetic peptides listed in Table 1. In one embodiment, the peptides are useful for the determination of S according to the methods describes herein. In one embodiment, there is also provided a set of peptides comprising two or more of the peptides listed in Table 1. In one embodiment, there is provided a kit for determining the S value of a peptide comprising one or more of the peptides set out in Table 1 and instructions for use thereof.

In one aspect of the disclosure, there is provided a computer system comprising a processor specifically programmed to calculate a value of S according to the methods described herein.

In one aspect of the disclosure, there is provided an apparatus comprising a reverse phase HPLC column, a mass spectrometer, and computer system comprising a processor specifically programmed to calculate a value of S according to the methods described herein.

In one aspect of the disclosure, there is provided a computer readable media encoding a computer program for calculating a value of S according to the methods described herein.

Other features and advantages of the present invention will become apparent from the following detailed description. It should be understood, however, that the detailed description and the specific examples while indicating preferred embodiments of the invention are given by way of illustration only, since various changes and modifications within the spirit and scope of the invention will become apparent to those skilled in the art from this detailed description.

BRIEF DESCRIPTION OF THE DRAWINGS

The disclosure will now be described in greater detail with reference to the drawings in which:

FIG. 4 shows predicted S-values for the model peptide mixture using various models. A—the Stadalius et al.[17] approach; B—a model based on peptide charge, length and hydrophobicity; C the sequence-specific model described in the present application. D: corrected $t_R$ vs. $t_R$ correlations for the test peptide mixture for the gradient slopes differ 2-times and 4-times showing improved fit compared to the Figures in 2a.

DETAILED DESCRIPTION OF THE INVENTION

Definitions

Figure 1:
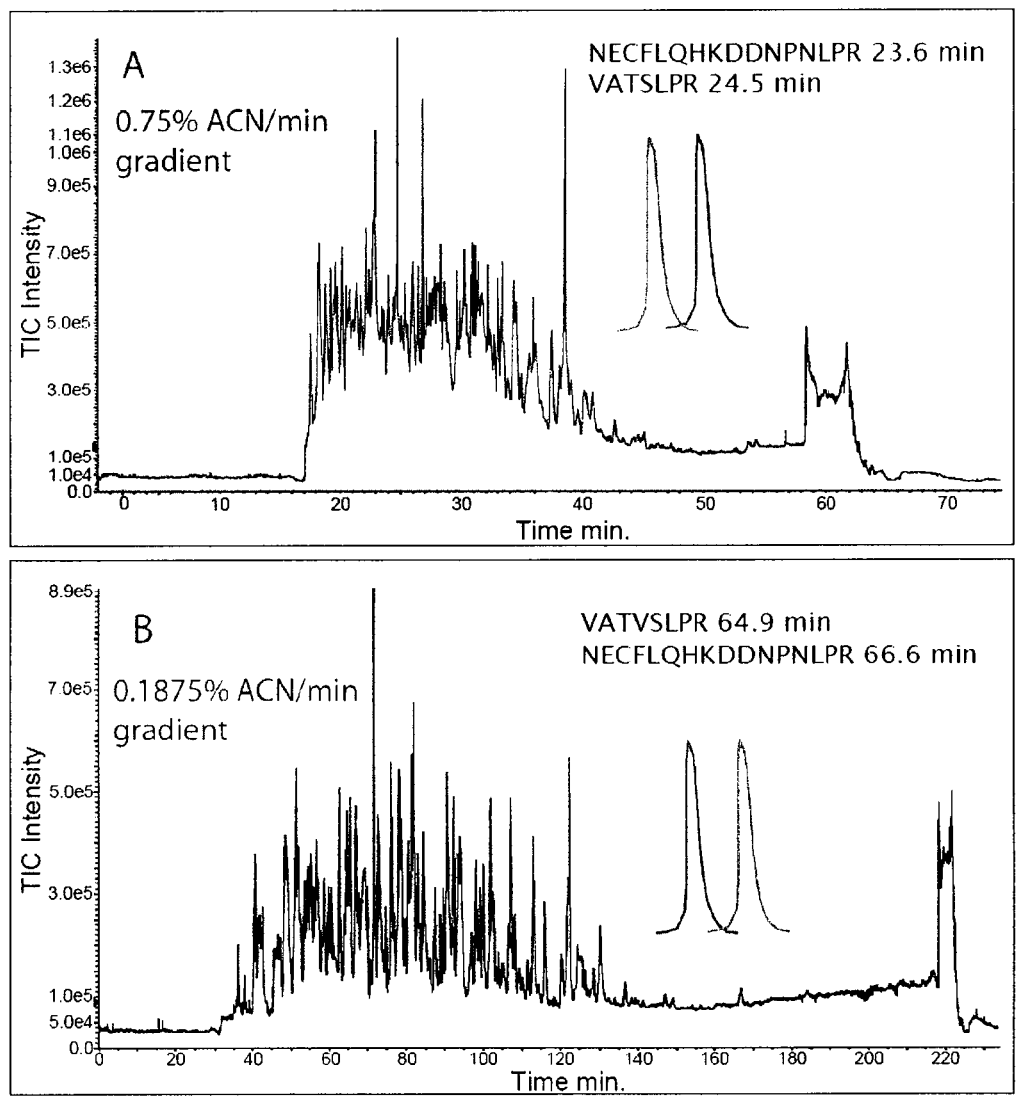
FIG. 1 shows variation in peptide separation selectivity with altering the gradient slope. A, B—TIC chromatograms of a test peptide mixture (tryptic digest of human proteins) using two different gradients: 0.75 and 0.1875% acetonitrile per minute. The retention times of the peptides NECFLQH-KDDNPNLPR (SEQ ID NO: 1) and VATVSLPR (SEQ ID NO: 2) are shown. C—a schematic representation of the retention behavior of two peptides with different S-values at isocratic and gradient conditions.
Figure 1:
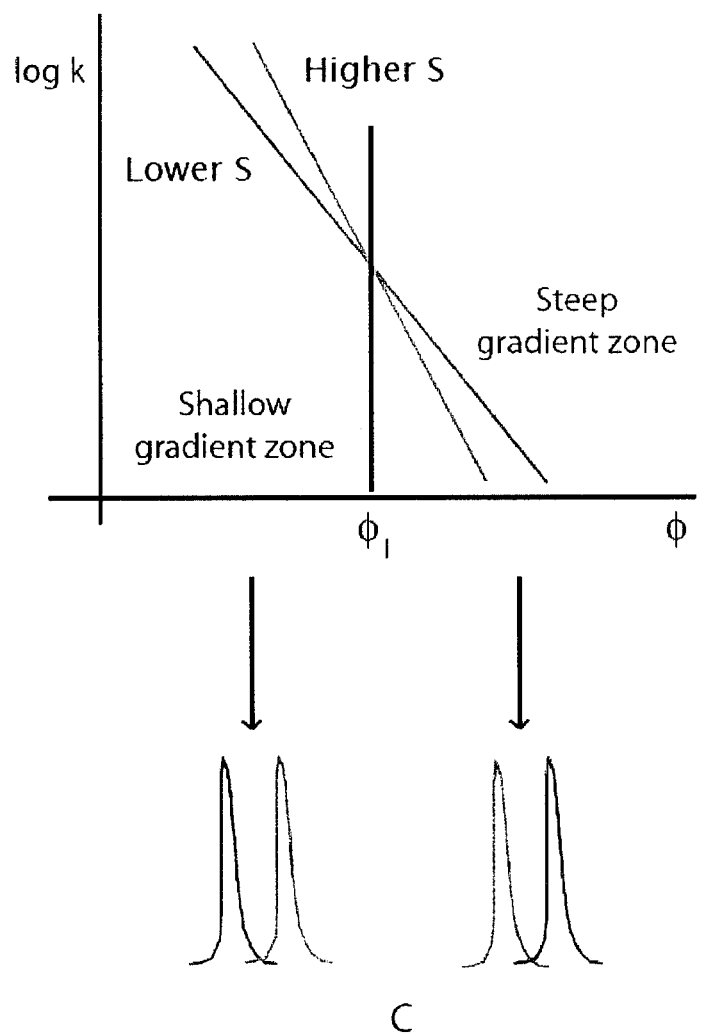

The following abbreviations are used throughout the disclosure and have their standard meanings known in the art:
Natural Amino Acids:

| | | |
|---|---|---|
| Alanine | ALA | A |
| Cysteine | CYS | C |
| Aspartic Acid | ASP | D |
| Glutamic Acid | GLU | E |
| Phynylalanine | PHE | F |
| Glycine | GLY | G |

-continued

| | | |
|---|---|---|
| Histidine | HIS | H |
| Isoleucine | ILE | I |
| Lysine | LYS | K |
| Leucine | LEU | L |
| Methionine | MET | M |
| Asparagine | ASN | N |
| Proline | PRO | P |
| Glutamine | GLN | Q |
| Arginine | ARG | R |
| Serine | SER | S |
| Threonine | THR | T |
| Valine | VAL | V |
| Tryptophan | TRP | W |
| Tyrosine | TYR | Y |

RT means retention time and means the elapsed time between the time of injection of a substance and the time of elution of the peak in chromatography.

RP means reversed-phase.

LC means liquid chromatography.

HPLC means high performance liquid chromatography.

ACN % means percent acetonitrile and refers to the amount in percent by volume of acetonitrile in the eluent.

TFA means trifluoroacetic acid.

FA means fluoroacetic acid.

MALDI means matrix assisted laser desorption ionization.

ESI means electrospray ionization.

MS means mass spectrometry.

HPLC means high performance liquid chromatography.

As used herein the term "chromatography" refers to a separation technique wherein a mixture comprising an analyte is passed through a stationary phase and separates the analyte from other molecules in the mixture based on differential partitioning between the mobile and stationary phases.

As used herein, the term "reversed-phase chromatography" refers to a chromatographic separation technique wherein the stationary phase is non-polar.

As used herein, the term "isocratic elution" means that the composition of the mobile phase remains constant throughout the chromatographic run.

As used herein, the term "gradient elution" means that the composition of the mobile phase changes during a chromatographic run.

The term "mobile phase" refers to a solution that is run through a chromatography column. A "mobile phase" can include one or more solvents, water and/or ion-pairing agents. The term "mobile phase" also includes one or more analytes such as peptides, which are being separated in a column containing the stationary phase.

As used herein, the term "solvent" refers to a non-aqueous component of the mobile phase, as commonly understood in the art of reverse-chromatography. Examples of solvents suitable for use in reversed-phase chromatography include acetonitrile and methanol.

As used herein, the term "eluent" refers to a mobile phase as it is delivered through a chromatography column.

As used herein, the term "solvent gradient" refers to a rate of change in concentration of a solvent in a mobile phase, as commonly understood in the art of reversed-phase chromatography. For example, the solvent gradient can be expressed as a percentage of solvent per unit time, i.e. 0.75% per minute.

The term "test sample" refers to a sample that contains one or more proteins or peptides. The term "test sample" optionally includes samples that have been digested with an enzyme, such as trypsin, to produce a test sample that comprises tryptic peptides. As used herein the term "peptide" refers to two or more amino acids linked by a peptide bond, and includes synthetic and natural peptides as well as peptides that are modified.

As used herein, the term "set of calibrating peptides" refers to two or more peptides for which a value of S for each peptide has been pre-determined.

As used herein, the term "reference peptide" refers to one of the peptides in the set of calibrating peptides used to calculate a retention shift.

As used herein, the phrase "a slope S for a peptide" refers to the slope S in the basic linear-solvent-strength theory given by $\log k = \log k_0 - S^*\phi$; where k is the retention factor at an organic solvent volume fraction $\phi$ and $k_0$ is the retention factor at $\phi=0$. "S" represents a change in retention of a peptide in a reverse phase chromatography column with respect to a change in a mobile phase gradient slope during reverse-phase chromatographic separation In understanding the scope of the present disclosure, the term "comprising" and its derivatives, as used herein, are intended to be open ended terms that specify the presence of the stated features, elements, components, groups, integers, and/or steps, but do not exclude the presence of other unstated features, elements, components, groups, integers and/or steps. The foregoing also applies to words having similar meanings such as the terms, "including", "having" and their derivatives. Finally, terms of degree such as "substantially", "about" and "approximately" as used herein mean a reasonable amount of deviation of the modified term such that the end result is not significantly changed. These terms of degree should be construed as including a deviation of at least ±5% of the modified term if this deviation would not negate the meaning of the word it modifies.

One of the missing pieces of puzzle in understanding the variation of slopes S is the charge of peptide.[23] Driven by the original assumption that S is controlled by peptide length, hydrophobicity and charge, a set of 37 peptides were designed, synthesized and the S-values for the peptides were precisely measured for 100 Å C18 sorbent with 0.1% trifluoroacetic acid as the ion-pairing modifier. The compositional design of the sequences allowed the monitoring of the effect of only one parameter while locking the other two parameters constant. The results unequivocally indicated that S increases with peptide charge and length, while the influence of hydrophobicity is more complex. Following these measurements, a simple model for predicting S with only three variables was optimized.[23] The resulting correlation of measured vs. predicted slopes S gave a ~0.97 $R^2$-value, supporting the original hypothesis.

This was achieved for the set of closely related synthetic peptides designed to represent a typical tryptic species observed in bottom-up proteomics experiments. Undoubtedly, any "real-life" set of tryptic peptides will possess wider variation of peptide's physical properties and sequence-derived features. It was expected that sequence-specific factors, which affect slope S, would be found similar to ones affecting overall peptide hydrophobicity in our SSRCalc models.[8] As described herein, a method has been developed for the measurement of the S-values for diverse set of tryptic species in typical nanoRP-HPLC/MS proteomic setup and development of the Sequence-Specific Slope Calculator (SSSC) model. Its application to the fine retention time re-adjustment for the LC-MS/MS analyses performed with various slopes of water/acetonitrile gradient is also demonstrated as set out in the Examples contained herein.

In one embodiment, the present disclosure provides a method for determining the value of the slope S for a peptide. The value of S for the set of peptides shown in Table 1 was experimentally determined using isocratic elution reverse phase chromatography as set out in Example 2. These calibrating peptides were then used to determine the value of S for a sample containing a complex mixture of tryptic peptides by spiking the sample with the set of calibrating peptides and measuring the relative shift in retention time for each of the peptides in the sample with respect to a reference peptide in the set of calibrating peptides during reverse phase liquid chromatography at two different solvent gradients. The shift in retention time for each of the peptides in the sample going from the first gradient to the second gradient was then used to determine S for each peptide based on a standard curve generated using the observed retention time shifts and known values of S for the calibrating set of peptides. The peptides eluting from the column were detected by mass spectroscopy, which allowed for each peptide to be identified with respect to mass and a corresponding sequence identity. Table 4 provides the experimentally derived S values and sequences for the set of ~300 peptides that were identified in the complex sample.

Accordingly, in one embodiment there is provided a method comprising providing a test sample comprising one or more peptides and combining a set of calibrating peptides that includes a reference peptide with the test sample to form a combined test sample. In one embodiment, the slope S for each peptide in the calibrating set of peptides has been predetermined. In one embodiment, the method further comprises analyzing the combined sample by reverse phase liquid chromatography to measure the retention time for each peptide in the combined sample at a first solvent gradient in the RP-LC column. In one embodiment, the retention time for each peptide is measured using mass spectroscopy. In one embodiment, the sequence identities of the peptides are also determined using mass spectroscopy, such as by reference to tables or databases of mass spectroscopy data. Optionally, the retention times for each peptide can be measured by other methods know in the art such as optical detection. In one embodiment, the method comprises running the combined sample through the same RP-HPLC column using a different solvent gradient and measuring the retention times for each peptide at this second solvent gradient. The retentions times for a peptide measured at different solvent gradients allow the calculation of a retention time shift. In one embodiment, the retention time shift is calculated for a peptide with respect to the measured retention times for a reference peptide. In one embodiment, the reference peptide is one of the peptides in the calibrated set of peptides with a pre-determined value for its slope S. As shown in Example 8, the retention time shift of a peptide is related to its value of S. In one embodiment, a function F is then determined for calculating S based on the measured retention time shifts for a plurality of the peptides in the set of calibrating peptides for which the value of S is already known. In one embodiment, this function may then be used to determine the value of S for any one of the peptides in the sample for which a retention time shift has been measured.

In one embodiment, the set of calibrating peptides comprises at least one of the peptides listed in Table 1. Optionally, the calibrating peptides may be chosen so as to have a broad range of S values. In one embodiment, the values of S for each of the peptides in the set of calibrating peptides is between 10 and 50 or between 15 and 45.

In one embodiment, the method comprises determining a function relating the values of S and the measured retention time shifts for the set of calibrating peptides. In one embodiment, the function is of the form:

$$\Delta = 100 * \log(G_0/G_1)/S + A \quad (4)$$

wherein $\Delta$ is the retention time shift, $G_0$ and $G_1$ are the first and second solvent gradients, and A is a constant related to system parameters $t_0$, $t_D$, and the observed retention times of the reference peptide under gradients $G_0$ and $G_1$.

In another embodiment, the function F is of the form:

$$\Delta = B * \ln(S) + A$$

wherein $\Delta$ is the retention time shift and A and B are constants.

In one embodiment, the retention times of the peptides are measured at a first and second solvent gradients. In one embodiment, the ratio of the first solvent gradient and the second solvent gradient is between 2 and 100. In another embodiment, the ratio of the first solvent gradient and the second solvent gradient is between 3 and 6. In one embodiment, the solvent is acetonitrile and the first solvent gradient is 0.75% acetonitrile per minute and the second solvent gradient is 0.1875% acetonitrile per minute.

In one embodiment, the retention time shifts are calculated for the peptides in the set of calibrating peptides, and for at least one peptide in the test sample. In one embodiment, the retention time shift is calculated using equation (3):

$$\Delta = (t_{RG0} - t_{RRPG0}) * G_0 - (t_{RG1} - t_{RRPG1}) * G_1 \quad (3)$$

wherein $\Delta$ is the retention time shift, $t_{RG0}$ is the retention time of the peptide at the first solvent gradient $G_0$, $t_{RRPG0}$ is the retention time of the reference peptide at the first solvent gradient, $t_{RG1}$ is the retention time of the peptide at the second solvent gradient, $t_{RRPG1}$ is the retention time of the reference peptide at the second solvent gradient, $G_0$ is the first solvent gradient and $G_1$ is the second solvent gradient. In one embodiment, the retention time shift is expressed as a percentage of solvent scale, for example as 1% acetonitrile. In another embodiment, the retention time shift is expressed as a fraction.

Figure 2:
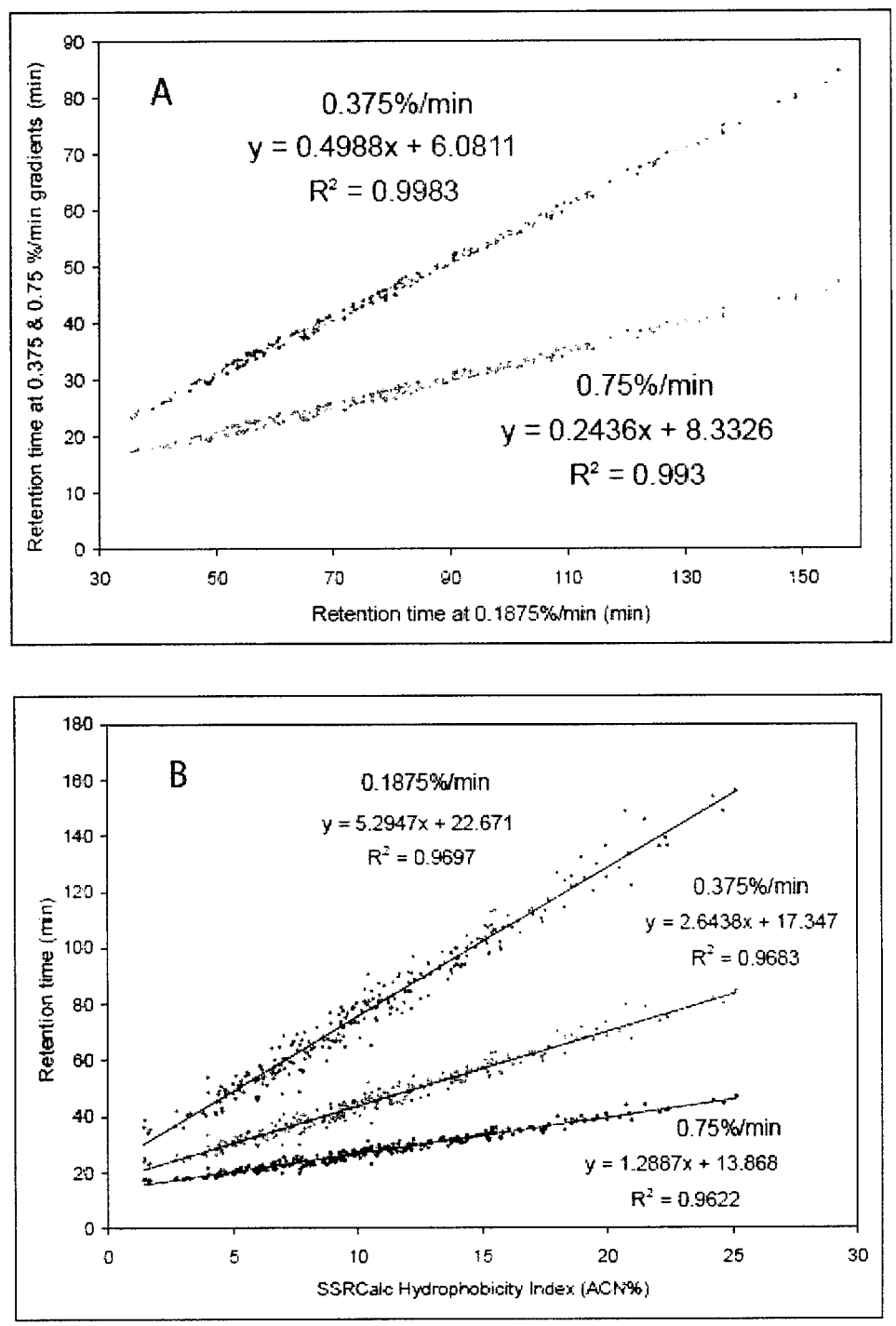
FIG. 2 shows the effect of the gradient slope on the separation selectivity for a large set of peptides. A—$t_R$ vs. $t_R$ correlations where the gradient slopes differ by 2-times and 4-times. B—the effect of gradient slope on the accuracy of SSRCalc (formic acid) peptide retention prediction using 0.75, 0.375 and 0.1875% acetonitrile per minute gradients.
Figure 3:
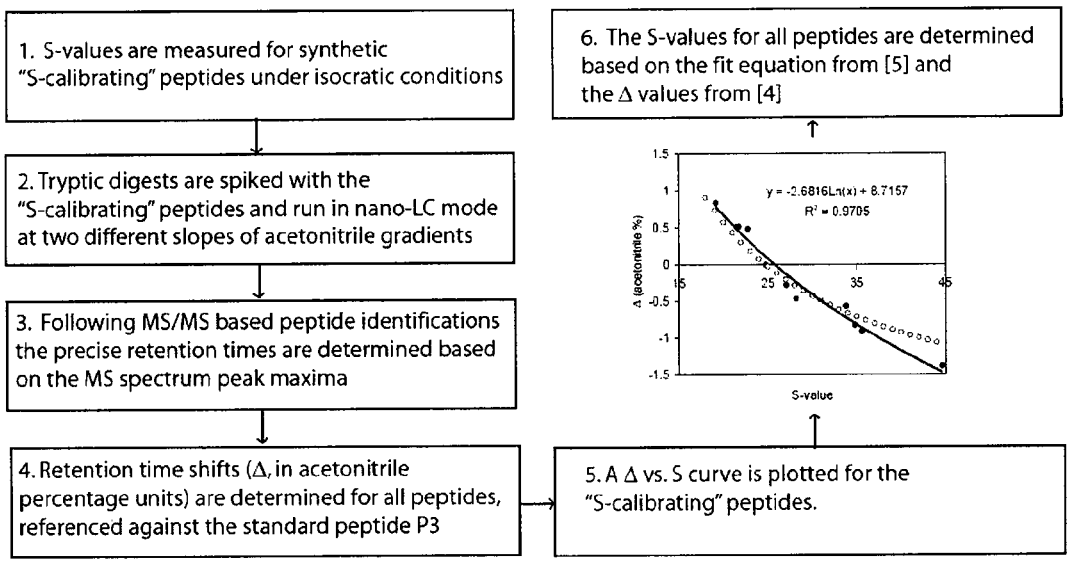
FIG. 3 shows one embodiment of a workflow for determining the values of S for extensive peptide sets observed from nano-flow RP HPLC-MS proteomic experiments. In the chart, the points (●) show experimental Δ vs. S dependence for the 11 "S-calibrating" peptides shown in Table 1; the solid line approximates the dependence with a logarithmic function; the open circles (○) show a best fit reciprocal function Δ=60.206/S−2.431.

In another aspect, the present disclosure provides a method for calculating S for a peptide based on peptide charge, length, hydrophobicity and various sequence-specific features of the peptide. S-values for a set of model peptides were measured experimentally according to the methods described herein and used to develop a predictive model for slope values as shown in FIG. 3 and Table 3. As set out in Example 5, this model (referred to herein as "SSSCalc") was tested and shown to improve the correlations for the independent data set shown in FIG. 2A.

Accordingly, in one embodiment there is provided a method for separating or isolating a peptide from a sample containing the peptide comprising calculating a slope S for the peptide, wherein the slope S is calculated based on peptide charge, peptide length, hydrophobicity and amino acid sequence of the peptide. In one embodiment, the retention time of the peptide in a reverse phase chromatography column is determined using the slope S for the peptide. In one embodiment, the sample is then introduced into the reverse phase chromatography column and an eluent is collected out of the column at the predicted retention time for the peptide calculated.

In one embodiment, the slope S is calculated using the function:

$$S = C1*Z^{C2} + C3*N^{C4} + C5*HI^{C6} + C7/Z + C8/N + C9/HI + C10*ZN + C11*ZHI + C12*NHI + C13*Z*N*HI^{C14} + B + S_{aa} + SSSF;$$

where for each peptide N is a peptide length, Z is a peptide charge, HI is hydrophobicity of the peptide, $S_{aa}$ is calculated based on the frequency of each amino acid residue in the peptide, SSSF is a sum of sequence-specific factors and where constant B and coefficients C1 to C14 are empirically determined.

In one embodiment, the term $S_{aa}$ is calculated by summing of the product of the number of occurrences for each amino acid in the peptide by the corresponding coefficient ($S_i$) in Table 2.

In one embodiment, the hydrophobicity index (HI) is calculated as described in Krokhin, O. V.; Spicer, V. *Anal Chem* 2009, 81, 9522-9530 (herein incorporated by reference). In one embodiment, hydrophobicity values are calculated as described in Krokhin, O. V. *Anal. Chem.* 2006, 78, 7785-7795 (herein incorporated by reference) and mapped onto the hydrophobicity index (HI) scale described in Krokhin, O. V.; Spicer, V. *Anal Chem* 2009, 81, 9522-9530. Other methods known in the art for determining the hydrophobicity of a peptide may also be used to determine values for HI.

In one embodiment, the term SSSF is calculated based on the amino acid sequence of the peptide. For example, in one embodiment, the term SSSF is calculated by summing factors related to:
  i) the distribution of hydrophobic amino acids (L, I, F, W, Y, V, M) within the peptide chain wherein uniform distribution of these residues increases S; and
  ii) the positioning of acidic amino acids (E, D) within the peptide chain adjacent to the residues carrying positively charged amino groups at the pH of the eluent (R, K, H, N-terminus) wherein the presence of neighboring acidic amino acids and positively charged amino groups decreases the value of S.

Figure 5:
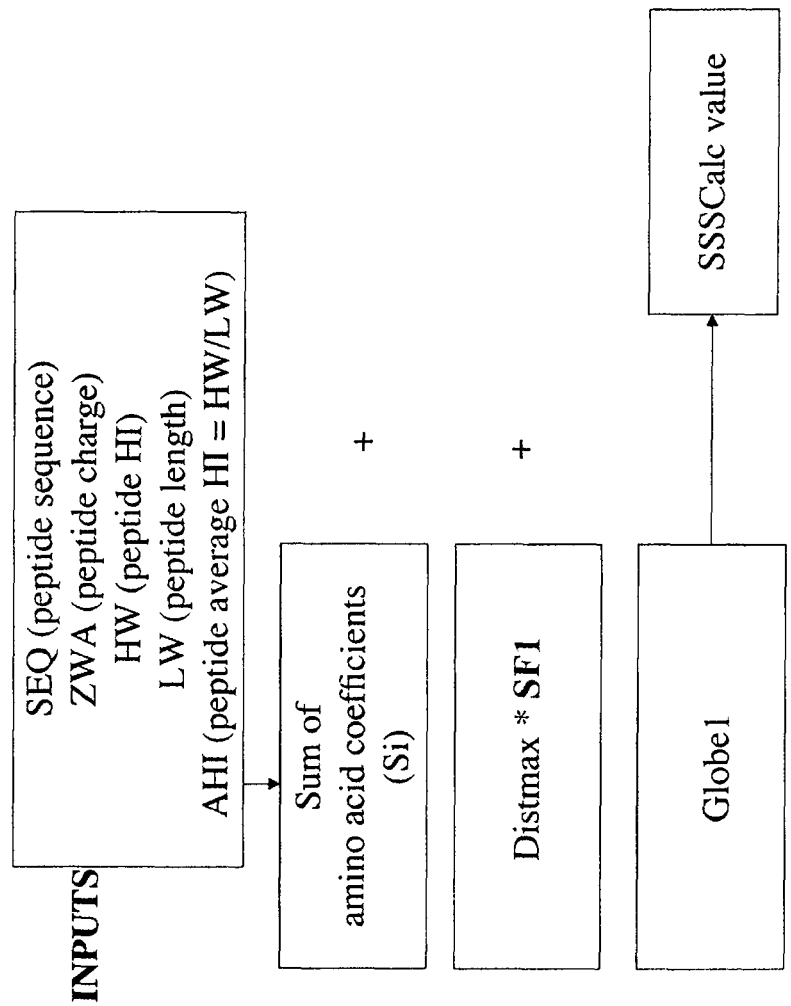
FIG. 5 provides a series of flow charts showing the calculation of S based on the amino acid sequence of a peptide according to the SSSCalc model as set out in Example 6.
Figure 5:
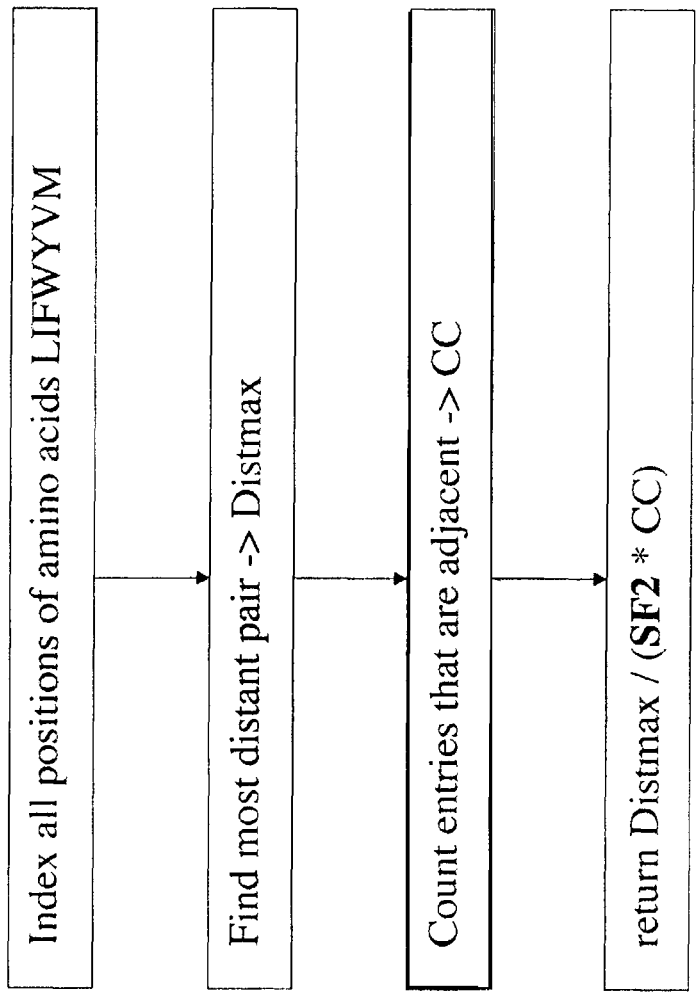
Figure 5:
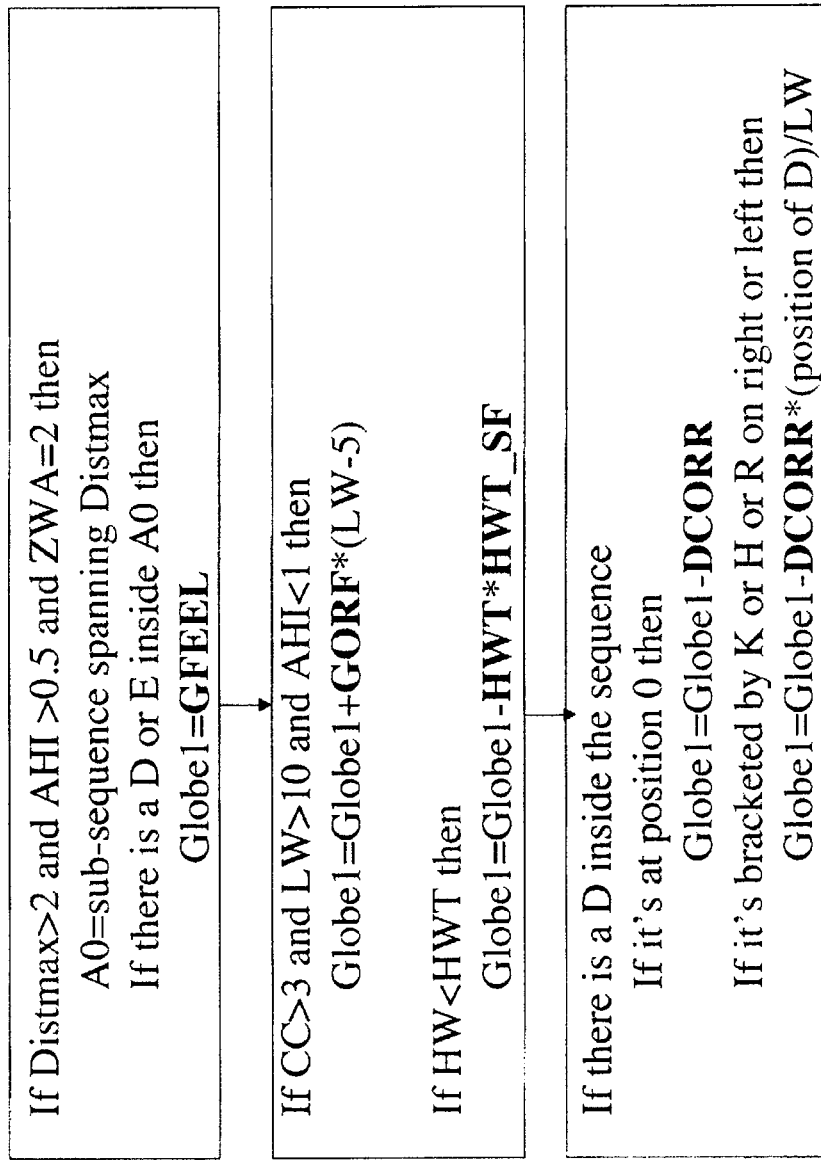
Figure 5:
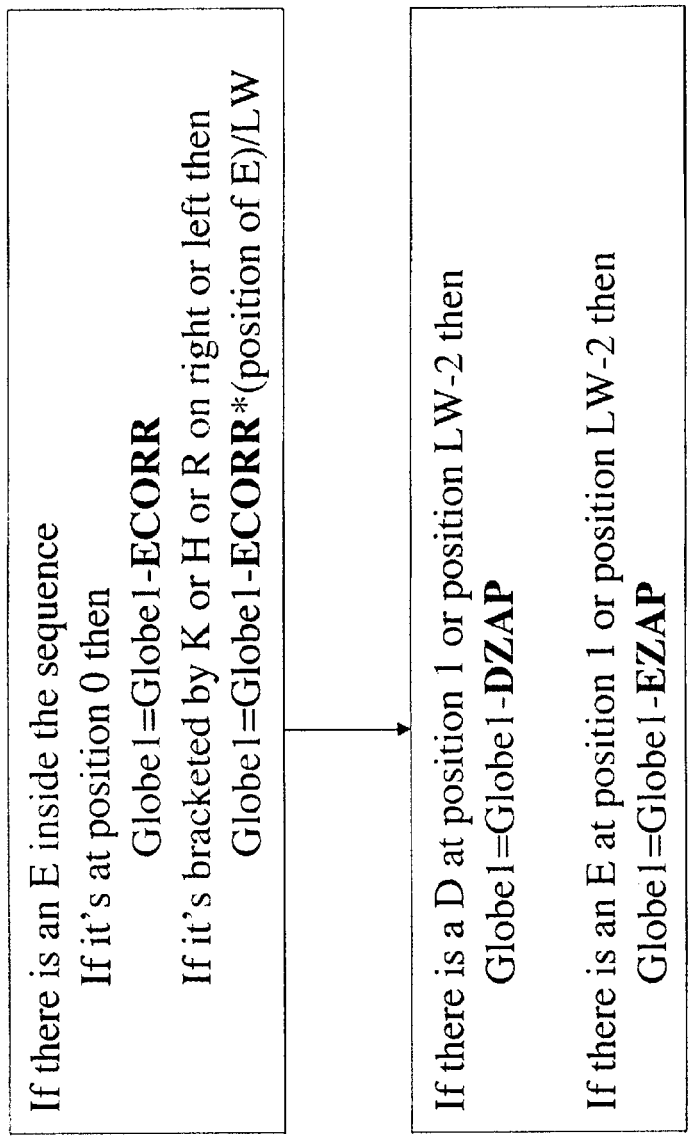
Figure 5:
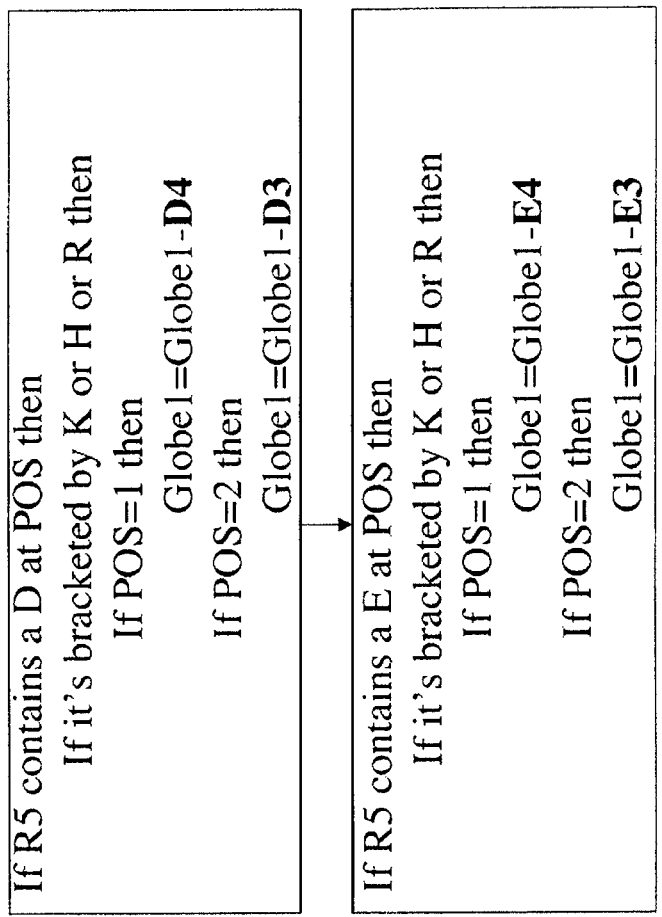
Figure 5:
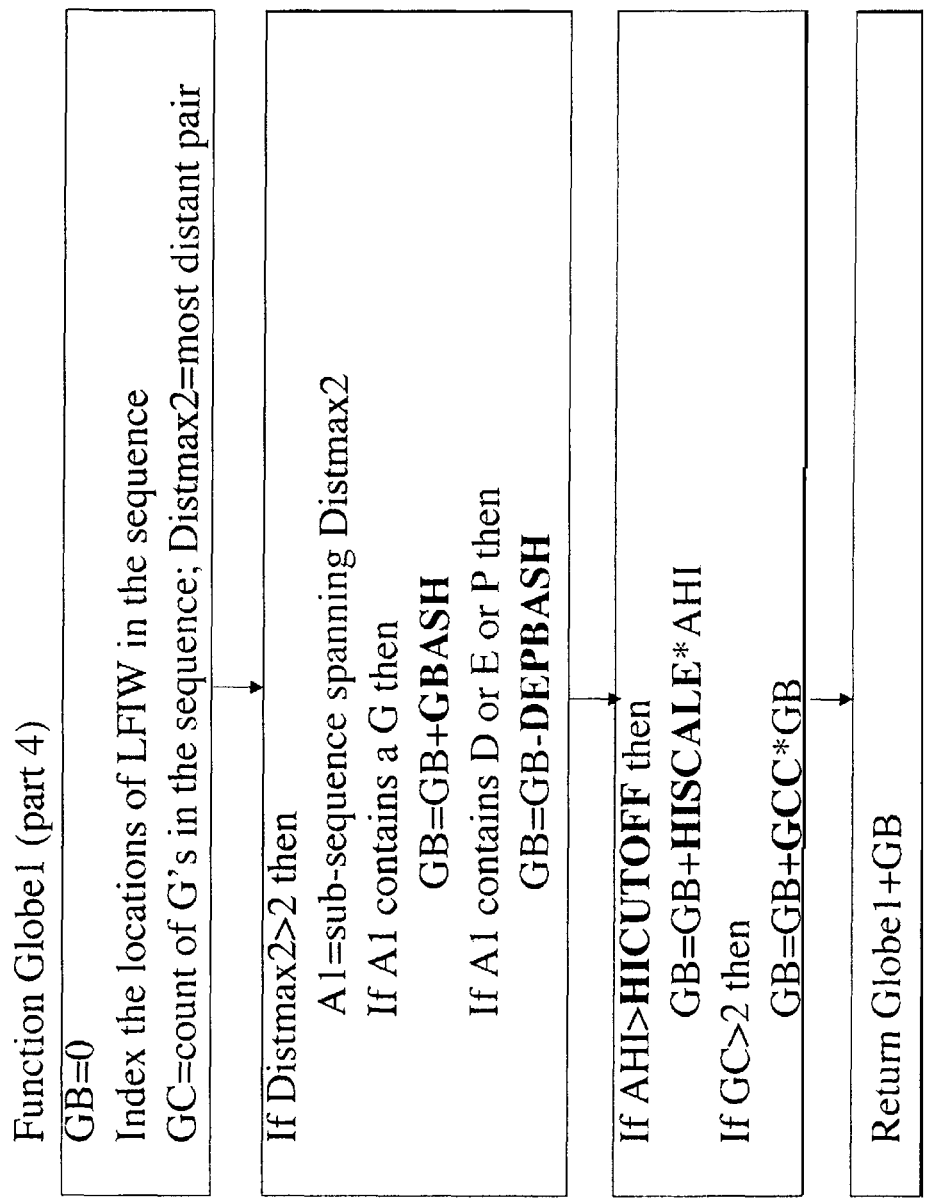

In one embodiment, the term SSSF can be determined according to the set of algorithmic conditional steps shown in FIG. 5. For example, in one embodiment SSSF=Distmax*SF1+Globe1, wherein Distmax*SF1 is a measure of the distribution of hydrophobic amino acids within the peptide, and Globe1 is a measure of the positioning of acidic amino acids adjacent to positively charged amino acids.

In one embodiment, the methods described herein include isolating or separating a peptide based on its value of S by collecting an eluant from the reverse phase chromatography column at a predicted retention time. In one embodiment, the methods optionally include concatenating into one dataset peptide retention data sets collected using "chemically" similar separation systems with different "physical" settings using a set of a-priori calculations based on the predicted value of S. In another embodiment, the methods provide for re-adjustment of the retention times for the transfer of scheduled MRM/SRM protocols between different RP-LC systems with different physical parameters, such as gradient slope, flow rate, and columns size.

In one embodiment, the methods further include adjustment of retention times to provide optimal performance for peptide retention prediction protocols and corresponding isolation or identification of proteins, based on the calculated or determined value of S for a peptide. In another embodiment, the methods described herein include methods to predict selectivity variation upon changing the "physical" parameters of an RP-HPLC system (such as gradient slope, flow rate, and columns size) for selectivity optimization in analytical and preparative-scale peptide chromatography. In one embodiment, the methods described herein can be used for the inter-laboratory collection of peptide retention data obtained using chromatographic systems of different physical parameters.

In one embodiment, the disclosure provides the peptides listed in Table 1 that are suitable for use in the methods for determining S as described herein. The peptides of the disclosure are prepared, for example, by chemical synthesis using techniques known in the chemistry of proteins such as solid phase synthesis (Merrifield, 1964, J. Am. Chem. Assoc. 85:2149-2154) or synthesis in homogenous solution (Houbenweyl, 1987, Methods of Organic Chemistry, ed. E. Wansch, Vol. 15 I and II, Thieme, Stuttgart).

According to an embodiment of the present disclosure, the peptides are synthesized by step-by-step building of the peptide chain beginning with the C-terminal amino acid. The process involves maximum blocking of functional groups, starting from an amino acid alkyl ester, using the method of active esters.

In a suitable embodiment, the method involves the blocking of the amino, carboxyl and other reactive side groups of the amino acid(s) which are known to react during the synthesis. Suitable blocking agents are known to a person skilled in the art. For example, a suitable carboxy blocking agent include, without limitation, ethyl, nitrobenzyl, and t-butyl. A suitable amino blocking agent include, without limitation, fluorenylmethoxycarbonyl (Fmoc), carbobenzoxy, tosyl, trifluoracetyl and, suitably, t-butyloxycarbonyl (Boc). The amino acids are then coupled and the blocking agents subsequently removed. The peptide is optionally further purified using reverse phase chromatography.

The peptides of the disclosure are also prepared, for example, using standard recombinant DNA technology by transforming a suitable cell with a DNA molecule encoding the peptide and expressing the peptide in the cell and isolating the peptide. Such techniques are well known in the art (see for example, Maniatis, T., Fritsch, E. F., and Sambrook, J. (1982) Molecular Cloning: A Laboratory Manual, Cold Spring Harbor Laboratory, Cold Spring Harbor, N.Y.).

The composition of the present disclosure may also be incorporated in to a kit. In an embodiment the kits comprises any one, two, three, four, five, six, seven, eight, nine, ten, or eleven of the peptides listed in Table 1 and instructions for use.

In an embodiment the instructions describe the use of the peptides as a standard for liquid chromatography, suitably RP liquid chromatography, more suitably RP HPLC. In a further embodiment, the kit comprises reagents and materials for use in liquid chromatography, suitably RP liquid chromatography, more suitably RP HPLC.

In one embodiment, the methods described herein may be implemented in hardware or software, or a combination of both. However, these embodiments may be implemented in computer programs executing on programmable computers, each computer including at least one processor, a data storage system (including volatile and non-volatile memory and/or storage elements), and at least one communication interface. For example, the programmable computers may be a server, network appliance, set-top box, embedded device, computer expansion module, personal computer, laptop, personal data assistant, or mobile device. Program code is applied to input data to perform the functions described herein and to generate output information. The output information is applied to one or more output devices, in known fashion. For example, in one embodiment the output information is the slope S for a peptide or a retention time for the peptide traveling in a reverse-phase chromatography column as described herein.

Each program may be implemented in a high level procedural or object oriented programming or scripting language, or both, to communicate with a computer system. However, alternatively the programs may be implemented in assembly or machine language, if desired. In any case, the language may be a compiled or interpreted language. Each such computer program may be stored on a storage media or a device (e.g. ROM or magnetic diskette), readable by a general or special purpose programmable computer, for configuring and operating the computer when the storage media or device is read by the computer to perform the procedures described herein. Embodiments of the system may also be considered to be implemented as a non-transitory computer-readable storage medium, configured with a computer program, where the storage medium so configured causes a computer to operate in a specific and predefined manner to perform the functions described herein.

Furthermore, the system, processes and methods of the described embodiments are capable of being distributed in a computer program product including a physical non-transitory computer readable medium that bears computer usable instructions for one or more processors. The medium may be provided in various forms, including one or more diskettes, compact disks, tapes, chips, magnetic and electronic storage media, and the like. The computer useable instructions may also be in various forms, including compiled and non-compiled code.

All publications, patents and patent applications referenced herein are incorporated by reference in their entirety to the same extent as if each individual publication, patent or patent application was specifically and individually indicated to be incorporated by reference in its entirety.

The following non-limiting examples are illustrative of the present disclosure:

EXAMPLES

Materials and Methods

Reagents. Deionized (18 MΩ) water and HPLC-grade acetonitrile were used for the preparation of eluents. All chemicals were sourced from Sigma Aldrich (St-Louis, Mo.) unless noted otherwise. The 11 model peptides used to determine slopes S in isocratic elution mode were custom synthesized by BioSynthesis Inc. (Lewisville, Tex.). Table 1 shows the list of peptides, together with their core properties: molecular weight, charge, length, SSRCalc hydrophobicity and measured S-values.

Proteins and protein digestion. Tryptic digests of two different protein mixtures were utilized. The "test peptide mixture" contained human proteins: albumin, transferrin, fibrinogen. The "model peptide mixture" contained bovine proteins: albumin, transferrin, fibrinogen, catalase. Equimolar mixtures of the proteins were prepared, reduced with DTT, alkylated with iodoacetamide and digested with sequencing-grade modified trypsin (Promega, Madison, Wis.). Prior to nano-LC MS/MS analysis, mixtures were diluted with buffer A (0.1% formic acid in water) and spiked with the 6 standard peptides P1-P6[24] for test mixture and the set of 11 model peptides (described elsewhere[23]) for a model mixture. All dilutions were performed to provide an injection of ~100 fmole of each component into the nanoRP-HPLC MS system.

Chromatography. All chromatographic experiments were conducted at a controlled temperature of 22-23° C. For isocratic measurement of the slope values, a micro-Agilent 1100 Series system (Agilent Technologies, Wilmington, Del.), was used with a 1 mm×100 mm 5 μm Luna C18(2) (Phenomenex, Torrance, Calif.) column and a UV detector operated at 214 nm. Both eluents A (water) and B (acetonitrile) contained 0.1% formic acid as ion-pairing modifier. Stock solutions of the 11 standard peptides (~1 mg/ml) were prepared by dissolving each peptide in 1 ml of 0.1% FA in water or a 20% acetonitrile solution. Ten microliters of sample was injected. Individual peptides were diluted to provide ~0.5-1 μg injection of each component using a 10 μl loop. The dead volume of the column and connecting tubings was determined by injecting a non-retained compound (water) and measuring the elution time of the negative peak at a 150 μL/min flow rate. Retention factors for isocratic elution were calculated using the formula: $k=(t_R-t_0)/t_{0c}$; where $t_R$ is the retention time, $t_0$ is the system (column and tubings) dead time, and $t_{0c}$ is the column dead time. Additional details of measuring S-values via constructing log k vs. φ plots are provided elsewhere.[24]

The nano-LC MS/MS experiments were conducted using splitless Tempo LC system (Eksigent, Dublin, Calif.) with 20 μL sample injection via a 300 μm×5 mm PepMap100 (Dionex, Sunnyvale, Calif.) trap-column and a 100 μm×200 mm analytical column packed with 5 μm Luna C18(2) (Phenomenex, Torrance, Calif.). Tryptic digests of the mixtures were spiked with calibrating peptides (see Table 1) as described above, injected on the trap-column using buffer A as a carrier and separated using 0.1875, 0.375 and 0.75 percent acetonitrile per minute linear gradients starting from 0.5% acetonitrile at 500 nL/min flow rate. The composition of both eluents A and B was identical to one described above for normal-flow system. Gradient programs consisted of a 0.5-40% linear increase of buffer B in 213.2, 106.6 and 53.3 minutes, respectively. After each run the gradient columns were washed with 80% B for 3 minutes and equilibrated with the starting A:B ratio for 18 minutes.

Mass spectrometry. A QStar Elite mass spectrometer (Applied Biosystems, Foster City, Calif.) equipped with a MicroIonSpray II source was used in standard MS/MS information dependent acquisition (IDA) mode for LC-ESI analyses. Protein identification was performed using Protein Pilot 3.0 (Applied Biosystems, Foster City, Calif.) with a restricted database containing target protein sequences and the sequences of standard peptides. Retention times of identified species (peak maxima) were assigned manually. This procedure resulted in identification and confident assignment of retention times for 255 and 301 species in both test and model peptide mixtures, respectively.

Calculations and model development. Following the measurement of S-values for 301 peptides identified in the model peptide mixture, a general equation was used to obtain the best correlation between measured and calculated values. Similar to the previously described model for synthetic peptides,[23] a very general function of the form is given by:

$$S=C1*Z^{C2}+C3*N^{C4}+C5*HI^{C6}+C7/Z+C8/N+C9/HI+C10*ZN+C11*ZHI+C12*NHI+C13*Z*N*HI^{C14}+B$$

where for each peptide N is peptide length, Z is peptide charge and the values of HI are calculated using SSRCalc algorithm for formic acid conditions.[24] This model is referred to as the "NZHI" model. Parameter optimization code was written using Perl on a Mac Pro computer running the OS-X variant of UNIX. Following an initial "random walk" through parameter-space optimization of NZHI model,[23] additional sequence-specific features were introduced to improve observed correlation. Following each round of sequence-specific optimization procedures, the NZHI portion of the algorithm was also re-adjusted to provide optimum correlation.

The present disclosure provides a further model developed to incorporate sequence specific information into the calculation of the slope S for a peptide. This model is referred to as the "SSSC" (Sequence Specific Slope Calculator) model, and is described in Example 5 herein. In one embodiment, the model takes the form of the function:

$$S=C1*Z^{C2}+C3*N^{C4}+C5*HI^{C6}+C7/Z+C8/N+C9/HI+C10*ZN+C11*ZHI+C12*NHI+C13*Z*N*HI^{C14}+B+S_{aa}+SSSF;$$

where for each peptide N is a peptide length, Z is a peptide charge, HI is hydrophobicity of the peptide, $S_{aa}$ is calculated based on amino acid sequence, SSSF is a sum of sequence-specific factors and where constant B and coefficients C1 to C14 are empirically determined. The term $S_{aa}$ is calculated by summing of the product of the number of occurrences for each amino acid in the peptide by the corresponding coefficient ($S_i$) in Table 2.

Example 1

Variations in Separation Selectivity Caused by the Slope of a Solvent Gradient and Development of a Model to Predict S for Peptides The present disclosure provides a sequence-specific model for predicting slopes (S) in the fundamental equation of linear-solvent-strength theory for the reversed-phase HPLC separation of tryptic peptides detected in a typical bottom-up-proteomics experiment. These slopes in-turn control the variation in the separation selectivity observed when physical parameters of chromatographic separation, such as gradient slope, flow rate and column size are altered.

Using the described approach, the retention time shifts associated with variations of gradient slope can be predicted a-priori. The proposed model is based on our original findings for a set synthetic species which postulates that slopes S can be predicted based on peptide length, charge and hydrophobicity.[23] As described herein, this approach is extended using an extensive set of real tryptic peptides, and introduce sequence-specific correction for more accurate prediction of slopes S. A correlation of ~0.95 $R^2$-value between predicted and experimental S-values is demonstrated. This method can yield more accurate estimations of peptide retention in reverse-phase chromatography.

FIG. 1 A,B shows two total-ion count chromatograms of the same test peptide mixture at two different gradient slopes of 0.75 and 0.1875% acetonitrile per minute. 255 tryptic peptides originating from human proteins in the test protein mixture (plus the autolytic species from trypsin) were confidently identified in these two runs, representing a typical nano-RP-LC MS run of moderate complexity. An example of reversal in retention order is highlighted in FIG. 1. While at a steeper gradient in FIG. 1A NECFLQHKDDNPNLPR (SEQ ID NO:1) (human albumin) elutes prior to VATVSLPR (SEQ ID NO:2) (porcine trypsin), the shallower gradient causes the

TABLE 1

Synthetic "S-calibrating peptides".

| Internal index number | Sequence (charge, length) | SEQ ID NO: | Mol. Weight (Da) | Calculated Hydrophobicity Index (HI)** | Slope |
|---|---|---|---|---|---|
| 1 (P2*) | LGGGGGGDFR (+2, 10) | 3 | 891.42 | 6.03 | 28.2 |
| 2 (P3*) | LLGGGGDFR (+2, 9) | 4 | 890.46 | 8.81 | 24.76 |
| 3 (P4*) | LLLGGDFR (+2, 8) | 5 | 889.50 | 13.33 | 21.46 |
| 4 (P5*) | LLLLDFR (+2, 7) | 6 | 888.54 | 19.46 | 21.78 |
| 5 (P6*) | LLLLLDFR (+2, 8) | 7 | 1001.63 | 22.44 | 22.76 |
| 6 | LASAADFR (+2, 8) | 8 | 849.46 | 6.47 | 27.07 |
| 7 | LASAAHFR (+3, 8) | 9 | 871.47 | 4.02 | 35.59 |
| 8 | LLSLADFG (+1, 8) | 10 | 834.45 | 16.67 | 19.2 |
| 9 | LAGGGSASSSADAAAFR (+2, 17) | 11 | 1494.71 | 8.71 | 34.8 |
| 10 | LLGGSLSSLHAAFR (+3, 14) | 12 | 1427.79 | 15.11 | 33.81 |
| 11 | LAGGGSASSSAHAAAFR (+3, 17) | 13 | 1516.74 | 5.08 | 44.66 |

*-members of P1-P6 standard peptide mixture for the "hydrophobicity calibration" of RP-HPLC systems;[24]
**-HI =H*0.4954-2.6687;
where H-peptide hydrophobicity calculated using 100A-FA version of SSRCalc (http://hs2.proteome.ca/SSRCalc/SSRCalc33B.html).

TABLE 2

Composition-specific coefficients ($S_i$) for individual amino acids used in the calculation of the term $S_{aa}$ in the SSSCalc model.

| Residue | $S_i$ | $R_c$* |
|---|---|---|
| M | 0.772 | 6.65 |
| I | 0.542 | 8.95 |
| Y | 0.541 | 5.86 |
| W | 0.362 | 13.45 |
| V | 0.357 | 5.64 |
| F | 0.22 | 11.70 |
| P | 0.101 | 2.42 |
| C | 0.074 | 0.70 |
| L | 0.055 | 10.19 |
| Q | −0.168 | 0.21 |
| T | −0.27 | 1.12 |
| S | −0.39 | 0.25 |
| A | −0.417 | 1.49 |
| R | −0.423 | −3.83 |
| N | −0.515 | −0.74 |
| D | −0.552 | 1.06 |
| E | −0.661 | 1.95 |
| K | −0.94 | −4.48 |
| H | −1.187 | −4.50 |
| G | −1.279 | 0.02 |

$R_c$* are retention coefficients for 100 Å-FA SSRcalc model.

switch in retention (1B). This paradoxical situation occurs when peptide affinity to the RP phase changes depending on the gradient can be explained from the point of view of LSS theory. Larger peptide NECFLQHKDDNPNLPR (SEQ ID NO:1) has a larger slope value in the basic LSS theory equation, compared to the shorter peptide VATVSLPR (SEQ ID NO:2), as schematically shown in FIG. 1C. In the case of isocratic elution with acentonitrile concentration below intersection point $\phi_I$, the peptide with lower S-value will elute first. Reversed retention will be observed when acetonitrile concentration is higher than $\phi_I$. A recent monograph by Snyder & Dolan[22] gives a detailed explanation of the connections between isocratic and gradient elution modes in RP HPLC. In the case shown in FIG. 1, the application of shallower gradient leads to the situation when most of the separation of two species occurs with $\phi<\phi_I$, favoring relatively low retention of peptide with smaller S (VATVSLPR (SEQ ID NO:2)). The situation is reversed when a steeper gradient is applied: most of the separation happens at $\phi>\phi_I$ causing lower retention of peptide with higher S (NECFLQHKDDNPNLPR (SEQ ID NO:1)). The relative change in retention of these two species can be predicted based on the original assumption of Snyder and co-workers: indeed the heavier NECFLQHKDDNPNLPR (SEQ ID NO:1) should exhibit a higher S. In general, however, this rule does not hold up. As shown in Example 4, a prediction model based solely on the MW of separated species does not provide accurate and reliable results.

The data shown in FIG. 1 presents a case of reversal in separation selectivity. For this to happen two peptides should possess close hydrophobicities but substantially different S-values. In most of the cases elution order will remain the same and only relative retention will be altered. This will result in deviations from the expected perfect correlations between retention times recorded at different gradient slopes. Thus, in the present case 2-times and 4-times increase in the gradient slope results in 0.998 and 0.993 $R^2$-value of $t_R$ vs. $t_R$ correlations as shown in FIG. 2A for the 255 observed peptides. The degree of variation in separation selectivity will conceivably depend on the choice of member peptides: if separated compounds will have identical or systematically changing S-values the correlations will remain perfect. Diverse sets of tryptic peptides typical for proteomic experiments normally produce correlations similar to that shown in FIG. 2A.

Inability to control or adjust for such variations will affect the efficiency of proteomic procedures, which employ retention time as one of the parameters in data acquisition or analysis. For example, in scheduled MRM (SRM) protocols, particular retention time windows are used to perform an MS experiment to monitor specific transition (parent-daughter ions) pairs. When transferring the LC method from a discovery to the method development phase, the slope of the gradient is often altered. This will have negative consequences on the accuracy of defining retention time intervals specified for MRM (SRM) transitions.

As shown in Example 3, retention time shifts associated with variations in gradient slope can be expressed in acetonitrile percentage units. For a 4-times difference in a gradient slope this shift may reach as high as 2.5% of acetonitrile. This would amount to a retention time error of 13.3 min if the retention observed at 0.75% gradient were used for the assignment of a MRM window at a 0.1875% gradient. This is a worst-case scenario, where peptides with extreme S-values are used to assign the predicted retention of their respective counterparts. Another popular application suggests the use of peptide retention prediction for filtering false positive MS/MS identifications.[25] Both the accuracy of prediction and margins of retention time error will be affected by the differences in the chromatographic conditions used. FIG. 2B shows the performance of the formic acid version of SSRCalc retention prediction model for identical lists of peptides detected in the experiments with 3 different gradient slopes. $R^2$-value correlations between calculated hydrophobicity and retention time vary within a 0.962-0.955 range. Such subtle differences could be considered non-essential. Moreover, this might not visible at all in case for a low-accuracy prediction model. However, it will become a problem when routine applications of retention prediction will reach 0.98-0.99 $R^2$-value correlations.

Example 2

Effect of S-values on Peptide Retention (Theoretical Considerations): Measuring S-values for Peptides The widely accepted theoretical description of retention behavior of peptidic compounds is based on LSS theory as detailed by Stadalius et al.[17] The retention time of a peptide under a gradient elution conditions is given as:

$$t_g = t_G/(S\Delta\phi)\log(2.3k_0 t_0(S\Delta\phi/t_G)+1) + t_0 + t_D; \quad (2)$$

where $t_0$ is the column dead-time; $t_D$ is the dwell-time of the gradient system; $t_G$ is the gradient time for the gradient of $\Delta\phi$. While Eqn. 2 is absolutely instrumental as a theoretical description of peptide behavior in RP-HPLC systems, the practical application of it for calculating retention times of peptides is limited. It requires precise measurements of the parameters of the RP HPLC system ($t_0$, $t_D$), as well as knowing the coefficients S and $k_0$ for a particular peptide. This is very rarely the case. Previously, the calculation of peptide separation selectivity based on Eqn. 2 wasn't generally applied in proteomics as: there are no accurate models to predict the S and $k_0$ values for peptides; the measurements of $t_0$ and $t_D$ for nano-flow systems is very complicated; and the reproducibility of the gradients in nano (micro)-flow mode is very hard to achieve.

Conversely, this equation is often employed for a reverse task: to estimate the coefficients S or $k_0$ using experimental retention times measured at different chromatographic conditions in a gradient separation mode. This approach was used to determine S and $k_0$ values for a number of protein and peptides[17, 19-21] and in proteomic experiments.[26] It should be noted, however, that analytical solution of this equation for several different LC conditions (gradients, flow-rates) is obtained by applying numerical multi-parameter fitting algorithms and may result in insufficiently correct calculations.

Accordingly, for the determination of S-values of the set of synthetic peptides we used an isocratic elution procedure, despite it being extremely labor intense.[23] Isocratic measurements consist of determining retention times of peptides at several constant acetonitrile concentrations and plotting experimental Eqn. 1 for each peptide. The resulting dependencies of log k vs. $\phi$ exhibited a very high degree of correlation (0.995-0.999) leaving less ambiguity in determining slopes S.[23] The same measurements for a RP-HPLC system with formic acid as the ion-pairing modifier were performed for the set synthetic peptides shown in Table 1.

Example 3

Measuring S-values for Tryptic Digests in Nano-RP HPLC Systems

There are two distinctly different ways for measuring S-values of peptides: under isocratic conditions or under gradient conditions. The throughput of these measurements will be strongly affected by the type of the detection technique used. When experiments are done with UV detection, the following is true: a) isocratic measurements are more precise, but labor intense and require experiments using purified peptide sample; and b) the determination under the gradient conditions can be done for more complex samples with non-overlapped peaks (but not for the digests typical for proteomic measurements). When the measurements are performed with MS detection the following is correct: a) isocratic measurements are still time consuming and can be effected by the precision of eluent delivery if nano-flow mode is used; and b) the chromatographic profiles of co-eluting peptides in gradient mode can be easily detected thank to the superior resolution power of modern mass spectrometers. Therefore, retention data for hundreds of species can be easily obtained for various gradient conditions.

These two ways of measurement have been combined to provide a highly accurate and fast way of determining S for an extensive sets of peptides (see FIG. 3). First, precise isocratic measurement of S is performed in normal flow conditions with UV detection for a set of synthetic "S-calibrating" peptides. Similar to the previously described peptide mixture P1-P6 designed to cover wide range of hydrophobicities, these peptides were chosen to cover wide range of S-values (Table 1). Second—a tryptic digest of the bovine proteins mixture (model mixture) is spiked with the "S-calibrating" peptides and run under two different gradient slopes in nano-flow RP-HPLC MS: 0.75 and 0.1875% acetonitrile per minute in our case. Third—retention times are assigned for all identified species. Fourth—retention time shifts in acetonitrile percentage (ACN %) units relative to P3 were determined as:

$$\Delta = (t_{R\ 0.75} - t_{RP3\ 0.75})*0.75 - (t_{R\ 0.1875} - t_{RP3\ 0.1875})*0.1875 \quad (3);$$

where $t_{R\ 0.75}$ and $t_{RP3\ 0.75}$ are the retention times of any peptide and reference P3 at 0.75% per minute, and $t_{R\ 0.1875}$ and $t_{RP3\ 0.1875}$ are the retention times of any peptide and reference P3 at 0.1875% acetonitrile per minute gradient, respectively. Fifth—an experimental $\Delta$ vs. S curve was plotted for S-calibrating peptides (FIG. 3). Sixth—S values were extracted from this dependence for all peptides observed in both nano-RP-HPLC MS runs by extrapolation of experimental $\Delta$ on this plot.

This procedure is based on the assumption that S-values are identical for both normal and nano-flow systems employing the same mobile and stationary phases. The value of $\Delta$ represents how relative retention (expressed in acetonitrile percentage) shifts upon transfer from a shallow (0.1875%) to a steep (0.75%) gradient. A steeper gradient causes negative relative shift in retention for peptides with larger S, and positive shifts ($\Delta$-values) for peptides with lower S. The slope value for the reference peptide P3 was measured to be 24.76 (Table 1). Therefore negative $\Delta$ will be characteristic for peptides with S>24.76 and positive for S<24.76 as shown in FIG. 3.

S and $\Delta$ are related by a reciprocal function derived from Equation 2 (as detailed in Example 8):

$$\Delta = 100*\log(G0/G1)*(1/S - 1/S\_P3) \quad (4);$$

where $G_0$ and $G_1$ are the gradient slopes, and A is a constant related to the system parameters $t_0$, $t_D$, and the observed retention times of the reference peptide (in this case P3) under gradient slopes $G_0$ and $G_1$. For a four-times gradient slope ratio, the numerator in this expression 100*log(4) reduces to a constant 60.206. Fitting the observed $\Delta$ and measured S values for the 11 S-calibrating peptides, we found the optimum value of A=2.431 gave an $R^2$~0.98, but the function diverged significantly from the data for S-values >35, giving an RSS (residual sum of squares) of 0.32. Conversely, a natural-log fit to the same data gave a slightly reduced $R^2$~0.97, but a significantly smoother fit across all data points (RSS of 0.15). Accordingly, this form was used for our fit function for the determination of slope values: $\Delta = -2.6816*\ln(S) + 8.7157$ or $S = 25.846*\exp(-0.3619*\Delta)$.

The P1-P6 set of calibrating peptides was used to calibrate RP-LC system in hydrophobicity scale. The plot in FIG. 3 shows the calibrating of chromatographic systems in a S-scale. The experimental S values for all 301 species detected in LC-MS runs of model peptide mixture are provided in Table 3. It is interesting to note that they span an interval from 18.2 to 54, while S measured for calibrating peptide values in Table 1 from 19.2 to 44.6, showing very good coverage. The peptides P2-P6 from the mixture used for hydrophobicity calibration are part of the S-calibrating set of peptides shown in Table 1. However, they cover a very limited interval of S from 21.5 to 28.2, so their usefulness for the determination of S-values is limited. Peptides 6-11 identified in Table 1 would therefore provide good coverage for experiments for determining S-values for unknown peptides.

Example 4

Parameters Affecting Slope Values for Peptidic Compounds

The present analysis of experimentally derived slopes S, confirmed the effect of major molecular descriptors on S-values. Previous work was done for a set of synthetic species and trifluoroacetic acid as an ion-pairing modifier.[23] The present analysis provided data for a real proteomic sample with formic acid and confirmed the following rules regarding S as shown in Table 3. Peptides exhibiting the lowest S-values are all short relatively hydrophobic species carrying lowest possible number of charged groups (2) for tryptic peptides—DLLFK (SEQ ID NO:226) (18.2), DLLFR (SEQ ID NO:207) (18.4), FCLFK (SEQ ID NO:64) (21.7), DSALGFLR (SEQ ID NO:252) (21.8), EDLIWK (SEQ ID NO:187) (21.9). This is consistent with the finding that S increases with peptide length (N), charge (Z), and decreases with hydrophobicity (HI) for short peptides. Highest S-values are characteristic for long peptides carrying multiple positively-charged groups at acidic pH plus extremely hydrophilic species. The list of five analytes with the highest S-values shown in Table 3 includes the two former and three latter ones: GEGENQCACSSR (SEQ ID NO:292) (54.1), GEGENQCACSSR (SEQ ID NO:292) (51.7), DGTRKPVTDAENCHLAR (SEQ ID NO:155) (50.4), KPVTEAQSCHLAVAPNHAWSR (SEQ ID NO:46) (49.5), VTGENDKYR (SEQ ID NO:294) (49.0). DGTRKPVTDAENCHLAR (SEQ ID NO:155) and KPVTEAQSCHLAVAPNHAWSR (SEQ ID NO:46) are moderately hydrophobic, both carrying 5 positively charges groups, long peptides: 17 and 22 residues, respectively. GEGENQCACSSR (SEQ ID NO:292), GEGENQCACSSR (SEQ ID NO:292), VTGENDKYR (SEQ ID NO:294) are moderately sized, hydrophilic species. The latter subset of peptides was excluded from our original modeling of S-values. Since anomalously high slopes were expected for them, previously only molecules with HI>10 were used, i.e. eluting from reversed phase columns at acetonitrile concentrations above 10%.[23] The set of peptides used in this study included all 301 species detected in respective LC-MS run, making it more realistic and challenging.

Example 5

Sequence-specific Slope Calculator (SSSC) Model

Figure 4:
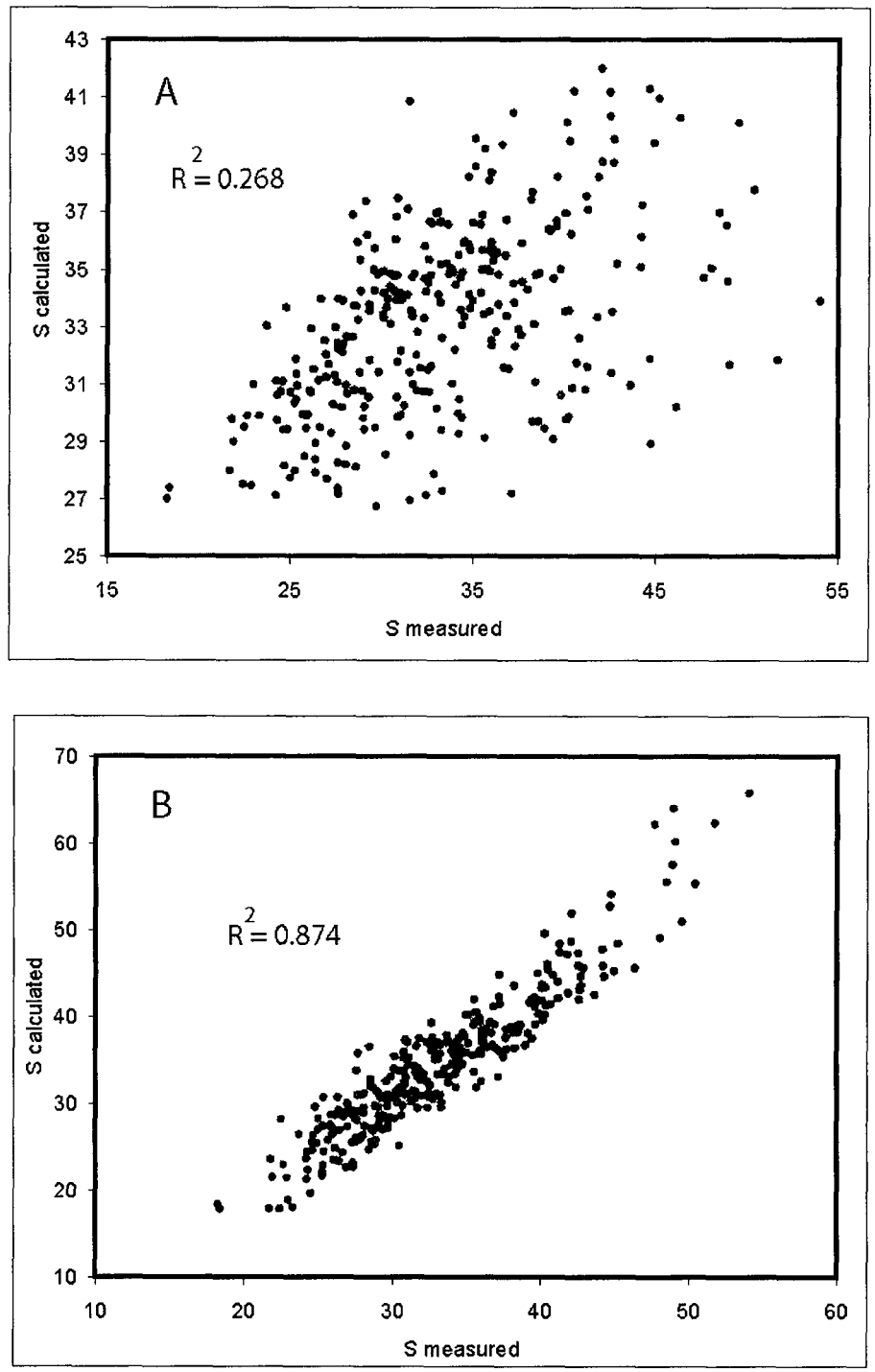
Figure 4:
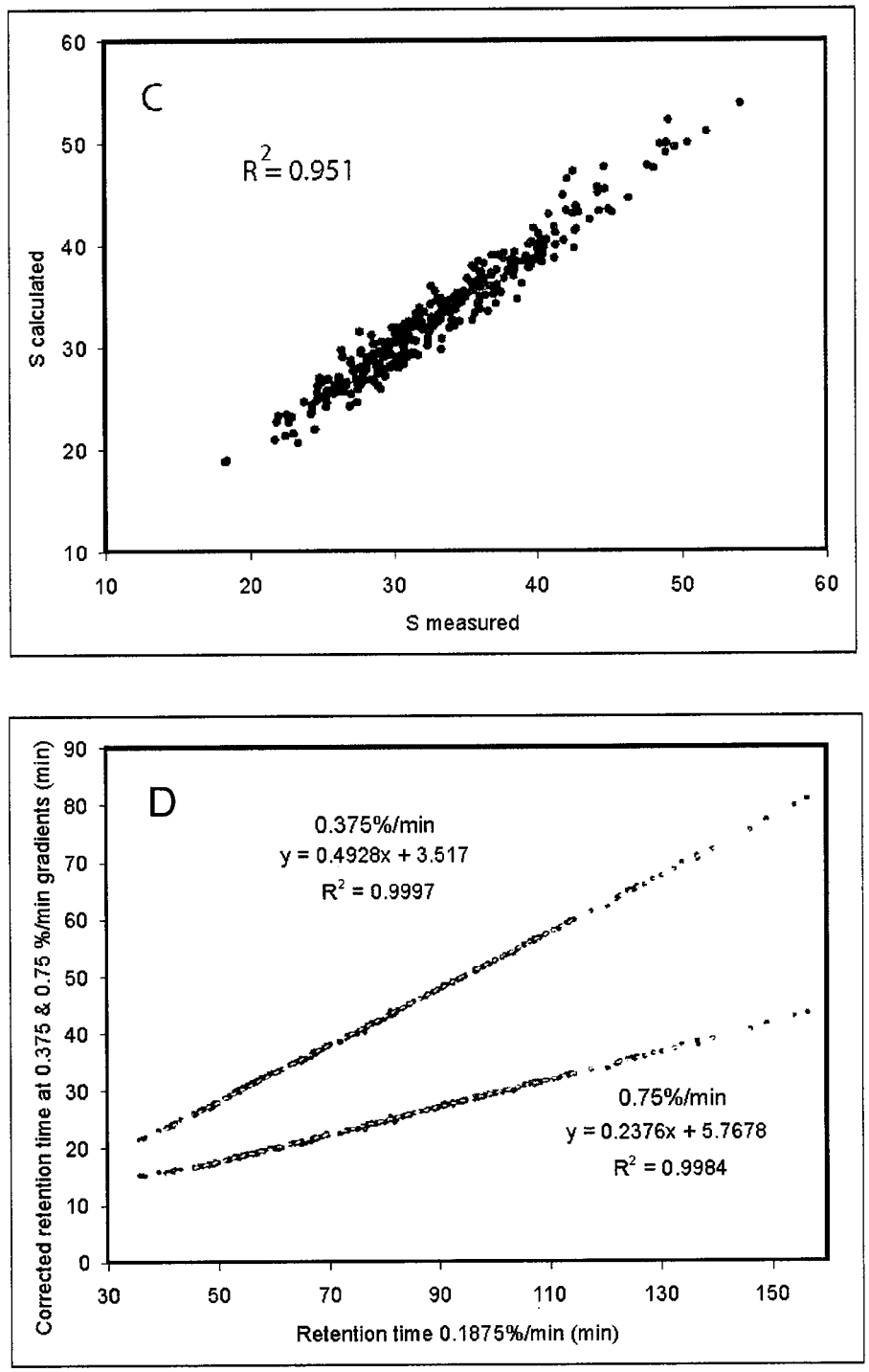

The original assumption made by Stadalius et al.[17] that S values can be described as a function of molecular weight: $S=a*MW^b$ was tested. FIG. 4A shows the best-fit correlation $S=3.9*MW^{0.3}$. The $R^2$-value of 0.268 clearly shows the inapplicability of this approach. Initially the direct relationship between S and MW was found for a limited group of molecules within a very wide 600-14000 Da mass range. It is conceivable that for a random set of peptides the molecule length, number of positively charged groups, number of hydrophobic contact sites will increase with molecular weight. When extended sets of molecules with rather limited molecular weights are considered (like typical tryptic peptides), increase in molecular weight does not necessarily coincide with an increase in N or Z. In other words, the addition of an extra residue to a small peptide chain causes a much more profound and an often unexpected effect on the properties of the molecule, including shifting the S-value.

The previously described approach, where S is postulated to be a function of Z, N and HI with a range of power, reciprocal and cross-term coefficients (NZHI model) was applied to the current data set, with the introduction of an additional cross-term $C13*Z*N*HI^{C14}$. These coefficients were optimized against the 301 observed peptide slope values using the random-walk through parameter spaced described elsewhere. It gives a best-fit 0.874 correlation for the equation as shown in FIG. 4b:

$$S=-66.8000*Z^{-03.7906}+19.5332*N^{+00.3540}-36.0981*HI^{+00.2269}+08.9598/Z+00.3041/N-00.0838/HI-00.9632*Z*N+00.2277*Z*HI+00.0111*N*HI+01.1761*Z*N*HI^{-00.1196}+041.8320 \quad (5)$$

Compared to the 0.97 $R^2$-value for the set of synthetic peptides, this represents a significant decrease in the model accuracy. This was caused by inclusion of peptides with low hydrophobicities into the current model set, and the overall random character of the molecular composition of detected species. The 37 model peptides studied before all had related structures and consisted of similar amino acids: Leu, Ala, Val, His, Ser, Asp, Gly, Phe, Arg. Real proteomic samples contain a much more diverse set of peptides and represent all naturally occurring residues.

Accordingly, a model for the prediction of slope S was developed as described herein that was both composition and sequence specific. Similar to optimization of the SSRCalc algorithm for hydrophobicity calculation, composition- and sequence-specific features were established using a semi-empirical approach. First, a list of peptides with the largest positive/negative errors in prediction S using NZHI model were analyzed. Following these initial observations, possible corrections were suggested, introduced and accepted if resulting correlation showed improvements. Thus, in the list of 20 peptides with highest positive deviations from predicted S following optimization of Eqn. 5 only one contained single Gly residue. Conversely, 20 peptides with largest negative deviations contained all together 27 Gly. This behavior is consistent with unique properties of glycine being amino acid with smallest side chain. This provides additional flexibility to the Gly-containing peptides, decrease respective contact area of the molecule in random-coil conformation and as consequence decrease S-value. This clearly shows the necessity to add correction factors related to peptide composition. Composition-dependent features were introduced similar to additive retention prediction models through the assignment of additional coefficients ($S_i$) for each constituent amino acid. Optimized $S_i$ values are shown in Table 2. As expected the highest negative contribution among all amino acids was found for Gly (−1.28).

Originally it was expected that proline would have an effect opposite to that of glycine. It has exceptional conformational rigidity compared to the other residues, which was expected to increase contact area of interaction between a peptide and a stationary phase. Contrary to this expectation, proline showed no effect on S values ($S_{Pro}=0.1$). Among other conclusions regarding the compositional effects is distinctive positive effect of most of the residues of high and moderate hydrophobicity (Table 2). These residues already contribute to a calculated S-value through the overall hydrophobicity (HI) of a peptide. However clearly visible trend of correlation between $R_c$ and $S_i$ suggests a different character of contribution to S-value of hydrophobicities of the residues on macroscopic (HI of whole peptide) and microscopic (individual residue) levels.

Following the optimization of the composition's effects, a few sequence specific features became visible. First, peptides with uniform distribution of hydrophobic residues mostly exhibited positive deviations in S compared to their calculated values. Conversely, when the most hydrophobic residues within a peptide chain are clustered together leads to lower slope values. A typical example of the former is the LLGSLSLDAFR (SEQ ID NO:30) peptide shown in Table 3. It contains 5 extremely hydrophobic Leu and Phe, which positioned uniformly starting from N-terminal and finishing at second to last position. NYELLCGDNTRK (SEQ ID NO:283) shows the opposite example, with a hydrophobic stretch of residues YELL located close to N-terminus.

Another interesting example when peptides show negative deviations from calculated S values was observed for the species featuring neighboring acidic (D, E) and basic (K, R, H) residues. For example VHKECCHGDLLECADDR (SEQ ID NO:296) fragment from bovine albumin has two such combinations: [KE] and [DR]. It is 17 residues long, has moderate hydrophobicity and should carry 5 positively charged groups at acidic pH. But yet it has S~42 compared to the (described above) similarly sized and charged peptides DGTRKPVTDAENCHLAR (SEQ ID NO:155) and KPVTEAQSCHLAVAPNHAWSR (SEQ ID NO:46), which have S~49-50. This effect is explained by the possible formation of a "salt bridge" between two neighboring residues, which reduces the effective positive charge of Lys and Arg and leads to a decrease in S-value. Presence of positively charged groups involved in ion-pairing interactions on both termini is a characteristic feature of tryptic peptides. It increases the effective contact area and provides conditions for interaction of whole peptide chain with the stationary phase. Removal or decreasing the effective charge on one of termini could provide significant effect on the retention mechanism, orientation of the peptide chain upon the interaction with stationary phase and consequently S-value as in case of VHKECCHGDLLECADDR (SEQ ID NO:296).

Accordingly, an improved model for calculating S was developed that introduced a number of sequence-specific corrections in the model to reflect the effects described above. The Sequence Specific Slope Calculator model took the form of:

$$S=C1*Z^{C2}+C3*N^{C4}+C5*HI^{C6}+C7/Z+C8/N+C9/HI+C10*ZN+C11*ZHI+C12*NH/+C13*Z*N*HI^{C14}+B+S_{aa}+SSSF;$$

where for each peptide N is a peptide length, Z is a peptide charge, HI is hydrophobicity of the peptide, $S_{aa}$ is calculated based on amino acid sequence SSSF is a sum of sequence-specific factors and where constant B and coefficients C1 to C14 are empirically determined.

The term $S_{aa}$ is calculated by summing of the product of the number of occurrences for each amino acid in the peptide by the corresponding coefficient ($S_i$) in Table 2.

The term SSSF is calculated based on summing factors related to 1) the distribution of hydrophobic amino acids (L, I, F, W, Y, V, M) within the peptide chain wherein uniform distribution of these residues increases S; and 2) the positioning of acidic amino acids (E, D) within the peptide chain adjacent to the residues carrying positively charged amino groups at the pH of the eluent (R, K, H, N-terminus) wherein the presence of neighboring acidic amino acids and positively charged amino groups decreases the value of S.

An exemplary means of performing the calculation of S using the Sequence Specific Slope Calculator model is set out in FIG. 5. As set out in FIG. 5, the term SSSF can be calculated as Distmax*SF1+Globe1.

Resulting correlation for Sequence Specific Slope Calculator model improved to ~0.95-value, when composition and sequence-specific effects were taken into account (FIG. 4c). The resulting correlation was obtained by re-iterative optimization of both the NZHI and sequence-specific portions of the model. To test its applicability to the independent data set S-values and respective retention time corrections were calculated for 255 tryptic species from human proteins shown in FIG. 2a. Following retention time correction, the correlation improved from 0.9983 to 0.9997 for a 2-× difference in the gradient slope, and from 0.993 to 0.9984 for 4-× difference in the gradient slope.

The present results clearly demonstrate that sequence specific features are important for determining the slopes in the basic equation of LSS for a peptide. Furthermore, the results demonstrate that incorporation of sequence specific features into a model for the slope S improves the prediction and can be used to improve the estimation of retention times of peptides during reversed phase chromatography and accordingly the isolation or separation of peptides.

Example 7

Retention Models

Building a comprehensive model to describe behavior of peptides in RP HPLC systems is equivalent to precise prediction of coefficients $k_0$ and S in Eqn. 1. Once determined, they can be used for peptide retention prediction in isocratic (Eqn. 1) and gradient (Eqn. 2) separation modes. In practice, however most of the retention prediction algorithms were developed for gradient separation mode when experimental peptide retention correlates essentially with concentration of organic solvent φ, which correspond to particular retention coefficient of any given peptide. Thus, the present applicants have used $k_0=10$ to normalize peptide retention and use acetonitrile percentage as a measure of hydrophobicity.[24] There is a correlation between predicted hydrophobicity and $k_0$: peptides with higher hydrophobicity typically show higher $k_0$ values. However without knowing the rules that control S it hard to justify this approach: it is hard to believe that the model to predict $k_0$ can be viable for prediction of retention times. Accordingly, the acetonitrile percentage scale can be used to express peptide hydrophobicity. When an alteration in the gradient slope has to be taken into account, the respective shifts in relative peptide retention can be expressed in the acetonitrile percentage as well. These shifts can be applied to the calculated HI values providing optimal performance of retention prediction models.

Example 8

Derivation of Δ as a Function of S

We define "Δ" as the difference in peptide ACN-concentrations, referenced against the calibration peptide P3 (LLGGGGDFR (SEQ ID NO:4)); P3 will thus have a Δ of 0:

$$\Delta = G0*(RT\_G0-RT\_P3G0)-G1*(RT\_G1-RT\_P3G1)$$

In order to relate these measured Δ values back to computed S slope values, we start with a slightly modified form of the basic equation for retention time:

$$RT=t0+TD+100*\log 10(0.023*k0*t0*S*G+1)/(S*G)$$

where G is in units of percentage (0-100) rather than normalized (0-1), giving the 100 outside the log function and the 0.023 constant inside the log term. The product term in the log function is >>1 so we can remove the "+1". For our experimental system, RT_P3G0 and RT_P3G1 are measured constants and can be factored out as $$W=G0*RT\_P3G0-G1*RT\_P3G1$$

and the equation simplifies to:

$$\Delta=G0*RT0-G1*RT1-W$$

A further simplification is that since we are measuring the difference for a peptide between two different gradient-slope values, the term 0.023*k0*t0 is also a constant for each peptide; we group these into the constant A and get:

$$\Delta=G0*(t0+TD)+100*\log(A*G0*S)/S-G1*(t0+TD)-100*\log(A*G1*S)/S-W$$

If we assume that both runs were done on the same separation system configuration, TD becomes a constant across both experiments and we can get another constant:

$$L=(G0-G1)*(t0+TD)$$

and Δ is further reduced to:

$$\Delta=(L-W)+(100/S)*(\log(A*G0*S)-\log(A*G1*S))$$

The log-subtraction term then simplifies the difference term to a ratio of log(G0/G1), leaving us with:

$$\Delta+(W-L)=100*\log(G0/G1)/S$$

As we defined at the start, Δ has a value of zero for the peptide P3, giving a substitution for the constant (W−L) of:

$$W-L=100*\log(G0/G1)/S\_P3$$

We then substitute this back into the previous equation:

$$\Delta+100*\log(G0/G1)/S\_P3=100*\log(G0/G1)/S$$

or the final form of:

$$\Delta=100*\log(G0/G1)*(1/S-1/S\_P3)$$

TABLE 3

Experimental and Predicted Values of S.

| Charge | Length | H | Peptide Sequence | Seq ID NO: | Slope (experimental) | Slope predicted (SSSC) | Slope predicted (NZHI model) |
|---|---|---|---|---|---|---|---|
| 2 | 5 | 2.66 | IETMR | 14 | 37.108 | 34.344 | 33.164 |
| 2 | 11 | 17.94 | WCTISQPEWFK | 15 | 30.438 | 29.073 | 25.147 |
| 2 | 6 | 3.82 | VYCDMK | 16 | 35.652 | 33.413 | 31.878 |
| 2 | 13 | 10.64 | LESDVSTQMEYCR | 17 | 35.968 | 34.957 | 32.583 |
| 3 | 6 | 6.71 | WYSMKK | 18 | 33.268 | 29.83 | 29.605 |
| 5 | 22 | 11.35 | APVDAFKECHLAQVPSHAVVAR | 19 | 46.264 | 44.659 | 45.676 |
| 3 | 7 | 4.1 | LSQKFPK | 20 | 38.913 | 36.316 | 36.738 |
| 2 | 7 | 11.31 | YLYEIAR | 21 | 27.362 | 24.644 | 22.692 |
| 3 | 8 | 2.9 | KVIEQVQR | 22 | 43.582 | 42.572 | 42.582 |
| 2 | 6 | 4.49 | TPIAVR | 23 | 33.313 | 30.883 | 30.173 |
| 3 | 7 | 3.8 | RTPIAVR | 24 | 39.365 | 37.836 | 37.549 |
| 2 | 7 | 19.46 | LLLLDFR | 6 | 23.297 | 20.693 | 18.064 |
| 2 | 11 | 6.39 | QFVSSSTTVNR | 25 | 37.462 | 35.42 | 35.388 |
| 2 | 7 | 3.06 | VIEQVQR | 26 | 38.258 | 37.354 | 36.424 |
| 2 | 8 | 20.03 | LLSLLDFR | 27 | 24.464 | 21.979 | 19.68 |
| 2 | 9 | 16.87 | LLIEMEDWK | 28 | 26.865 | 24.256 | 22.626 |
| 2 | 8 | 12.99 | FPTIPLSR | 29 | 27.325 | 26.936 | 23.214 |
| 2 | 11 | 18.98 | LLGSLSLDAFR | 30 | 28.402 | 26.867 | 24.73 |
| 2 | 11 | 8.75 | ELPDPQESIQR | 31 | 34.299 | 33.791 | 31.925 |
| 2 | 12 | 12.61 | FFSASCVPCIDR | 32 | 32.333 | 30.364 | 29.575 |
| 2 | 8 | 10.42 | IRPYFPEQ | 33 | 28.791 | 28.044 | 25.335 |
| 3 | 9 | 3.61 | THFSGDVQR | 34 | 42.53 | 39.809 | 42.061 |
| 2 | 12 | 6.72 | YICDNQDTISSK | 35 | 37.666 | 36.819 | 36.27 |
| 2 | 12 | 8.47 | EYEATLEECCAK | 36 | 35.459 | 32.656 | 33.69 |
| 3 | 14 | 9.93 | LYKELPDPQESIQR | 37 | 39.098 | 38.538 | 38.149 |
| 2 | 4 | 9.15 | WQWR | 38 | 22.398 | 21.364 | 17.895 |
| 3 | 10 | 7.26 | LCENIAGHLK | 39 | 37.285 | 35.543 | 36.036 |
| 5 | 21 | 11.05 | KKEEAPSLRPVPPPISGGGYR | 40 | 44.873 | 43.56 | 45.28 |
| 4 | 13 | 3.86 | KPVTDAENCHLAR | 41 | 48.023 | 47.617 | 49.132 |
| 2 | 12 | 10.81 | EPISVSSQQMLK | 42 | 33.2 | 32.792 | 31.105 |
| 2 | 12 | 19.67 | TVMENFVAFVDK | 43 | 28.849 | 26.267 | 25.843 |
| 2 | 6 | 6.93 | IIPLNR | 44 | 28.596 | 26.676 | 25.604 |
| 2 | 10 | 8.6 | LGAPSITCVR | 45 | 32.708 | 32.742 | 30.612 |
| 5 | 22 | 7.41 | KPVTEAQSCHLAVAPNHAVVSR | 46 | 49.479 | 49.669 | 51.063 |
| 2 | 8 | 2.73 | NTVDSVSR | 47 | 40.092 | 39.104 | 39.7 |
| 3 | 18 | 8.08 | FSTVAGESGSADTVRDPR | 48 | 44.208 | 43.376 | 44.724 |
| 2 | 8 | 15.42 | LLSLADFR | 49 | 25.239 | 24.197 | 21.694 |

TABLE 3-continued

Experimental and Predicted Values of S.

| Charge | Length | H | Peptide Sequence | Seq ID NO: | Slope (experimental) | Slope predicted (SSSC) | Slope predicted (NZHI model) |
|---|---|---|---|---|---|---|---|
| 2 | 8 | 22.44 | LLLLLDFR | 7 | 22.983 | 21.619 | 18.954 |
| 2 | 17 | 8.96 | VVQLEANCQEPCQDTVK | 50 | 39.579 | 40.408 | 39.163 |
| 2 | 12 | 12.67 | TYDSYLGDDYVR | 51 | 31.66 | 29.266 | 29.529 |
| 2 | 15 | 15.97 | LGPNYLQIPVNCPYR | 52 | 32.953 | 34.745 | 31.124 |
| 2 | 5 | 4.75 | IVNLR | 53 | 29.724 | 28.044 | 27.208 |
| 2 | 5 | 8.87 | WDPYK | 54 | 26.36 | 26.128 | 23.385 |
| 3 | 14 | 6.31 | LAGGSASSAHAAFR | 55 | 42.588 | 41.464 | 43.142 |
| 4 | 11 | 6.26 | RLCENIAGHLK | 56 | 40.229 | 39.38 | 40.296 |
| 2 | 13 | 18.69 | TSSSTFQYITLLK | 57 | 29.703 | 28.222 | 27.495 |
| 2 | 9 | 10.39 | YYGYTGAFR | 58 | 29.343 | 27.151 | 27.063 |
| 2 | 5 | 7.78 | WYSMK | 59 | 25.257 | 24.99 | 22.113 |
| 2 | 14 | 12.19 | VPQVSTPTLVEVSR | 60 | 33.745 | 34.556 | 32.446 |
| 3 | 8 | 5.1 | NLNREDFR | 61 | 36.957 | 35.275 | 36.389 |
| 2 | 14 | 18.77 | LLGGSLSSLDAAFR | 62 | 30.604 | 29.336 | 28.688 |
| 2 | 11 | 9.68 | QAYPNLCQLCK | 63 | 32.399 | 32.028 | 30.876 |
| 2 | 5 | 11.97 | FCLFK | 64 | 21.68 | 20.973 | 17.891 |
| 2 | 13 | 6.36 | FNSANDDNVTQVR | 65 | 38.415 | 39.404 | 38.277 |
| 2 | 13 | 16.84 | GLIDEVDQDFTSR | 66 | 30.089 | 28.673 | 28.295 |
| 3 | 19 | 9.65 | DKVVQLEANCQEPCQDTVK | 67 | 42.675 | 41.688 | 43.645 |
| 2 | 5 | 3.21 | LNELR | 68 | 32.443 | 31.635 | 31.254 |
| 2 | 8 | 4.85 | LCQLCAGK | 69 | 34.229 | 32.128 | 33.444 |
| 3 | 16 | 12.38 | RPCFSALTPDETYVPK | 70 | 38.129 | 38.592 | 38.232 |
| 2 | 8 | 12.54 | AFALECIR | 71 | 26.057 | 26.23 | 23.542 |
| 3 | 11 | 7.2 | KLGAPSITCVR | 72 | 37.615 | 38.801 | 37.611 |
| 2 | 5 | 8.42 | IEILR | 73 | 24.216 | 23.491 | 21.314 |
| 2 | 10 | 4.19 | VGDANPALQK | 74 | 38.388 | 37.686 | 38.591 |
| 4 | 17 | 9.57 | LKPDPNTLCDEFKADEK | 75 | 41.815 | 40.537 | 42.791 |
| 4 | 8 | 3.92 | LLHAAHFR | 76 | 39.794 | 38.704 | 40.365 |
| 2 | 6 | 7.81 | NWIQYK | 77 | 26.629 | 26.44 | 24.366 |
| 4 | 8 | 8.05 | LLHLAHFR | 78 | 33.837 | 31.95 | 33.139 |
| 2 | 11 | 14.48 | EPYFGYSGAFK | 79 | 28.713 | 28.269 | 26.921 |
| 4 | 10 | 8.52 | RLDGSLDFKK | 80 | 35.968 | 33.785 | 35.771 |
| 3 | 11 | 5.1 | LAGSASAHAFR | 81 | 40.64 | 40.636 | 41.458 |
| 3 | 13 | 10.16 | LKPDPNTLCDEFK | 82 | 36.757 | 37.376 | 36.74 |
| 2 | 9 | 11.72 | GYLAVVVK | 83 | 27.811 | 26.739 | 25.872 |
| 3 | 8 | 4.02 | LASAAHFR | 9 | 38.571 | 38.452 | 38.968 |

TABLE 3-continued

Experimental and Predicted Values of S.

| Charge | Length | H | Peptide Sequence | Seq ID NO: | Slope (experimental) | Slope predicted (SSSC) | Slope predicted (NZHI model) |
|---|---|---|---|---|---|---|---|
| 3 | 11 | 15.36 | LLGSLSLHAFR | 84 | 31.94 | 31.835 | 30.935 |
| 4 | 16 | 9.23 | NECFLSHKDDSPDLPK | 85 | 41.14 | 38.798 | 42.188 |
| 2 | 9 | 16.25 | DIQYLPILK | 86 | 25.291 | 24.641 | 22.929 |
| 3 | 8 | 6.39 | LAVAAHFR | 87 | 34.392 | 34.259 | 34.028 |
| 4 | 15 | 6.08 | ECHLAQVPSHAVVAR | 88 | 44.148 | 45.203 | 45.929 |
| 2 | 8 | 10.15 | ENFEVLCK | 89 | 27.436 | 26.472 | 25.598 |
| 2 | 16 | 8.12 | GDSVSQGTGLAPGSPR | 90 | 38.571 | 34.786 | 39.172 |
| 2 | 13 | 16.49 | LGEYGFQNALIVR | 91 | 29.764 | 29.382 | 28.465 |
| 3 | 14 | 12.87 | IPSKVDSALYLGSR | 92 | 35.773 | 34.333 | 35.786 |
| 2 | 8 | 8.34 | AEFVEVTK | 93 | 29.046 | 25.917 | 27.612 |
| 4 | 8 | 11.23 | LLHLLHFR | 94 | 31.51 | 30.637 | 30.63 |
| 2 | 9 | 11.36 | IQLEDWNGR | 95 | 27.849 | 27.416 | 26.176 |
| 3 | 8 | 9.43 | LLVAAHFR | 96 | 31.212 | 29.337 | 30.274 |
| 2 | 12 | 6.56 | ETYGDMADCCEK | 97 | 36.36 | 35.173 | 36.544 |
| 2 | 15 | 11.12 | TPCTVTCNIPVVSGK | 98 | 34.721 | 34.506 | 34.563 |
| 4 | 14 | 8.12 | IQALLDKYNEEKPK | 99 | 40.311 | 38.4 | 41.38 |
| 3 | 5 | 8.19 | RWQWR | 100 | 27.269 | 27.842 | 25.511 |
| 3 | 8 | 15.75 | LLSLLHFR | 101 | 28.039 | 27.884 | 26.458 |
| 4 | 10 | 6.14 | FKDLGEEHFK | 102 | 38.336 | 37.049 | 38.994 |
| 2 | 10 | 13.18 | LVNELTEFAK | 103 | 27.906 | 26.847 | 26.321 |
| 3 | 11 | 8.36 | HLVDEPQNLIK | 104 | 35.894 | 34.426 | 36.056 |
| 3 | 13 | 10.76 | KTYDSYLGDDYVR | 105 | 35.968 | 34.826 | 36.199 |
| 2 | 13 | 14.21 | CLMEGAGDVAFVK | 105 | 30.666 | 28.4 | 29.754 |
| 2 | 11 | 14 | SQLQEAPLEWK | 107 | 28.576 | 29.102 | 27.224 |
| 2 | 6 | 6.58 | YLTTLK | 108 | 27.604 | 26.41 | 26.145 |
| 3 | 15 | 15.15 | IHLISTQSTIPYVLR | 109 | 35.386 | 36.393 | 35.622 |
| 2 | 10 | 7.45 | MSTITGPVPR | 110 | 32.509 | 34.27 | 32.159 |
| 2 | 11 | 12.49 | ETTVFENLPEK | 111 | 29.323 | 27.358 | 28.29 |
| 3 | 8 | 16.67 | LLVLLHFR | 112 | 27.548 | 28.046 | 26.157 |
| 3 | 12 | 7.26 | NFSDVHPEYGSR | 113 | 37.948 | 37.615 | 38.923 |
| 3 | 15 | 10.62 | KVPQVSTPTLVEVSR | 114 | 37.64 | 39.29 | 38.61 |
| 4 | 20 | 10.25 | KEEAPSLRPVPPPISGGGYR | 115 | 42.646 | 43.932 | 44.712 |
| 2 | 7 | 11.62 | NIVELMR | 116 | 24.282 | 24.382 | 22.432 |
| 3 | 8 | 11.53 | LLSLAHFR | 117 | 29.303 | 29.774 | 28.581 |
| 2 | 11 | 7.61 | ISQLTNMGPTK | 118 | 33.29 | 33.54 | 33.442 |
| 2 | 12 | 13.67 | ILESGPFVSCVK | 119 | 29.323 | 29.082 | 28.679 |
| 2 | 7 | 4.9 | YQLSVSK | 120 | 31.531 | 32.056 | 31.381 |

TABLE 3-continued

Experimental and Predicted Values of S.

| Charge | Length | H | Peptide Sequence | Seq ID NO: | Slope (experimental) | Slope predicted (SSSC) | Slope predicted (NZHI model) |
|---|---|---|---|---|---|---|---|
| 2 | 14 | 9.52 | LAGGSASSADAAFR | 121 | 34.509 | 34.416 | 35.019 |
| 3 | 13 | 12.67 | ILESGPFVSCVKK | 122 | 34.299 | 34.067 | 34.775 |
| 3 | 14 | 14.82 | VWPHGDYPLIPVGK | 123 | 34.183 | 34 | 34.717 |
| 2 | 9 | 12.96 | VLDALDSIK | 124 | 26.128 | 26.812 | 24.917 |
| 4 | 15 | 9.14 | DNPQTHYYAVAVVKK | 125 | 39.552 | 38.103 | 41.255 |
| 3 | 14 | 15.11 | LLGGSLSSLHAAFR | 12 | 34.021 | 32.682 | 34.584 |
| 3 | 11 | 4.91 | ILNKQQDDFGK | 126 | 40.011 | 39.737 | 41.897 |
| 3 | 8 | 6.82 | LLSAAHFR | 127 | 32.998 | 32.503 | 33.367 |
| 2 | 17 | 17.48 | LLGGGSLSSSLDAAAFR | 128 | 32.333 | 30.97 | 32.571 |
| 3 | 8 | 13.44 | LLVLAHFR | 129 | 28.115 | 28.558 | 27.448 |
| 2 | 7 | 6.36 | LQDTLVR | 130 | 29.045 | 29.45 | 28.589 |
| 2 | 9 | 6.2 | NLSVEDAAR | 131 | 32.289 | 30.194 | 32.537 |
| 2 | 12 | 11.9 | GSNFQLDQLQGR | 132 | 30.314 | 28.018 | 30.14 |
| 2 | 14 | 10.43 | LCALCAGDDQGLDK | 133 | 33.517 | 33.58 | 34.043 |
| 3 | 9 | 10.38 | RAFALECIR | 134 | 31.043 | 31.114 | 31.064 |
| 2 | 13 | 11.83 | CLQDGAGDVAFVK | 135 | 31.382 | 30.687 | 31.504 |
| 3 | 11 | 8.5 | EKYYGYTGAFR | 136 | 34.957 | 35.156 | 35.889 |
| 3 | 13 | 9.62 | YETLISTHESTIR | 137 | 36.09 | 37.388 | 37.273 |
| 3 | 9 | 5.55 | WCAIGHQER | 138 | 35.992 | 35.946 | 37.271 |
| 3 | 12 | 9.75 | LRPVAAEIYGTK | 139 | 34.815 | 35.209 | 35.884 |
| 4 | 12 | 4.5 | LKECCDKPLLEK | 140 | 42.82 | 43.3 | 45.649 |
| 2 | 9 | 7.12 | LNSLTVGPR | 141 | 30.791 | 30.77 | 31.029 |
| 5 | 21 | 8.39 | QEPERNECFLSHKDDSPDLPK | 142 | 45.147 | 43.301 | 48.503 |
| 2 | 8 | 11.37 | SMMEEIMK | 143 | 25.394 | 26.93 | 24.477 |
| 2 | 8 | 3.14 | QNCDQFEK | 144 | 36.657 | 36.057 | 38.187 |
| 4 | 11 | 9.79 | KDMDKVETFLR | 145 | 34.768 | 34.918 | 35.938 |
| 2 | 5 | 8.27 | TFYLK | 146 | 22.874 | 23.194 | 21.495 |
| 2 | 14 | 16.41 | MEDEAESLEDLGFK | 147 | 29.603 | 29.968 | 29.73 |
| 3 | 7 | 6.02 | KNWIQYK | 148 | 31.919 | 32.443 | 32.741 |
| 2 | 12 | 11.38 | TSDANINWNNLK | 149 | 30.109 | 28.964 | 30.584 |
| 3 | 17 | 14.84 | LLGGGSLSSSLHAAAFR | 150 | 35.968 | 35.057 | 37.733 |
| 5 | 14 | 8.64 | KYAAELHLVHWNTK | 151 | 39.205 | 38.984 | 41.688 |
| 4 | 13 | 10.18 | YAAELHLVHWNTK | 152 | 36.188 | 36.28 | 38.044 |
| 4 | 8 | 2.83 | VFEHIGKR | 153 | 41.112 | 41.916 | 44.044 |
| 3 | 10 | 5.94 | LLEACTFHKP | 154 | 36.237 | 36.801 | 38.181 |
| 5 | 17 | 4.01 | DGTRKPVTDAENCHLAR | 155 | 50.359 | 50.116 | 55.375 |

TABLE 3-continued

Experimental and Predicted Values of S.

| Charge | Length | H | Peptide Sequence | Seq ID NO: | Slope (experimental) | Slope predicted (SSSC) | Slope predicted (NZHI model) |
|---|---|---|---|---|---|---|---|
| 3 | 17 | 5.8 | LAGGGSASSSAHAAAFR | 13 | 44.118 | 45.747 | 47.789 |
| 4 | 12 | 6.08 | ALEHKVDLEDYK | 156 | 39.365 | 40.119 | 42.047 |
| 4 | 15 | 8.31 | TSDANINWNNLKDKK | 157 | 39.525 | 38.203 | 42.255 |
| 3 | 7 | 4.5 | LCVLHEK | 158 | 34.16 | 34.876 | 35.752 |
| 2 | 8 | 6.47 | LASAADFR | 8 | 29.663 | 30.57 | 30.311 |
| 2 | 9 | 14.84 | QTALVELLK | 159 | 24.2 | 23.572 | 23.696 |
| 2 | 12 | 10.31 | FLQEIYNSNSQK | 160 | 30.666 | 30.117 | 31.593 |
| 2 | 21 | 16.36 | AAANFFSASCVPCADQSSFPK | 161 | 35.1 | 36.809 | 36.995 |
| 2 | 7 | 5.05 | CLASIAK | 162 | 30.212 | 30.794 | 31.057 |
| 3 | 22 | 9.93 | AIQISYNPDQPSKPNNIESATK | 163 | 42.444 | 47.304 | 45.982 |
| 2 | 11 | 7.63 | LAGSASADAFR | 164 | 32.092 | 33.467 | 33.414 |
| 3 | 11 | 6.23 | LAHEDPDYGLR | 165 | 36.832 | 39.059 | 39.188 |
| 2 | 7 | 5.76 | VDLEDYK | 166 | 28.987 | 29.635 | 29.647 |
| 3 | 14 | 9.55 | ESPQTHYYAVAVVK | 167 | 36.262 | 38.305 | 38.541 |
| 3 | 14 | 11.89 | ETTVFENLPEKADR | 168 | 34.533 | 32.582 | 36.458 |
| 4 | 19 | 10.71 | ECCHGDLLECADDRADLAK | 169 | 40.256 | 38.465 | 43.424 |
| 2 | 12 | 14.76 | CGLVPVLAENYK | 170 | 27.604 | 26.881 | 28.119 |
| 2 | 9 | 10.11 | GGWTVIQNR | 171 | 26.957 | 25.486 | 27.339 |
| 2 | 8 | 9.89 | LDGSLDFK | 172 | 25.689 | 25.626 | 25.859 |
| 3 | 10 | 9.76 | LRDSLFNYQK | 173 | 31.66 | 32.872 | 33.126 |
| 3 | 11 | 14.3 | ESGLYFIRPLK | 174 | 30.232 | 31.929 | 31.401 |
| 4 | 16 | 14.56 | RHPYFYAPELLYYANK | 175 | 35.968 | 37.436 | 38.418 |
| 4 | 15 | 7.5 | IQALLDKYNEEKPKN | 176 | 40.038 | 39.931 | 43.399 |
| 2 | 9 | 4.51 | CCTESLVNR | 177 | 33.998 | 34.633 | 36.059 |
| 2 | 7 | 9.28 | SNLQLLR | 178 | 24.614 | 25.598 | 24.65 |
| 2 | 13 | 14.19 | NLLFNDNTECLAK | 179 | 28.81 | 27.511 | 29.767 |
| 3 | 14 | 11.71 | NTPEKGYLAVAVVK | 180 | 34.392 | 34.274 | 36.593 |
| 2 | 7 | 6.16 | LVTDLTK | 181 | 28.077 | 28.698 | 28.93 |
| 3 | 10 | 11.31 | DTDFKLNELR | 182 | 30.459 | 29.226 | 31.829 |
| 2 | 10 | 7.35 | TSTADYASFK | 183 | 30.833 | 30.651 | 32.306 |
| 2 | 7 | 7.44 | IQALLDK | 184 | 26.395 | 25.695 | 26.932 |
| 2 | 8 | 9.36 | LLSAADFR | 185 | 25.969 | 26.33 | 26.419 |
| 3 | 9 | 7.87 | LFAYPDTHR | 186 | 31.897 | 32.53 | 33.642 |
| 2 | 8 | 10.33 | EDLIWK | 187 | 21.902 | 23.304 | 21.551 |
| 3 | 7 | 4.17 | VFEHIGK | 188 | 34.229 | 34.882 | 36.558 |
| 3 | 12 | 10.51 | QVLLHQQALFGK | 189 | 33.087 | 32.601 | 35.177 |
| 3 | 20 | 17.01 | EGFGHLSPTGNTEFWLGNEK | 190 | 36.558 | 33.559 | 39.419 |

TABLE 3-continued

Experimental and Predicted Values of S.

| Charge | Length | H | Peptide Sequence | Seq ID NO: | Slope (experimental) | Slope predicted (SSSC) | Slope predicted (NZHI model) |
|---|---|---|---|---|---|---|---|
| 2 | 8 | 11.31 | DAQLFIQK | 191 | 24.282 | 23.709 | 24.528 |
| 3 | 20 | 10.38 | QNQVQDNENWNEYSSHLEK | 192 | 40.065 | 41.222 | 43.754 |
| 3 | 12 | 14.7 | LLIEMEDWKGDK | 193 | 30.791 | 29.481 | 32.473 |
| 2 | 11 | 12.32 | ANEGLTWNSLK | 194 | 27.455 | 25.957 | 28.422 |
| 2 | 12 | 10.81 | VVWCAVGPEEQK | 195 | 29.603 | 29.55 | 31.105 |
| 2 | 6 | 2.8 | AMTNLR | 196 | 32.841 | 35.554 | 35.122 |
| 2 | 5 | 2.56 | ENVLR | 197 | 31.531 | 33.416 | 33.55 |
| 2 | 14 | 14.6 | YCGVPGEYWLGNDR | 198 | 29.184 | 27.93 | 30.738 |
| 2 | 7 | 8.55 | SILENLR | 199 | 24.865 | 25.183 | 25.487 |
| 3 | 10 | 3.31 | NLRETAEEVK | 200 | 40.778 | 43.101 | 44.867 |
| 3 | 15 | 14.87 | MKGLIDEVDQDFTSR | 201 | 33.2 | 34.867 | 35.752 |
| 3 | 14 | 10.31 | DNPQTHYYAVAVVK | 202 | 34.815 | 35.528 | 37.78 |
| 2 | 8 | 13.33 | LLLGGDFR | 5 | 22.643 | 22.682 | 22.977 |
| 2 | 6 | 4.75 | SIEDLR | 203 | 28.058 | 29.019 | 29.578 |
| 3 | 10 | 6.46 | HQLYIDETVK | 204 | 34.369 | 35.308 | 37.271 |
| 2 | 8 | 5.04 | DDSPDLPK | 205 | 30.875 | 29.075 | 33.024 |
| 2 | 9 | 5.4 | QSPVDIDTK | 206 | 31.703 | 33.008 | 34.06 |
| 2 | 5 | 11.93 | DLLFR | 207 | 18.36 | 18.955 | 17.922 |
| 3 | 5 | 5.51 | KFWGK | 208 | 27.604 | 26.891 | 29.195 |
| 2 | 15 | 16.15 | ETGWPFCSDEDWNTK | 209 | 29.105 | 30.559 | 31.03 |
| 2 | 8 | 10.17 | DSLFNYQK | 210 | 24.58 | 24.827 | 25.578 |
| 3 | 14 | 10.53 | HSTVFDNLPNPEDR | 211 | 34.439 | 34.258 | 37.576 |
| 4 | 22 | 9.35 | GRQNQVQDNENVVNEYSSHLEK | 212 | 42.444 | 43.145 | 47.38 |
| 3 | 13 | 9.88 | KGSNFQLDQLQGR | 213 | 33.883 | 33.459 | 37.011 |
| 2 | 17 | 8.71 | LAGGGSASSSADAAAFR | 11 | 35.894 | 38.519 | 39.486 |
| 2 | 7 | 7.14 | DQLVDMK | 214 | 25.899 | 25.636 | 27.364 |
| 2 | 18 | 10.82 | DQTVIQNTDGNNNEAWAK | 215 | 34.721 | 34.688 | 38.131 |
| 3 | 13 | 8.03 | AVLKDGPLTGTYR | 216 | 35.435 | 38.055 | 39.143 |
| 2 | 12 | 14.1 | DLEEGIQTLMGR | 217 | 26.684 | 26.617 | 28.529 |
| 2 | 6 | 5.06 | AWSVAR | 218 | 26.993 | 28.802 | 28.91 |
| 2 | 21 | 24.73 | FYTEDGNVVOLVGNNTPIFFIR | 219 | 31.467 | 32.723 | 34.365 |
| 3 | 16 | 14.26 | GAGAFGYFEVTHDITR | 220 | 33.608 | 34.366 | 37.068 |
| 2 | 14 | 8.7 | YNGVFQECCQAEDK | 221 | 32.73 | 32.143 | 36.007 |
| 2 | 7 | 6.98 | GACLLPK | 222 | 25.811 | 25.526 | 27.603 |
| 4 | 15 | 11.18 | DDPHACYSTVFDKLK | 223 | 35.483 | 35.567 | 39.376 |
| 2 | 18 | 15.84 | GEADALNLDGGYIYTAGK | 224 | 31.382 | 29.542 | 34.406 |

TABLE 3-continued

Experimental and Predicted Values of S.

| Charge | Length | H | Peptide Sequence | Seq ID NO: | Slope (experimental) | Slope predicted (SSSC) | Slope predicted (NZHI model) |
|---|---|---|---|---|---|---|---|
| 2 | 9 | 6.84 | DGPLTGTYR | 225 | 28.947 | 28.508 | 31 464 |
| 2 | 5 | 11.32 | DLLFK | 226 | 18.223 | 18.797 | 18.415 |
| 3 | 11 | 5.05 | WCTISTHEANK | 227 | 37.234 | 39.129 | 41.571 |
| 3 | 17 | 11.53 | CACSNHEPYFGYSGAFK | 228 | 35.846 | 36.641 | 39.882 |
| 4 | 24 | 12.57 | KPPDADGCLHADPDLGVLCPTGCK | 229 | 40.448 | 39.915 | 45.531 |
| 2 | 16 | 13.49 | VTALYEGFTVQNEANK | 230 | 30.77 | 32.13 | 33.763 |
| 2 | 10 | 9.72 | VDSALYLGSR | 231 | 27.122 | 27.703 | 29.326 |
| 2 | 6 | 6.42 | INLLQK | 232 | 24.664 | 26.252 | 26.403 |
| 3 | 13 | 10.07 | VVWCAVGPEEQKK | 233 | 33.2 | 34.371 | 36.826 |
| 4 | 15 | 9.16 | HSTVFDNLPNPEDRK | 234 | 36.807 | 37.105 | 41.233 |
| 4 | 11 | 3.48 | HMDGYGSHTFK | 235 | 41.758 | 44.993 | 47.264 |
| 3 | 8 | 5.22 | DLGEEHFK | 236 | 32.597 | 32.467 | 36.142 |
| 2 | 8 | 8.79 | ELLIDNEK | 237 | 25.018 | 25.242 | 27.065 |
| 2 | 8 | 8.47 | LLCLDGTR | 238 | 25.325 | 25.786 | 27.451 |
| 4 | 17 | 3.64 | EEGSVSSGTKQEFHTGK | 239 | 48.449 | 49.97 | 55.606 |
| 3 | 13 | 17.44 | DALLFPSFIHSQK | 240 | 29.523 | 30.526 | 32.624 |
| 2 | 10 | 6.03 | LGGGGGGDFR | 3 | 31.043 | 31.073 | 34.493 |
| 3 | 15 | 5.96 | LAIGEGQQHQLGGAK | 241 | 39.74 | 41.745 | 45.079 |
| 3 | 12 | 12.32 | SLHTLFGDELCK | 242 | 30.438 | 31.161 | 33.794 |
| 2 | 9 | 8.56 | DFPIANGER | 243 | 26.539 | 26.279 | 29.061 |
| 3 | 9 | 8.29 | RLDGSLDFK | 244 | 29.845 | 31.987 | 33.133 |
| 3 | 15 | 12.59 | KYCGVPGEYWLGNDR | 245 | 33.065 | 33.204 | 37.052 |
| 3 | 8 | 2.12 | TSHMDCIK | 246 | 40.393 | 39.215 | 46.072 |
| 2 | 11 | 11.94 | CGLVPVLAENR | 247 | 26.128 | 27.127 | 28.726 |
| 2 | 9 | 7.02 | DNCCILDER | 248 | 28.077 | 28.58 | 31.182 |
| 3 | 12 | 7.95 | KNYELLCGDNTR | 249 | 33.631 | 34.138 | 37.948 |
| 3 | 13 | 10.22 | DDPHACYSTVFDK | 250 | 32.575 | 32.99 | 36.684 |
| 2 | 15 | 14.58 | FDEFFSAGCAPGSPR | 251 | 28.654 | 28.582 | 31.921 |
| 2 | 8 | 12.45 | DSALGFLR | 252 | 21.784 | 22.741 | 23.61 |
| 3 | 14 | 6.74 | QGFGNIATNAEGKK | 253 | 37.184 | 36.22 | 42.366 |
| 3 | 17 | 8.13 | CCAADDKEACFAVEGPK | 254 | 38.207 | 38.083 | 43.616 |
| 2 | 7 | 5.99 | APVDAFK | 255 | 26.378 | 29.1 | 29.228 |
| 2 | 11 | 9.5 | NYELLCGDNTR | 256 | 27.868 | 28.181 | 31.051 |
| 3 | 21 | 16.25 | AVVQDPALKPLALVYGEATSR | 257 | 35.627 | 37.918 | 40.515 |
| 3 | 9 | 11.73 | GNLDDFFHR | 258 | 26.957 | 28.511 | 30.047 |
| 3 | 10 | 4.8 | ECCDKPLLEK | 259 | 35.555 | 37.889 | 40.561 |
| 3 | 19 | 7.03 | AAQKPDVLTTGGGNPVGDK | 260 | 41.223 | 41.271 | 47.461 |

TABLE 3-continued

Experimental and Predicted Values of S.

| Charge | Length | H | Peptide Sequence | Seq ID NO: | Slope (experimental) | Slope predicted (SSSC) | Slope predicted (NZHI model) |
|---|---|---|---|---|---|---|---|
| 2 | 9 | 8.81 | LLGGGGDFR | 4 | 25.846 | 26.257 | 28.759 |
| 3 | 10 | 12.55 | KQTALVELLK | 261 | 27.642 | 29.497 | 30.993 |
| 4 | 12 | 10.04 | RHPEYAVSVLLR | 262 | 32.553 | 36.05 | 36.985 |
| 3 | 10 | 10.98 | NCPDKFCLFK | 263 | 28.518 | 30.367 | 32.08 |
| 3 | 11 | 10.27 | SVDGKEDLIWK | 264 | 30.068 | 31.406 | 34.071 |
| 3 | 12 | 10.33 | KANEGLTWNSLK | 265 | 31.085 | 31.932 | 35.337 |
| 3 | 19 | 13.52 | GDKVTALYEGFTVQNEANK | 266 | 35.1 | 35.334 | 40.286 |
| 4 | 28 | 11.74 | AAQKPDVLTTGGGNPVGDKLNSLTVGPR | 267 | 41.986 | 43.468 | 48.723 |
| 2 | 10 | 12.95 | EDGGGWWVYNR | 268 | 23.696 | 24.732 | 26.485 |
| 3 | 14 | 8.1 | ECCHGDLLECADDR | 269 | 34.957 | 34.965 | 40.283 |
| 3 | 11 | 7.55 | GDKELLIDNEK | 270 | 32.311 | 31.853 | 37.108 |
| 3 | 13 | 9.29 | ANEGLTWNSLKDK | 271 | 32.686 | 32.614 | 37.622 |
| 3 | 12 | 10.36 | CGLVPVLAENRK | 272 | 30.745 | 32.351 | 35.31 |
| 2 | 6 | 5.36 | TGQIFK | 273 | 24.984 | 26.68 | 28.302 |
| 2 | 9 | 6.03 | QDGSVDFGR | 274 | 28.518 | 29.397 | 32.843 |
| 4 | 15 | 2.63 | ESKPPDSSKDECMVK | 275 | 48.845 | 49.146 | 57.604 |
| 2 | 13 | 7.32 | QGFGNIATNAEGK | 276 | 31.595 | 32.159 | 36.665 |
| 3 | 9 | 2.07 | SHCIAEVEK | 277 | 41.223 | 40.069 | 48.438 |
| 6 | 22 | 6.92 | VHKECCHGDLLECADDRADLAK | 278 | 44.599 | 47.738 | 52.788 |
| 4 | 14 | 16.73 | DALLFPSFIHSQKR | 279 | 30.728 | 31.973 | 35.971 |
| 2 | 9 | 7.32 | ALLEMQQTK | 280 | 26.288 | 29.808 | 30.73 |
| 4 | 14 | 7.65 | KANEGLTWNSLKDK | 281 | 35.507 | 36.065 | 42.025 |
| 3 | 12 | 10.18 | DSADGFLKIPSK | 282 | 30.089 | 30.532 | 35.474 |
| 3 | 12 | 8.27 | NYELLCGDNTRK | 283 | 31.767 | 33.924 | 37.534 |
| 3 | 13 | 9.8 | MVLETFGGDGHAR | 284 | 31.001 | 32.593 | 37.09 |
| 3 | 11 | 0.9 | ARPATATVGQK | 285 | 51.675 | 51.198 | 62.361 |
| 2 | 12 | 12.53 | SFQLFGSPPGQR | 286 | 24.764 | 27.056 | 29.636 |
| 4 | 21 | 10.88 | SEDGSDCGDADFDWHHTFPSR | 287 | 37.158 | 37.626 | 44.872 |
| 4 | 15 | 11.22 | DKPDNFQLFQSPHGK | 288 | 32.597 | 32.952 | 39.346 |
| 2 | 19 | 12.83 | EDGSDPPSGDFLTEGGGVR | 289 | 30.812 | 31.354 | 37.363 |
| 2 | 9 | 0.82 | ECVPNSNER | 290 | 44.66 | 45.573 | 54.222 |
| 3 | 5 | 8.96 | DKDDFFTR | 291 | 25.342 | 26.94 | 30.736 |
| 2 | 12 | 0.48 | GEGENQCACSSR | 292 | 54.005 | 53.955 | 65.834 |
| 3 | 9 | 7.72 | KENFEVLCK | 293 | 27.567 | 31.591 | 33.832 |
| 3 | 9 | 0.72 | VTGENDKYR | 294 | 49.044 | 52.296 | 60.295 |
| 2 | 7 | 0.82 | VLNEEQR | 295 | 40.229 | 40.591 | 49.629 |

TABLE 3-continued

Experimental and Predicted Values of S.

| Charge | Length | H | Peptide Sequence | Seq ID NO: | Slope (experimental) | Slope predicted (SSSC) | Slope predicted (NZHI model) |
|---|---|---|---|---|---|---|---|
| 5 | 17 | 4.99 | VHKECCHGDLLECADDR | 296 | 42.014 | 46.57 | 51.979 |
| 2 | 8 | 7.87 | DSADGFLK | 297 | 22.49 | 23.419 | 28.221 |
| 2 | 19 | 13.94 | TGLAPEFAALGESGSSSSK | 298 | 28.402 | 31.216 | 36.553 |
| 2 | 5 | 2.04 | CLVEK | 299 | 27.661 | 29.715 | 35.809 |
| 3 | 13 | 1.26 | TCVADESHAGCEK | 300 | 47.601 | 47.903 | 62.22 |
| 3 | 13 | 1.09 | GTGKECVPNSNER | 301 | 48.911 | 50.107 | 64.08 |

H = Hydrophobicity

Full Citations for Documents Referred to in the Specification
1. Lambert, J. P.; Ethier, M.; Smith, J. C.; Figeys, D. *Anal Chem*, 2005, 77, 3771-3787.
2. Sandra, K.; Moshir, M.; D'Hondt, F.; Verleysen, K.; Kas, K.; Sandra, P. *J Chromatogr B Analyt Technol Biomed Life Sci* 2008, 866, 48-63.
3. Washburn, M. P.; Walters, D.; Yates, J. R. 3rd. *Nat. Biotechnol.* 2001, 19, 242-247.
4. Meek, J. L. *Proc Natl Acad Sci USA* 1980, 77, 1632-1636.
5. Guo, D.; Mant, C. T.; Taneja, A. K.; Parker, J. M. R.; Hodges, R. S. *J. Chromatogr.* 1986, 359, 499-517.
6. Mant, C. T.; Burke, T. W. L.; Black, J. A.; Hodges, R. S. *J. Chromatogr.* 1988, 458, 193-205.
7. Houghten, R. A.; DeGraw, S. T. *J. Chromatogr.* 1987, 386, 223-228.
8. Krokhin, O. V. *Anal. Chem.* 2006, 78, 7785-7795.
9. Petritis, K.; Kangas, L. J.; Yan, B.; Monroe, M. E.; Strittmatter, E. F.; Qian, W. J.; Adkins, J. N.; Moore, R. J.; Xu. Y.; Lipton, M. S.; Camp, D. G. 2nd; Smith, R. D.; *Anal Chem.* 2006, 78, 5026-5039.
10. Shinoda, K.; Sugimoto, M.; Yachie, N.; Sugiyama, N.; Masuda, T.; Robert, M.; Soga, T.; Tomita, M. *J Proteome Res.* 2006, 5, 3312-3317.
11. Gorshkov, A. V.; Tarasova, I. A.; Evreinov, V. V.; Savitski, M. M.; Nielsen, M. L.; Zubarev, R. A.; Gorshkov, M. V. *Anal Chem.* 2006, 78, 7770-7777.
12. Klammer, A. A.; Yi, X.; Maccoss, M. J.; Noble, W. S. *Anal Chem.* 2007, 79, 6111-6118.
13. Gilar, M.; Jaworski, A.; Olivova, P.; Gebler, J. C. *Rapid Commun Mass Spectrom.* 2007, 21, 2813-2821.
14. Guo, D. C.; Mant, C. T.; Hodges, R. S. *J Chromatogr* 1987, 386, 205-222.
15. Spicer, V.; Yamchuk, A.; Cortens, J.; Sousa, S.; Ens, W.; Standing, K. G.; Wilkins, J. A.; Krokhin, O. V. *Anal Chem* 2007, 79, 8762-8768.
16. Dwivedi, R. C.; Spicer, V.; Harder, M.; Antonovici, M.; Ens, W.; Standing, K. G.; Wilkins, J. A.; Krokhin, O. V. *Anal Chem* 2008, 80, 7036-7042.
17. M. A. Stadalius, H. S. Gold, L. R. Snyder, J. Chromatogr. 1984, 296, 31-59.
18. J. L. Glaich, M. A. Quarry, J. F. Vasta, L. R. Snyder, *Anal. Chem.* 1986, 58, 280.
19. Aguilar, M. I.; Hodder, A. N.; Hearn, M. T. W. *J. Chromatogr.* 1985, 327, 115-138.
20. Hearn, M. T. W.; Aguilar, M. I. *J. Chromatogr.* 1986, 359, 31.
21. Hearn, M. T. W.; Aguilar, M. I. *J. Chromatogr.* 1987, 392, 33.
22. Snyder, L. R.; Dolan J. W. *High-Performance Gradient Elution: The Practical Application of the Linear-Solvent-Strength Model.* Wiley; New York: 2006.
23. Vu, H.; Spicer, V.; Gotfrid, A.; Krokhin, O. V. *J Chromatogr A*, 2010, 1217, 489-497.
24. Krokhin, O. V.; Spicer, V. *Anal Chem* 2009, 81, 9522-9530.
25. Strittmatter, E. F.; Kangas, L. J.; Petritis, K.; Mottaz, H. M.; Anderson, G. A.; Shen, Y.; Jacobs, J. M.; Camp, D. G., 2nd; Smith, R. D. *J Proteome Res* 2004, 3, 760-769.
26. Shinoda, K.; Tomita, M.; Ishihama, Y. *Bioinformatics* 2008, 24, 1590-1595.
27. Krokhin, O. V.; Craig, R.; Spicer, V.; Ens, W.; Standing, K. G.; Beavis, R. C.; Wilkins, J. A. *Mol Cell Proteomics* 2004, 3, 908-919.

What is claimed is:

1. A method for separating or isolating a peptide with a known amino acid sequence from a sample, the method comprising:
   (a) providing a sample comprising the peptide;
   (b) determining for the peptide a peptide charge, a peptide length, a hydrophobicity of the peptide, a distribution of hydrophobic amino acids within the peptide and a number of occurrences of each amino acid in the peptide;
   (c) using the function:

$$S = C1*Z^{C2} + C3*N^{C4} + C5*HI^{C6} + C7/Z + C8/N + C9/HI + C10*ZN + C11*ZHI + C12*NHI + C13*Z*N*HI^{C14} + B + S_{aa} + SSSF;$$

to determine a slope S for the peptide, wherein the slope S represents a change in retention of the peptide in a reverse phase chromatography column with respect to a change in a mobile phase gradient slope during reverse-phase chromatographic separation and where N is the peptide length, Z is the peptide charge, HI is the hydrophobicity of the peptide, $S_{aa}$ is calculated based on the number of occurrences of each amino acid in the peptide, SSSF is calculated based on the sequence of the peptide and where constant B and coefficients C1 to C14 are empirically determined;

(d) determining a retention time for the peptide in a reverse phase chromatography column based on the slope S;

(e) introducing the sample into the reverse phase chromatography column with a mobile phase; and (f) collecting an eluent out of the column at the retention time determined in (c), wherein the eluent contains the peptide.

2. The method of claim 1, for separating or isolating a peptide following:
  (i) transfer of scheduled MRM/SRM (multiple reaction monitoring or selected (selective) reaction monitoring) methods between chromatographic systems of different physical parameters;
  (ii) inter-laboratory collection of peptide retention data obtained using chromatographic systems of different physical parameters; or
  (iii) corrected retention time prediction using the hydrophobicity (retention time) prediction models developed for chromatographic systems of different physical parameters.

3. The method of claim 2, wherein the different physical parameters are gradient slope, flow rate, or column size.

4. The method of claim 1, further comprising using the positioning of acidic amino acids within the peptide adjacent to amino acids carrying positively charged amino groups to determine the slope S for the peptide.

5. The method of claim 1, wherein the number of occurrences of amino acids M, I, Y, W, V, F, P, C and L in the peptide has a positive effect on the slope S and the number of occurrences of amino acids Q, T, S, A, R, N, D, E, K, H and G in the peptide has a negative effect on the slope S.

6. The method of claim 1, wherein a uniform distribution of hydrophobic amino acid residues in the peptide increases the value of S for the peptide.

7. The method of claim 1, wherein $S_{aa}$ is calculated by
  a) identifying the number of occurrences of each amino acid in the peptide;
  b) multiplying the number of occurrences of each amino acid in the peptide by a corresponding coefficient for that amino acid ($S_i$) listed in Table 2; and
  c) summing each of the products determined in step b) to give a value for $S_{aa}$.

8. The method of claim 1, wherein SSSF is calculated based on distribution of hydrophobic amino acid residues within the peptide wherein a uniform distribution of hydrophobic amino acid residues increases the value of S for the peptide.

9. The method of claim 8, wherein the hydrophobic amino acid residues are leucine, isoleucine, phenylalanine, tryptophan, tyrosine, valine and methionine.

10. The method of claim 1, wherein SSSF is calculated based on positioning of acidic amino acids within the peptide adjacent to residues carrying positively charged amino groups wherein the presence of neighboring acidic amino acids and positively charged amino groups decreases the value of S for the peptide.

11. The method of claim 10, wherein the acidic amino acids are glutamic acid and aspartic acid and the positively charged amino groups are arginine, lysine, histidine and the N-terminus of the peptide.

* * * * *

SEQUENCE LISTING

<160> NUMBER OF SEQ ID NOS: 301

<210> SEQ ID NO 1
<211> LENGTH: 16
<212> TYPE: PRT
<213> ORGANISM: Artificial Sequence
<220> FEATURE:
<223> OTHER INFORMATION: Synthetic

<400> SEQUENCE: 1

Asn Glu Cys Phe Leu Gln His Lys Asp Asp Asn Pro Asn Leu Pro Arg

```
1               5                  10                 15
```

<210> SEQ ID NO 2
<211> LENGTH: 8
<212> TYPE: PRT
<213> ORGANISM: Artificial Sequence
<220> FEATURE:
<223> OTHER INFORMATION: Synthetic

<400> SEQUENCE: 2

```
Val Ala Thr Val Ser Leu Pro Arg
1               5
```

<210> SEQ ID NO 3
<211> LENGTH: 10
<212> TYPE: PRT
<213> ORGANISM: Artificial Sequence
<220> FEATURE:
<223> OTHER INFORMATION: Synthetic

<400> SEQUENCE: 3

```
Leu Gly Gly Gly Gly Gly Gly Asp Phe Arg
1               5                   10
```

<210> SEQ ID NO 4
<211> LENGTH: 9
<212> TYPE: PRT
<213> ORGANISM: Artificial Sequence
<220> FEATURE:
<223> OTHER INFORMATION: Synthetic

<400> SEQUENCE: 4

```
Leu Leu Gly Gly Gly Gly Asp Phe Arg
1               5
```

<210> SEQ ID NO 5
<211> LENGTH: 8
<212> TYPE: PRT
<213> ORGANISM: Artificial Sequence
<220> FEATURE:
<223> OTHER INFORMATION: Synthetic

<400> SEQUENCE: 5

```
Leu Leu Leu Gly Gly Asp Phe Arg
1               5
```

<210> SEQ ID NO 6
<211> LENGTH: 7
<212> TYPE: PRT
<213> ORGANISM: Artificial Sequence
<220> FEATURE:
<223> OTHER INFORMATION: Synthetic

<400> SEQUENCE: 6

```
Leu Leu Leu Leu Asp Phe Arg
1               5
```

<210> SEQ ID NO 7
<211> LENGTH: 8
<212> TYPE: PRT
<213> ORGANISM: Artificial Sequence
<220> FEATURE:
<223> OTHER INFORMATION: Synthetic

<400> SEQUENCE: 7

```
Leu Leu Leu Leu Leu Asp Phe Arg
1               5
```

```
<210> SEQ ID NO 8
<211> LENGTH: 8
<212> TYPE: PRT
<213> ORGANISM: Artificial Sequence
<220> FEATURE:
<223> OTHER INFORMATION: Synthetic

<400> SEQUENCE: 8

Leu Ala Ser Ala Ala Asp Phe Arg
1               5

<210> SEQ ID NO 9
<211> LENGTH: 8
<212> TYPE: PRT
<213> ORGANISM: Artificial Sequence
<220> FEATURE:
<223> OTHER INFORMATION: Synthetic

<400> SEQUENCE: 9

Leu Ala Ser Ala Ala His Phe Arg
1               5

<210> SEQ ID NO 10
<211> LENGTH: 8
<212> TYPE: PRT
<213> ORGANISM: Artificial Sequence
<220> FEATURE:
<223> OTHER INFORMATION: Synthetic

<400> SEQUENCE: 10

Leu Leu Ser Leu Ala Asp Phe Gly
1               5

<210> SEQ ID NO 11
<211> LENGTH: 17
<212> TYPE: PRT
<213> ORGANISM: Artificial Sequence
<220> FEATURE:
<223> OTHER INFORMATION: Synthetic

<400> SEQUENCE: 11

Leu Ala Gly Gly Gly Ser Ala Ser Ser Ala Asp Ala Ala Ala Phe
1               5                   10                  15

Arg

<210> SEQ ID NO 12
<211> LENGTH: 14
<212> TYPE: PRT
<213> ORGANISM: Artificial Sequence
<220> FEATURE:
<223> OTHER INFORMATION: Synthetic

<400> SEQUENCE: 12

Leu Leu Gly Gly Ser Leu Ser Ser Leu His Ala Ala Phe Arg
1               5                   10

<210> SEQ ID NO 13
<211> LENGTH: 17
<212> TYPE: PRT
<213> ORGANISM: Artificial Sequence
<220> FEATURE:
<223> OTHER INFORMATION: Synthetic

<400> SEQUENCE: 13

Leu Ala Gly Gly Gly Ser Ala Ser Ser Ala His Ala Ala Ala Phe
1               5                   10                  15
```

Arg

<210> SEQ ID NO 14
<211> LENGTH: 5
<212> TYPE: PRT
<213> ORGANISM: Artificial Sequence
<220> FEATURE:
<223> OTHER INFORMATION: Synthetic

<400> SEQUENCE: 14

Ile Glu Thr Met Arg
1               5

<210> SEQ ID NO 15
<211> LENGTH: 11
<212> TYPE: PRT
<213> ORGANISM: Artificial Sequence
<220> FEATURE:
<223> OTHER INFORMATION: Synthetic

<400> SEQUENCE: 15

Trp Cys Thr Ile Ser Gln Pro Glu Trp Phe Lys
1               5                   10

<210> SEQ ID NO 16
<211> LENGTH: 6
<212> TYPE: PRT
<213> ORGANISM: Artificial Sequence
<220> FEATURE:
<223> OTHER INFORMATION: Synthetic

<400> SEQUENCE: 16

Val Tyr Cys Asp Met Lys
1               5

<210> SEQ ID NO 17
<211> LENGTH: 13
<212> TYPE: PRT
<213> ORGANISM: Artificial Sequence
<220> FEATURE:
<223> OTHER INFORMATION: Synthetic

<400> SEQUENCE: 17

Leu Glu Ser Asp Val Ser Thr Gln Met Glu Tyr Cys Arg
1               5                   10

<210> SEQ ID NO 18
<211> LENGTH: 6
<212> TYPE: PRT
<213> ORGANISM: Artificial Sequence
<220> FEATURE:
<223> OTHER INFORMATION: Synthetic

<400> SEQUENCE: 18

Trp Tyr Ser Met Lys Lys
1               5

<210> SEQ ID NO 19
<211> LENGTH: 22
<212> TYPE: PRT
<213> ORGANISM: Artificial Sequence
<220> FEATURE:
<223> OTHER INFORMATION: Synthetic

<400> SEQUENCE: 19

Ala Pro Val Asp Ala Phe Lys Glu Cys His Leu Ala Gln Val Pro Ser
1               5                   10                  15

His Ala Val Val Ala Arg
            20

<210> SEQ ID NO 20
<211> LENGTH: 7
<212> TYPE: PRT
<213> ORGANISM: Artificial Sequence
<220> FEATURE:
<223> OTHER INFORMATION: Synthetic

<400> SEQUENCE: 20

Leu Ser Gln Lys Phe Pro Lys
1               5

<210> SEQ ID NO 21
<211> LENGTH: 7
<212> TYPE: PRT
<213> ORGANISM: Artificial Sequence
<220> FEATURE:
<223> OTHER INFORMATION: Synthetic

<400> SEQUENCE: 21

Tyr Leu Tyr Glu Ile Ala Arg
1               5

<210> SEQ ID NO 22
<211> LENGTH: 8
<212> TYPE: PRT
<213> ORGANISM: Artificial Sequence
<220> FEATURE:
<223> OTHER INFORMATION: Synthetic

<400> SEQUENCE: 22

Lys Val Ile Glu Gln Val Gln Arg
1               5

<210> SEQ ID NO 23
<211> LENGTH: 6
<212> TYPE: PRT
<213> ORGANISM: Artificial Sequence
<220> FEATURE:
<223> OTHER INFORMATION: Synthetic

<400> SEQUENCE: 23

Thr Pro Ile Ala Val Arg
1               5

<210> SEQ ID NO 24
<211> LENGTH: 7
<212> TYPE: PRT
<213> ORGANISM: Artificial Sequence
<220> FEATURE:
<223> OTHER INFORMATION: Synthetic

<400> SEQUENCE: 24

Arg Thr Pro Ile Ala Val Arg
1               5

<210> SEQ ID NO 25
<211> LENGTH: 11
<212> TYPE: PRT
<213> ORGANISM: Artificial Sequence
<220> FEATURE:
<223> OTHER INFORMATION: Synthetic

<400> SEQUENCE: 25

Gln Phe Val Ser Ser Ser Thr Thr Val Asn Arg
1               5                   10

```
<210> SEQ ID NO 26
<211> LENGTH: 7
<212> TYPE: PRT
<213> ORGANISM: Artificial Sequence
<220> FEATURE:
<223> OTHER INFORMATION: Synthetic

<400> SEQUENCE: 26

Val Ile Glu Gln Val Gln Arg
1               5

<210> SEQ ID NO 27
<211> LENGTH: 8
<212> TYPE: PRT
<213> ORGANISM: Artificial Sequence
<220> FEATURE:
<223> OTHER INFORMATION: Synthetic

<400> SEQUENCE: 27

Leu Leu Ser Leu Leu Asp Phe Arg
1               5

<210> SEQ ID NO 28
<211> LENGTH: 9
<212> TYPE: PRT
<213> ORGANISM: Artificial Seuqence
<220> FEATURE:
<223> OTHER INFORMATION: Synthetic

<400> SEQUENCE: 28

Leu Leu Ile Glu Met Glu Asp Trp Lys
1               5

<210> SEQ ID NO 29
<211> LENGTH: 8
<212> TYPE: PRT
<213> ORGANISM: Artificial Sequence
<220> FEATURE:
<223> OTHER INFORMATION: Synthetic

<400> SEQUENCE: 29

Phe Pro Thr Ile Pro Leu Ser Arg
1               5

<210> SEQ ID NO 30
<211> LENGTH: 11
<212> TYPE: PRT
<213> ORGANISM: Artificial Sequence
<220> FEATURE:
<223> OTHER INFORMATION: Synthetic

<400> SEQUENCE: 30

Leu Leu Gly Ser Leu Ser Leu Asp Ala Phe Arg
1               5                   10

<210> SEQ ID NO 31
<211> LENGTH: 11
<212> TYPE: PRT
<213> ORGANISM: Artificial Sequence
<220> FEATURE:
<223> OTHER INFORMATION: Synthetic

<400> SEQUENCE: 31

Glu Leu Pro Asp Pro Gln Glu Ser Ile Gln Arg
1               5                   10
```

```
<210> SEQ ID NO 32
<211> LENGTH: 12
<212> TYPE: PRT
<213> ORGANISM: Artificial Sequence
<220> FEATURE:
<223> OTHER INFORMATION: Synthetic

<400> SEQUENCE: 32

Phe Phe Ser Ala Ser Cys Val Pro Cys Ile Asp Arg
1               5                   10

<210> SEQ ID NO 33
<211> LENGTH: 8
<212> TYPE: PRT
<213> ORGANISM: Artificial Sequence
<220> FEATURE:
<223> OTHER INFORMATION: Synthetic

<400> SEQUENCE: 33

Ile Arg Pro Tyr Phe Pro Glu Gln
1               5

<210> SEQ ID NO 34
<211> LENGTH: 9
<212> TYPE: PRT
<213> ORGANISM: Artificial Sequence
<220> FEATURE:
<223> OTHER INFORMATION: Synthetic

<400> SEQUENCE: 34

Thr His Phe Ser Gly Asp Val Gln Arg
1               5

<210> SEQ ID NO 35
<211> LENGTH: 12
<212> TYPE: PRT
<213> ORGANISM: Artificial Sequence
<220> FEATURE:
<223> OTHER INFORMATION: Synthetic

<400> SEQUENCE: 35

Tyr Ile Cys Asp Asn Gln Asp Thr Ile Ser Ser Lys
1               5                   10

<210> SEQ ID NO 36
<211> LENGTH: 12
<212> TYPE: PRT
<213> ORGANISM: Artificial Sequence
<220> FEATURE:
<223> OTHER INFORMATION: Synthetic

<400> SEQUENCE: 36

Glu Tyr Glu Ala Thr Leu Glu Glu Cys Cys Ala Lys
1               5                   10

<210> SEQ ID NO 37
<211> LENGTH: 14
<212> TYPE: PRT
<213> ORGANISM: Artificial Sequence
<220> FEATURE:
<223> OTHER INFORMATION: Synthetic

<400> SEQUENCE: 37

Leu Tyr Lys Glu Leu Pro Asp Pro Gln Glu Ser Ile Gln Arg
1               5                   10

<210> SEQ ID NO 38
<211> LENGTH: 4
```

```
<212> TYPE: PRT
<213> ORGANISM: Artificial Sequence
<220> FEATURE:
<223> OTHER INFORMATION: Synthetic

<400> SEQUENCE: 38

Trp Gln Trp Arg
1

<210> SEQ ID NO 39
<211> LENGTH: 10
<212> TYPE: PRT
<213> ORGANISM: Artificial Sequence
<220> FEATURE:
<223> OTHER INFORMATION: Synthetic

<400> SEQUENCE: 39

Leu Cys Glu Asn Ile Ala Gly His Leu Lys
1               5                   10

<210> SEQ ID NO 40
<211> LENGTH: 21
<212> TYPE: PRT
<213> ORGANISM: Artificial Sequence
<220> FEATURE:
<223> OTHER INFORMATION: Synthetic

<400> SEQUENCE: 40

Lys Lys Glu Glu Ala Pro Ser Leu Arg Pro Val Pro Pro Pro Ile Ser
1               5                   10                  15

Gly Gly Gly Tyr Arg
            20

<210> SEQ ID NO 41
<211> LENGTH: 13
<212> TYPE: PRT
<213> ORGANISM: Artificial Sequence
<220> FEATURE:
<223> OTHER INFORMATION: Synthetic

<400> SEQUENCE: 41

Lys Pro Val Thr Asp Ala Glu Asn Cys His Leu Ala Arg
1               5                   10

<210> SEQ ID NO 42
<211> LENGTH: 12
<212> TYPE: PRT
<213> ORGANISM: Artificial Sequence
<220> FEATURE:
<223> OTHER INFORMATION: Synthetic

<400> SEQUENCE: 42

Glu Pro Ile Ser Val Ser Ser Gln Gln Met Leu Lys
1               5                   10

<210> SEQ ID NO 43
<211> LENGTH: 12
<212> TYPE: PRT
<213> ORGANISM: Artificial Sequence
<220> FEATURE:
<223> OTHER INFORMATION: Synthetic

<400> SEQUENCE: 43

Thr Val Met Glu Asn Phe Val Ala Phe Val Asp Lys
1               5                   10

<210> SEQ ID NO 44
```

```
<211> LENGTH: 6
<212> TYPE: PRT
<213> ORGANISM: Artificial Sequence
<220> FEATURE:
<223> OTHER INFORMATION: Synthetic

<400> SEQUENCE: 44

Ile Ile Pro Leu Asn Arg
1               5

<210> SEQ ID NO 45
<211> LENGTH: 10
<212> TYPE: PRT
<213> ORGANISM: Artificial Sequence
<220> FEATURE:
<223> OTHER INFORMATION: Synthetic

<400> SEQUENCE: 45

Leu Gly Ala Pro Ser Ile Thr Cys Val Arg
1               5                   10

<210> SEQ ID NO 46
<211> LENGTH: 22
<212> TYPE: PRT
<213> ORGANISM: Artificial Sequence
<220> FEATURE:
<223> OTHER INFORMATION: Synthetic

<400> SEQUENCE: 46

Lys Pro Val Thr Glu Ala Gln Ser Cys His Leu Ala Val Ala Pro Asn
1               5                   10                  15

His Ala Val Val Ser Arg
            20

<210> SEQ ID NO 47
<211> LENGTH: 8
<212> TYPE: PRT
<213> ORGANISM: Artificial Sequence
<220> FEATURE:
<223> OTHER INFORMATION: Synthetic

<400> SEQUENCE: 47

Asn Thr Val Asp Ser Val Ser Arg
1               5

<210> SEQ ID NO 48
<211> LENGTH: 18
<212> TYPE: PRT
<213> ORGANISM: Artificial Sequence
<220> FEATURE:
<223> OTHER INFORMATION: Synthetic

<400> SEQUENCE: 48

Phe Ser Thr Val Ala Gly Glu Ser Gly Ser Ala Asp Thr Val Arg Asp
1               5                   10                  15

Pro Arg

<210> SEQ ID NO 49
<211> LENGTH: 8
<212> TYPE: PRT
<213> ORGANISM: Artificial Sequence
<220> FEATURE:
<223> OTHER INFORMATION: Synthetic

<400> SEQUENCE: 49

Leu Leu Ser Leu Ala Asp Phe Arg
1               5
```

```
<210> SEQ ID NO 50
<211> LENGTH: 17
<212> TYPE: PRT
<213> ORGANISM: Artificial Sequence
<220> FEATURE:
<223> OTHER INFORMATION: Synthetic

<400> SEQUENCE: 50

Val Val Gln Leu Glu Ala Asn Cys Gln Glu Pro Cys Gln Asp Thr Val
1               5                   10                  15

Lys

<210> SEQ ID NO 51
<211> LENGTH: 12
<212> TYPE: PRT
<213> ORGANISM: Artificial Sequence
<220> FEATURE:
<223> OTHER INFORMATION: Synthetic

<400> SEQUENCE: 51

Thr Tyr Asp Ser Tyr Leu Gly Asp Asp Tyr Val Arg
1               5                   10

<210> SEQ ID NO 52
<211> LENGTH: 15
<212> TYPE: PRT
<213> ORGANISM: Artificial Sequence
<220> FEATURE:
<223> OTHER INFORMATION: Synthetic

<400> SEQUENCE: 52

Leu Gly Pro Asn Tyr Leu Gln Ile Pro Val Asn Cys Pro Tyr Arg
1               5                   10                  15

<210> SEQ ID NO 53
<211> LENGTH: 5
<212> TYPE: PRT
<213> ORGANISM: Artificial Sequence
<220> FEATURE:
<223> OTHER INFORMATION: Synthetic

<400> SEQUENCE: 53

Ile Val Asn Leu Arg
1               5

<210> SEQ ID NO 54
<211> LENGTH: 5
<212> TYPE: PRT
<213> ORGANISM: Artificial Sequence
<220> FEATURE:
<223> OTHER INFORMATION: Synthetic

<400> SEQUENCE: 54

Trp Asp Pro Tyr Lys
1               5

<210> SEQ ID NO 55
<211> LENGTH: 14
<212> TYPE: PRT
<213> ORGANISM: Artificial Sequence
<220> FEATURE:
<223> OTHER INFORMATION: Synthetic

<400> SEQUENCE: 55

Leu Ala Gly Gly Ser Ala Ser Ser Ala His Ala Ala Phe Arg
1               5                   10
```

```
<210> SEQ ID NO 56
<211> LENGTH: 11
<212> TYPE: PRT
<213> ORGANISM: Artificial Sequence
<220> FEATURE:
<223> OTHER INFORMATION: Synthetic

<400> SEQUENCE: 56

Arg Leu Cys Glu Asn Ile Ala Gly His Leu Lys
1               5                   10

<210> SEQ ID NO 57
<211> LENGTH: 13
<212> TYPE: PRT
<213> ORGANISM: Artificial Sequence
<220> FEATURE:
<223> OTHER INFORMATION: Synthetic

<400> SEQUENCE: 57

Thr Ser Ser Ser Thr Phe Gln Tyr Ile Thr Leu Leu Lys
1               5                   10

<210> SEQ ID NO 58
<211> LENGTH: 9
<212> TYPE: PRT
<213> ORGANISM: Artificial Sequence
<220> FEATURE:
<223> OTHER INFORMATION: Synethic

<400> SEQUENCE: 58

Tyr Tyr Gly Tyr Thr Gly Ala Phe Arg
1               5

<210> SEQ ID NO 59
<211> LENGTH: 5
<212> TYPE: PRT
<213> ORGANISM: Artificial Sequence
<220> FEATURE:
<223> OTHER INFORMATION: Synthetic

<400> SEQUENCE: 59

Trp Tyr Ser Met Lys
1               5

<210> SEQ ID NO 60
<211> LENGTH: 14
<212> TYPE: PRT
<213> ORGANISM: Artificial Sequence
<220> FEATURE:
<223> OTHER INFORMATION: Synthetic

<400> SEQUENCE: 60

Val Pro Gln Val Ser Thr Pro Thr Leu Val Glu Val Ser Arg
1               5                   10

<210> SEQ ID NO 61
<211> LENGTH: 8
<212> TYPE: PRT
<213> ORGANISM: Artificial Sequence
<220> FEATURE:
<223> OTHER INFORMATION: Synthetic

<400> SEQUENCE: 61

Asn Leu Asn Arg Glu Asp Phe Arg
1               5
```

```
<210> SEQ ID NO 62
<211> LENGTH: 14
<212> TYPE: PRT
<213> ORGANISM: Artificial Sequence
<220> FEATURE:
<223> OTHER INFORMATION: Synthetic

<400> SEQUENCE: 62

Leu Leu Gly Gly Ser Leu Ser Ser Leu Asp Ala Ala Phe Arg
1               5                   10

<210> SEQ ID NO 63
<211> LENGTH: 11
<212> TYPE: PRT
<213> ORGANISM: Artificial Sequence
<220> FEATURE:
<223> OTHER INFORMATION: Synthetic

<400> SEQUENCE: 63

Gln Ala Tyr Pro Asn Leu Cys Gln Leu Cys Lys
1               5                   10

<210> SEQ ID NO 64
<211> LENGTH: 5
<212> TYPE: PRT
<213> ORGANISM: Artificial Sequence
<220> FEATURE:
<223> OTHER INFORMATION: Synthetic

<400> SEQUENCE: 64

Phe Cys Leu Phe Lys
1               5

<210> SEQ ID NO 65
<211> LENGTH: 13
<212> TYPE: PRT
<213> ORGANISM: Artificial Sequence
<220> FEATURE:
<223> OTHER INFORMATION: Synthetic

<400> SEQUENCE: 65

Phe Asn Ser Ala Asn Asp Asp Asn Val Thr Gln Val Arg
1               5                   10

<210> SEQ ID NO 66
<211> LENGTH: 13
<212> TYPE: PRT
<213> ORGANISM: Artificial Sequence
<220> FEATURE:
<223> OTHER INFORMATION: Synthetic

<400> SEQUENCE: 66

Gly Leu Ile Asp Glu Val Asp Gln Asp Phe Thr Ser Arg
1               5                   10

<210> SEQ ID NO 67
<211> LENGTH: 19
<212> TYPE: PRT
<213> ORGANISM: Artificial Sequence
<220> FEATURE:
<223> OTHER INFORMATION: Synthetic

<400> SEQUENCE: 67

Asp Lys Val Val Gln Leu Glu Ala Asn Cys Gln Glu Pro Cys Gln Asp
1               5                   10                  15

Thr Val Lys
```

```
<210> SEQ ID NO 68
<211> LENGTH: 5
<212> TYPE: PRT
<213> ORGANISM: Artificial Sequence
<220> FEATURE:
<223> OTHER INFORMATION: Synthetic

<400> SEQUENCE: 68

Leu Asn Glu Leu Arg
1               5

<210> SEQ ID NO 69
<211> LENGTH: 8
<212> TYPE: PRT
<213> ORGANISM: Artificial Sequence
<220> FEATURE:
<223> OTHER INFORMATION: Synthetic

<400> SEQUENCE: 69

Leu Cys Gln Leu Cys Ala Gly Lys
1               5

<210> SEQ ID NO 70
<211> LENGTH: 16
<212> TYPE: PRT
<213> ORGANISM: Artificial Sequence
<220> FEATURE:
<223> OTHER INFORMATION: Synthetic

<400> SEQUENCE: 70

Arg Pro Cys Phe Ser Ala Leu Thr Pro Asp Glu Thr Tyr Val Pro Lys
1               5                   10                  15

<210> SEQ ID NO 71
<211> LENGTH: 8
<212> TYPE: PRT
<213> ORGANISM: Artificial Sequence
<220> FEATURE:
<223> OTHER INFORMATION: Synthetic

<400> SEQUENCE: 71

Ala Phe Ala Leu Glu Cys Ile Arg
1               5

<210> SEQ ID NO 72
<211> LENGTH: 11
<212> TYPE: PRT
<213> ORGANISM: Artificial Sequence
<220> FEATURE:
<223> OTHER INFORMATION: Synethic

<400> SEQUENCE: 72

Lys Leu Gly Ala Pro Ser Ile Thr Cys Val Arg
1               5                   10

<210> SEQ ID NO 73
<211> LENGTH: 5
<212> TYPE: PRT
<213> ORGANISM: Artificial Sequence
<220> FEATURE:
<223> OTHER INFORMATION: Synthetic

<400> SEQUENCE: 73

Ile Glu Ile Leu Arg
1               5

<210> SEQ ID NO 74
<211> LENGTH: 10
```

```
<212> TYPE: PRT
<213> ORGANISM: Artificial Sequence
<220> FEATURE:
<223> OTHER INFORMATION: Synthetic

<400> SEQUENCE: 74

Val Gly Asp Ala Asn Pro Ala Leu Gln Lys
1               5                   10

<210> SEQ ID NO 75
<211> LENGTH: 17
<212> TYPE: PRT
<213> ORGANISM: Artificial Sequence
<220> FEATURE:
<223> OTHER INFORMATION: Synethic

<400> SEQUENCE: 75

Leu Lys Pro Asp Pro Asn Thr Leu Cys Asp Glu Phe Lys Ala Asp Glu
1               5                   10                  15

Lys

<210> SEQ ID NO 76
<211> LENGTH: 8
<212> TYPE: PRT
<213> ORGANISM: Artificial Sequence
<220> FEATURE:
<223> OTHER INFORMATION: Synthetic

<400> SEQUENCE: 76

Leu Leu His Ala Ala His Phe Arg
1               5

<210> SEQ ID NO 77
<211> LENGTH: 6
<212> TYPE: PRT
<213> ORGANISM: Artificial Sequence
<220> FEATURE:
<223> OTHER INFORMATION: Synthetic

<400> SEQUENCE: 77

Asn Trp Ile Gln Tyr Lys
1               5

<210> SEQ ID NO 78
<211> LENGTH: 8
<212> TYPE: PRT
<213> ORGANISM: Artificial Sequence
<220> FEATURE:
<223> OTHER INFORMATION: Synthetic

<400> SEQUENCE: 78

Leu Leu His Leu Ala His Phe Arg
1               5

<210> SEQ ID NO 79
<211> LENGTH: 11
<212> TYPE: PRT
<213> ORGANISM: Artificial Sequence
<220> FEATURE:
<223> OTHER INFORMATION: Synthetic

<400> SEQUENCE: 79

Glu Pro Tyr Phe Gly Tyr Ser Gly Ala Phe Lys
1               5                   10

<210> SEQ ID NO 80
<211> LENGTH: 10
```

```
<212> TYPE: PRT
<213> ORGANISM: Artificial Sequence
<220> FEATURE:
<223> OTHER INFORMATION: Synthetic

<400> SEQUENCE: 80

Arg Leu Asp Gly Ser Leu Asp Phe Lys Lys
1               5                   10

<210> SEQ ID NO 81
<211> LENGTH: 11
<212> TYPE: PRT
<213> ORGANISM: Artificial Sequence
<220> FEATURE:
<223> OTHER INFORMATION: Synthetic

<400> SEQUENCE: 81

Leu Ala Gly Ser Ala Ser Ala His Ala Phe Arg
1               5                   10

<210> SEQ ID NO 82
<211> LENGTH: 13
<212> TYPE: PRT
<213> ORGANISM: Artificial Sequence
<220> FEATURE:
<223> OTHER INFORMATION: Synthetic

<400> SEQUENCE: 82

Leu Lys Pro Asp Pro Asn Thr Leu Cys Asp Glu Phe Lys
1               5                   10

<210> SEQ ID NO 83
<211> LENGTH: 9
<212> TYPE: PRT
<213> ORGANISM: Artificial Sequence
<220> FEATURE:
<223> OTHER INFORMATION: Synthetic

<400> SEQUENCE: 83

Gly Tyr Leu Ala Val Ala Val Val Lys
1               5

<210> SEQ ID NO 84
<211> LENGTH: 11
<212> TYPE: PRT
<213> ORGANISM: Artificial Sequence
<220> FEATURE:
<223> OTHER INFORMATION: Synthetic

<400> SEQUENCE: 84

Leu Leu Gly Ser Leu Ser Leu His Ala Phe Arg
1               5                   10

<210> SEQ ID NO 85
<211> LENGTH: 16
<212> TYPE: PRT
<213> ORGANISM: Artificial Sequence
<220> FEATURE:
<223> OTHER INFORMATION: Synthetic

<400> SEQUENCE: 85

Asn Glu Cys Phe Leu Ser His Lys Asp Asp Ser Pro Asp Leu Pro Lys
1               5                   10                  15

<210> SEQ ID NO 86
<211> LENGTH: 9
<212> TYPE: PRT
<213> ORGANISM: Artificial Sequence
```

```
<220> FEATURE:
<223> OTHER INFORMATION: Synthetic

<400> SEQUENCE: 86

Asp Ile Gln Tyr Leu Pro Ile Leu Lys
1               5

<210> SEQ ID NO 87
<211> LENGTH: 8
<212> TYPE: PRT
<213> ORGANISM: Artificial Sequence
<220> FEATURE:
<223> OTHER INFORMATION: Synthetic

<400> SEQUENCE: 87

Leu Ala Val Ala Ala His Phe Arg
1               5

<210> SEQ ID NO 88
<211> LENGTH: 15
<212> TYPE: PRT
<213> ORGANISM: Artificial Sequence
<220> FEATURE:
<223> OTHER INFORMATION: Synthetic

<400> SEQUENCE: 88

Glu Cys His Leu Ala Gln Val Pro Ser His Ala Val Val Ala Arg
1               5                   10                  15

<210> SEQ ID NO 89
<211> LENGTH: 8
<212> TYPE: PRT
<213> ORGANISM: Artificial Sequence
<220> FEATURE:
<223> OTHER INFORMATION: Synthetic

<400> SEQUENCE: 89

Glu Asn Phe Glu Val Leu Cys Lys
1               5

<210> SEQ ID NO 90
<211> LENGTH: 16
<212> TYPE: PRT
<213> ORGANISM: Artificial Sequence
<220> FEATURE:
<223> OTHER INFORMATION: Synthetic

<400> SEQUENCE: 90

Gly Asp Ser Val Ser Gln Gly Thr Gly Leu Ala Pro Gly Ser Pro Arg
1               5                   10                  15

<210> SEQ ID NO 91
<211> LENGTH: 13
<212> TYPE: PRT
<213> ORGANISM: Artificial Sequence
<220> FEATURE:
<223> OTHER INFORMATION: Synthetic

<400> SEQUENCE: 91

Leu Gly Glu Tyr Gly Phe Gln Asn Ala Leu Ile Val Arg
1               5                   10

<210> SEQ ID NO 92
<211> LENGTH: 14
<212> TYPE: PRT
<213> ORGANISM: Artificial Sequence
<220> FEATURE:
<223> OTHER INFORMATION: Synthetic
```

<400> SEQUENCE: 92

Ile Pro Ser Lys Val Asp Ser Ala Leu Tyr Leu Gly Ser Arg
1               5                   10

<210> SEQ ID NO 93
<211> LENGTH: 8
<212> TYPE: PRT
<213> ORGANISM: Artificial Sequence
<220> FEATURE:
<223> OTHER INFORMATION: Synthetic

<400> SEQUENCE: 93

Ala Glu Phe Val Glu Val Thr Lys
1               5

<210> SEQ ID NO 94
<211> LENGTH: 8
<212> TYPE: PRT
<213> ORGANISM: Artificial Sequence
<220> FEATURE:
<223> OTHER INFORMATION: Synthetic

<400> SEQUENCE: 94

Leu Leu His Leu Leu His Phe Arg
1               5

<210> SEQ ID NO 95
<211> LENGTH: 9
<212> TYPE: PRT
<213> ORGANISM: Artificial Sequence
<220> FEATURE:
<223> OTHER INFORMATION: Synthetic

<400> SEQUENCE: 95

Ile Gln Leu Glu Asp Trp Asn Gly Arg
1               5

<210> SEQ ID NO 96
<211> LENGTH: 8
<212> TYPE: PRT
<213> ORGANISM: Artificial Sequence
<220> FEATURE:
<223> OTHER INFORMATION: Synthetic

<400> SEQUENCE: 96

Leu Leu Val Ala Ala His Phe Arg
1               5

<210> SEQ ID NO 97
<211> LENGTH: 12
<212> TYPE: PRT
<213> ORGANISM: Artificial Sequence
<220> FEATURE:
<223> OTHER INFORMATION: Synthetic

<400> SEQUENCE: 97

Glu Thr Tyr Gly Asp Met Ala Asp Cys Cys Glu Lys
1               5                   10

<210> SEQ ID NO 98
<211> LENGTH: 15
<212> TYPE: PRT
<213> ORGANISM: Artificial Sequence
<220> FEATURE:
<223> OTHER INFORMATION: Synthetic

<400> SEQUENCE: 98

```
Thr Pro Cys Thr Val Thr Cys Asn Ile Pro Val Val Ser Gly Lys
1               5                   10                  15

<210> SEQ ID NO 99
<211> LENGTH: 14
<212> TYPE: PRT
<213> ORGANISM: Artificial Sequence
<220> FEATURE:
<223> OTHER INFORMATION: Synthetic

<400> SEQUENCE: 99

Ile Gln Ala Leu Leu Asp Lys Tyr Asn Glu Glu Lys Pro Lys
1               5                   10

<210> SEQ ID NO 100
<211> LENGTH: 5
<212> TYPE: PRT
<213> ORGANISM: Artificial Sequence
<220> FEATURE:
<223> OTHER INFORMATION: Synthetic

<400> SEQUENCE: 100

Arg Trp Gln Trp Arg
1               5

<210> SEQ ID NO 101
<211> LENGTH: 8
<212> TYPE: PRT
<213> ORGANISM: Artificial Sequecne
<220> FEATURE:
<223> OTHER INFORMATION: Synthetic

<400> SEQUENCE: 101

Leu Leu Ser Leu Leu His Phe Arg
1               5

<210> SEQ ID NO 102
<211> LENGTH: 10
<212> TYPE: PRT
<213> ORGANISM: Artificial Sequence
<220> FEATURE:
<223> OTHER INFORMATION: Synthetic

<400> SEQUENCE: 102

Phe Lys Asp Leu Gly Glu Glu His Phe Lys
1               5                   10

<210> SEQ ID NO 103
<211> LENGTH: 10
<212> TYPE: PRT
<213> ORGANISM: Artificial Sequence
<220> FEATURE:
<223> OTHER INFORMATION: Synthetic

<400> SEQUENCE: 103

Leu Val Asn Glu Leu Thr Glu Phe Ala Lys
1               5                   10

<210> SEQ ID NO 104
<211> LENGTH: 11
<212> TYPE: PRT
<213> ORGANISM: Artificial Sequence
<220> FEATURE:
<223> OTHER INFORMATION: Synthetic

<400> SEQUENCE: 104

His Leu Val Asp Glu Pro Gln Asn Leu Ile Lys
```

<210> SEQ ID NO 105
<211> LENGTH: 13
<212> TYPE: PRT
<213> ORGANISM: Artificial Sequene
<220> FEATURE:
<223> OTHER INFORMATION: Synthetic

<400> SEQUENCE: 105

Lys Thr Tyr Asp Ser Tyr Leu Gly Asp Asp Tyr Val Arg
1               5                   10

<210> SEQ ID NO 106
<211> LENGTH: 13
<212> TYPE: PRT
<213> ORGANISM: Artificial Sequence
<220> FEATURE:
<223> OTHER INFORMATION: Synthetic

<400> SEQUENCE: 106

Cys Leu Met Glu Gly Ala Gly Asp Val Ala Phe Val Lys
1               5                   10

<210> SEQ ID NO 107
<211> LENGTH: 11
<212> TYPE: PRT
<213> ORGANISM: Artificial Sequence
<220> FEATURE:
<223> OTHER INFORMATION: Synthetic

<400> SEQUENCE: 107

Ser Gln Leu Gln Glu Ala Pro Leu Glu Trp Lys
1               5                   10

<210> SEQ ID NO 108
<211> LENGTH: 6
<212> TYPE: PRT
<213> ORGANISM: Artificial Sequence
<220> FEATURE:
<223> OTHER INFORMATION: Synthetic

<400> SEQUENCE: 108

Tyr Leu Thr Thr Leu Lys
1               5

<210> SEQ ID NO 109
<211> LENGTH: 15
<212> TYPE: PRT
<213> ORGANISM: Artificial Sequence
<220> FEATURE:
<223> OTHER INFORMATION: Synthetic

<400> SEQUENCE: 109

Ile His Leu Ile Ser Thr Gln Ser Thr Ile Pro Tyr Val Leu Arg
1               5                   10                  15

<210> SEQ ID NO 110
<211> LENGTH: 10
<212> TYPE: PRT
<213> ORGANISM: Artificial Sequence
<220> FEATURE:
<223> OTHER INFORMATION: Synthetic

<400> SEQUENCE: 110

Met Ser Thr Ile Thr Gly Pro Val Pro Arg
1               5                   10

<210> SEQ ID NO 111
<211> LENGTH: 11
<212> TYPE: PRT
<213> ORGANISM: Artificial Sequence
<220> FEATURE:
<223> OTHER INFORMATION: Synthetic

<400> SEQUENCE: 111

Glu Thr Thr Val Phe Glu Asn Leu Pro Glu Lys
1               5                   10

<210> SEQ ID NO 112
<211> LENGTH: 8
<212> TYPE: PRT
<213> ORGANISM: Artificial Sequence
<220> FEATURE:
<223> OTHER INFORMATION: Synthetic

<400> SEQUENCE: 112

Leu Leu Val Leu Leu His Phe Arg
1               5

<210> SEQ ID NO 113
<211> LENGTH: 12
<212> TYPE: PRT
<213> ORGANISM: Artificial Sequence
<220> FEATURE:
<223> OTHER INFORMATION: Synthetic

<400> SEQUENCE: 113

Asn Phe Ser Asp Val His Pro Glu Tyr Gly Ser Arg
1               5                   10

<210> SEQ ID NO 114
<211> LENGTH: 15
<212> TYPE: PRT
<213> ORGANISM: Artificial Sequence
<220> FEATURE:
<223> OTHER INFORMATION: Synthetic

<400> SEQUENCE: 114

Lys Val Pro Gln Val Ser Thr Pro Thr Leu Val Glu Val Ser Arg
1               5                   10                  15

<210> SEQ ID NO 115
<211> LENGTH: 20
<212> TYPE: PRT
<213> ORGANISM: Artificial Sequence
<220> FEATURE:
<223> OTHER INFORMATION: Synthetic

<400> SEQUENCE: 115

Lys Glu Glu Ala Pro Ser Leu Arg Pro Val Pro Pro Pro Ile Ser Gly
1               5                   10                  15

Gly Gly Tyr Arg
            20

<210> SEQ ID NO 116
<211> LENGTH: 7
<212> TYPE: PRT
<213> ORGANISM: Artificial Seuqence
<220> FEATURE:
<223> OTHER INFORMATION: Synthetic

<400> SEQUENCE: 116

Asn Ile Val Glu Leu Met Arg
1               5

```
<210> SEQ ID NO 117
<211> LENGTH: 8
<212> TYPE: PRT
<213> ORGANISM: Artificial Sequence
<220> FEATURE:
<223> OTHER INFORMATION: Synthetic

<400> SEQUENCE: 117

Leu Leu Ser Leu Ala His Phe Arg
1               5

<210> SEQ ID NO 118
<211> LENGTH: 11
<212> TYPE: PRT
<213> ORGANISM: Artificial Sequence
<220> FEATURE:
<223> OTHER INFORMATION: Synthetic

<400> SEQUENCE: 118

Ile Ser Gln Leu Thr Asn Met Gly Pro Thr Lys
1               5                   10

<210> SEQ ID NO 119
<211> LENGTH: 12
<212> TYPE: PRT
<213> ORGANISM: Artificial Sequence
<220> FEATURE:
<223> OTHER INFORMATION: Synthetic

<400> SEQUENCE: 119

Ile Leu Glu Ser Gly Pro Phe Val Ser Cys Val Lys
1               5                   10

<210> SEQ ID NO 120
<211> LENGTH: 7
<212> TYPE: PRT
<213> ORGANISM: Artificial Sequence
<220> FEATURE:
<223> OTHER INFORMATION: Synthetic

<400> SEQUENCE: 120

Tyr Gln Leu Ser Val Ser Lys
1               5

<210> SEQ ID NO 121
<211> LENGTH: 14
<212> TYPE: PRT
<213> ORGANISM: Artificial Sequence
<220> FEATURE:
<223> OTHER INFORMATION: Synthetic

<400> SEQUENCE: 121

Leu Ala Gly Gly Ser Ala Ser Ser Ala Asp Ala Ala Phe Arg
1               5                   10

<210> SEQ ID NO 122
<211> LENGTH: 13
<212> TYPE: PRT
<213> ORGANISM: Artificial Sequence
<220> FEATURE:
<223> OTHER INFORMATION: Synthetic

<400> SEQUENCE: 122

Ile Leu Glu Ser Gly Pro Phe Val Ser Cys Val Lys Lys
1               5                   10
```

```
<210> SEQ ID NO 123
<211> LENGTH: 14
<212> TYPE: PRT
<213> ORGANISM: Artificial Sequence
<220> FEATURE:
<223> OTHER INFORMATION: Synthetic

<400> SEQUENCE: 123

Val Trp Pro His Gly Asp Tyr Pro Leu Ile Pro Val Gly Lys
1               5                   10

<210> SEQ ID NO 124
<211> LENGTH: 9
<212> TYPE: PRT
<213> ORGANISM: Artificial Sequence
<220> FEATURE:
<223> OTHER INFORMATION: Synthetic

<400> SEQUENCE: 124

Val Leu Asp Ala Leu Asp Ser Ile Lys
1               5

<210> SEQ ID NO 125
<211> LENGTH: 15
<212> TYPE: PRT
<213> ORGANISM: Artificial Sequence
<220> FEATURE:
<223> OTHER INFORMATION: Synthetic

<400> SEQUENCE: 125

Asp Asn Pro Gln Thr His Tyr Tyr Ala Val Ala Val Val Lys Lys
1               5                   10                  15

<210> SEQ ID NO 126
<211> LENGTH: 11
<212> TYPE: PRT
<213> ORGANISM: Artificial Sequence
<220> FEATURE:
<223> OTHER INFORMATION: Synthetic

<400> SEQUENCE: 126

Ile Leu Asn Lys Gln Gln Asp Asp Phe Gly Lys
1               5                   10

<210> SEQ ID NO 127
<211> LENGTH: 8
<212> TYPE: PRT
<213> ORGANISM: Artificial Sequence
<220> FEATURE:
<223> OTHER INFORMATION: Synthetic

<400> SEQUENCE: 127

Leu Leu Ser Ala Ala His Phe Arg
1               5

<210> SEQ ID NO 128
<211> LENGTH: 17
<212> TYPE: PRT
<213> ORGANISM: Artificial Sequence
<220> FEATURE:
<223> OTHER INFORMATION: Synthetic

<400> SEQUENCE: 128

Leu Leu Gly Gly Gly Ser Leu Ser Ser Ser Leu Asp Ala Ala Ala Phe
1               5                   10                  15
Arg
```

```
<210> SEQ ID NO 129
<211> LENGTH: 8
<212> TYPE: PRT
<213> ORGANISM: Artificial Sequence
<220> FEATURE:
<223> OTHER INFORMATION: Synthetic

<400> SEQUENCE: 129

Leu Leu Val Leu Ala His Phe Arg
1               5

<210> SEQ ID NO 130
<211> LENGTH: 7
<212> TYPE: PRT
<213> ORGANISM: Artificial Sequence
<220> FEATURE:
<223> OTHER INFORMATION: Synthetic

<400> SEQUENCE: 130

Leu Gln Asp Thr Leu Val Arg
1               5

<210> SEQ ID NO 131
<211> LENGTH: 9
<212> TYPE: PRT
<213> ORGANISM: Artificial Sequence
<220> FEATURE:
<223> OTHER INFORMATION: Synthetic

<400> SEQUENCE: 131

Asn Leu Ser Val Glu Asp Ala Ala Arg
1               5

<210> SEQ ID NO 132
<211> LENGTH: 12
<212> TYPE: PRT
<213> ORGANISM: Artificial Sequence
<220> FEATURE:
<223> OTHER INFORMATION: Synthetic

<400> SEQUENCE: 132

Gly Ser Asn Phe Gln Leu Asp Gln Leu Gln Gly Arg
1               5                   10

<210> SEQ ID NO 133
<211> LENGTH: 14
<212> TYPE: PRT
<213> ORGANISM: Artificial Sequence
<220> FEATURE:
<223> OTHER INFORMATION: Synthetic

<400> SEQUENCE: 133

Leu Cys Ala Leu Cys Ala Gly Asp Asp Gln Gly Leu Asp Lys
1               5                   10

<210> SEQ ID NO 134
<211> LENGTH: 9
<212> TYPE: PRT
<213> ORGANISM: Artificial Sequence
<220> FEATURE:
<223> OTHER INFORMATION: Synthetic

<400> SEQUENCE: 134

Arg Ala Phe Ala Leu Glu Cys Ile Arg
1               5

<210> SEQ ID NO 135
<211> LENGTH: 13
```

```
<212> TYPE: PRT
<213> ORGANISM: Artificial Sequence
<220> FEATURE:
<223> OTHER INFORMATION: Synthetic

<400> SEQUENCE: 135

Cys Leu Gln Asp Gly Ala Gly Asp Val Ala Phe Val Lys
1               5                   10

<210> SEQ ID NO 136
<211> LENGTH: 11
<212> TYPE: PRT
<213> ORGANISM: Artificial Sequence
<220> FEATURE:
<223> OTHER INFORMATION: Synthetic

<400> SEQUENCE: 136

Glu Lys Tyr Tyr Gly Tyr Thr Gly Ala Phe Arg
1               5                   10

<210> SEQ ID NO 137
<211> LENGTH: 13
<212> TYPE: PRT
<213> ORGANISM: Artificial Sequence
<220> FEATURE:
<223> OTHER INFORMATION: Synthetic

<400> SEQUENCE: 137

Tyr Glu Thr Leu Ile Ser Thr His Glu Ser Thr Ile Arg
1               5                   10

<210> SEQ ID NO 138
<211> LENGTH: 9
<212> TYPE: PRT
<213> ORGANISM: Artificial Sequence
<220> FEATURE:
<223> OTHER INFORMATION: Synthetic

<400> SEQUENCE: 138

Trp Cys Ala Ile Gly His Gln Glu Arg
1               5

<210> SEQ ID NO 139
<211> LENGTH: 12
<212> TYPE: PRT
<213> ORGANISM: Artificial Sequence
<220> FEATURE:
<223> OTHER INFORMATION: Synthetic

<400> SEQUENCE: 139

Leu Arg Pro Val Ala Ala Glu Ile Tyr Gly Thr Lys
1               5                   10

<210> SEQ ID NO 140
<211> LENGTH: 12
<212> TYPE: PRT
<213> ORGANISM: Artificial Sequence
<220> FEATURE:
<223> OTHER INFORMATION: Synthetic

<400> SEQUENCE: 140

Leu Lys Glu Cys Cys Asp Lys Pro Leu Leu Glu Lys
1               5                   10

<210> SEQ ID NO 141
<211> LENGTH: 9
<212> TYPE: PRT
<213> ORGANISM: Artificial Sequence
```

```
<220> FEATURE:
<223> OTHER INFORMATION: Synthetic

<400> SEQUENCE: 141

Leu Asn Ser Leu Thr Val Gly Pro Arg
1               5

<210> SEQ ID NO 142
<211> LENGTH: 21
<212> TYPE: PRT
<213> ORGANISM: Artificial Sequence
<220> FEATURE:
<223> OTHER INFORMATION: Synthetic

<400> SEQUENCE: 142

Gln Glu Pro Glu Arg Asn Glu Cys Phe Leu Ser His Lys Asp Asp Ser
1               5                   10                  15

Pro Asp Leu Pro Lys
            20

<210> SEQ ID NO 143
<211> LENGTH: 8
<212> TYPE: PRT
<213> ORGANISM: Artificial Sequence
<220> FEATURE:
<223> OTHER INFORMATION: Synthetic

<400> SEQUENCE: 143

Ser Met Met Glu Glu Ile Met Lys
1               5

<210> SEQ ID NO 144
<211> LENGTH: 8
<212> TYPE: PRT
<213> ORGANISM: Artificial Sequence
<220> FEATURE:
<223> OTHER INFORMATION: Synthetic

<400> SEQUENCE: 144

Gln Asn Cys Asp Gln Phe Glu Lys
1               5

<210> SEQ ID NO 145
<211> LENGTH: 11
<212> TYPE: PRT
<213> ORGANISM: Artificial Sequence
<220> FEATURE:
<223> OTHER INFORMATION: Synthetic

<400> SEQUENCE: 145

Lys Asp Met Asp Lys Val Glu Thr Phe Leu Arg
1               5                   10

<210> SEQ ID NO 146
<211> LENGTH: 5
<212> TYPE: PRT
<213> ORGANISM: Artificial Sequence
<220> FEATURE:
<223> OTHER INFORMATION: Synthetic

<400> SEQUENCE: 146

Thr Phe Tyr Leu Lys
1               5

<210> SEQ ID NO 147
<211> LENGTH: 14
<212> TYPE: PRT
```

```
<213> ORGANISM: Artificial Sequence
<220> FEATURE:
<223> OTHER INFORMATION: Synthetic

<400> SEQUENCE: 147

Met Glu Asp Glu Ala Glu Ser Leu Glu Asp Leu Gly Phe Lys
1               5                   10

<210> SEQ ID NO 148
<211> LENGTH: 7
<212> TYPE: PRT
<213> ORGANISM: Artificial Sequence
<220> FEATURE:
<223> OTHER INFORMATION: Synthetic

<400> SEQUENCE: 148

Lys Asn Trp Ile Gln Tyr Lys
1               5

<210> SEQ ID NO 149
<211> LENGTH: 12
<212> TYPE: PRT
<213> ORGANISM: Artificial Sequence
<220> FEATURE:
<223> OTHER INFORMATION: Synthetic

<400> SEQUENCE: 149

Thr Ser Asp Ala Asn Ile Asn Trp Asn Asn Leu Lys
1               5                   10

<210> SEQ ID NO 150
<211> LENGTH: 17
<212> TYPE: PRT
<213> ORGANISM: Artificial Sequence
<220> FEATURE:
<223> OTHER INFORMATION: Synthetic

<400> SEQUENCE: 150

Leu Leu Gly Gly Gly Ser Leu Ser Ser Ser Leu His Ala Ala Ala Phe
1               5                   10                  15

Arg

<210> SEQ ID NO 151
<211> LENGTH: 14
<212> TYPE: PRT
<213> ORGANISM: Artificial Sequence
<220> FEATURE:
<223> OTHER INFORMATION: Synthetic

<400> SEQUENCE: 151

Lys Tyr Ala Ala Glu Leu His Leu Val His Trp Asn Thr Lys
1               5                   10

<210> SEQ ID NO 152
<211> LENGTH: 13
<212> TYPE: PRT
<213> ORGANISM: Artificial Sequence
<220> FEATURE:
<223> OTHER INFORMATION: Synthetic

<400> SEQUENCE: 152

Tyr Ala Ala Glu Leu His Leu Val His Trp Asn Thr Lys
1               5                   10

<210> SEQ ID NO 153
<211> LENGTH: 8
<212> TYPE: PRT
```

```
<213> ORGANISM: Artificial Sequence
<220> FEATURE:
<223> OTHER INFORMATION: Synthetic

<400> SEQUENCE: 153

Val Phe Glu His Ile Gly Lys Arg
1               5

<210> SEQ ID NO 154
<211> LENGTH: 10
<212> TYPE: PRT
<213> ORGANISM: Artificial Sequence
<220> FEATURE:
<223> OTHER INFORMATION: Synthetic

<400> SEQUENCE: 154

Leu Leu Glu Ala Cys Thr Phe His Lys Pro
1               5                   10

<210> SEQ ID NO 155
<211> LENGTH: 17
<212> TYPE: PRT
<213> ORGANISM: Artificial Sequence
<220> FEATURE:
<223> OTHER INFORMATION: Synthetic

<400> SEQUENCE: 155

Asp Gly Thr Arg Lys Pro Val Thr Asp Ala Glu Asn Cys His Leu Ala
1               5                   10                  15

Arg

<210> SEQ ID NO 156
<211> LENGTH: 12
<212> TYPE: PRT
<213> ORGANISM: Artificial Sequence
<220> FEATURE:
<223> OTHER INFORMATION: Synthetic

<400> SEQUENCE: 156

Ala Leu Glu His Lys Val Asp Leu Glu Asp Tyr Lys
1               5                   10

<210> SEQ ID NO 157
<211> LENGTH: 15
<212> TYPE: PRT
<213> ORGANISM: Artificial Sequence
<220> FEATURE:
<223> OTHER INFORMATION: Synthetic

<400> SEQUENCE: 157

Thr Ser Asp Ala Asn Ile Asn Trp Asn Leu Lys Asp Lys Lys
1               5                   10                  15

<210> SEQ ID NO 158
<211> LENGTH: 7
<212> TYPE: PRT
<213> ORGANISM: Artificial Sequence
<220> FEATURE:
<223> OTHER INFORMATION: Synthetic

<400> SEQUENCE: 158

Leu Cys Val Leu His Glu Lys
1               5

<210> SEQ ID NO 159
<211> LENGTH: 9
<212> TYPE: PRT
```

```
<213> ORGANISM: Artificial Sequence
<220> FEATURE:
<223> OTHER INFORMATION: Synthetic

<400> SEQUENCE: 159

Gln Thr Ala Leu Val Glu Leu Leu Lys
1               5

<210> SEQ ID NO 160
<211> LENGTH: 12
<212> TYPE: PRT
<213> ORGANISM: Artificial Sequence
<220> FEATURE:
<223> OTHER INFORMATION: Synthetic

<400> SEQUENCE: 160

Phe Leu Gln Glu Ile Tyr Asn Ser Asn Ser Gln Lys
1               5                   10

<210> SEQ ID NO 161
<211> LENGTH: 21
<212> TYPE: PRT
<213> ORGANISM: Artificial Sequence
<220> FEATURE:
<223> OTHER INFORMATION: Synthetic

<400> SEQUENCE: 161

Ala Ala Ala Asn Phe Phe Ser Ala Ser Cys Val Pro Cys Ala Asp Gln
1               5                   10                  15

Ser Ser Phe Pro Lys
            20

<210> SEQ ID NO 162
<211> LENGTH: 7
<212> TYPE: PRT
<213> ORGANISM: Artificial Sequence
<220> FEATURE:
<223> OTHER INFORMATION: Synthetic

<400> SEQUENCE: 162

Cys Leu Ala Ser Ile Ala Lys
1               5

<210> SEQ ID NO 163
<211> LENGTH: 22
<212> TYPE: PRT
<213> ORGANISM: Artificial Sequence
<220> FEATURE:
<223> OTHER INFORMATION: Synthetic

<400> SEQUENCE: 163

Ala Ile Gln Ile Ser Tyr Asn Pro Asp Gln Pro Ser Lys Pro Asn Asn
1               5                   10                  15

Ile Glu Ser Ala Thr Lys
            20

<210> SEQ ID NO 164
<211> LENGTH: 11
<212> TYPE: PRT
<213> ORGANISM: Artificial Sequence
<220> FEATURE:
<223> OTHER INFORMATION: Synthetic

<400> SEQUENCE: 164

Leu Ala Gly Ser Ala Ser Ala Asp Ala Phe Arg
1               5                   10
```

```
<210> SEQ ID NO 165
<211> LENGTH: 11
<212> TYPE: PRT
<213> ORGANISM: Artificial Sequence
<220> FEATURE:
<223> OTHER INFORMATION: Synthetic

<400> SEQUENCE: 165

Leu Ala His Glu Asp Pro Asp Tyr Gly Leu Arg
1               5                   10

<210> SEQ ID NO 166
<211> LENGTH: 7
<212> TYPE: PRT
<213> ORGANISM: Artificial Sequence
<220> FEATURE:
<223> OTHER INFORMATION: Synthetic

<400> SEQUENCE: 166

Val Asp Leu Glu Asp Tyr Lys
1               5

<210> SEQ ID NO 167
<211> LENGTH: 14
<212> TYPE: PRT
<213> ORGANISM: Artificial Sequence
<220> FEATURE:
<223> OTHER INFORMATION: Synthetic

<400> SEQUENCE: 167

Glu Ser Pro Gln Thr His Tyr Tyr Ala Val Ala Val Val Lys
1               5                   10

<210> SEQ ID NO 168
<211> LENGTH: 14
<212> TYPE: PRT
<213> ORGANISM: Artificial Sequence
<220> FEATURE:
<223> OTHER INFORMATION: Synthetic

<400> SEQUENCE: 168

Glu Thr Thr Val Phe Glu Asn Leu Pro Glu Lys Ala Asp Arg
1               5                   10

<210> SEQ ID NO 169
<211> LENGTH: 19
<212> TYPE: PRT
<213> ORGANISM: Artificial Sequence
<220> FEATURE:
<223> OTHER INFORMATION: Synthetic

<400> SEQUENCE: 169

Glu Cys Cys His Gly Asp Leu Leu Glu Cys Ala Asp Asp Arg Ala Asp
1               5                   10                  15

Leu Ala Lys

<210> SEQ ID NO 170
<211> LENGTH: 12
<212> TYPE: PRT
<213> ORGANISM: Artificial Sequence
<220> FEATURE:
<223> OTHER INFORMATION: Synthetic

<400> SEQUENCE: 170

Cys Gly Leu Val Pro Val Leu Ala Glu Asn Tyr Lys
1               5                   10
```

<210> SEQ ID NO 171
<211> LENGTH: 9
<212> TYPE: PRT
<213> ORGANISM: Artificial Sequence
<220> FEATURE:
<223> OTHER INFORMATION: Synthetic

<400> SEQUENCE: 171

Gly Gly Trp Thr Val Ile Gln Asn Arg
1               5

<210> SEQ ID NO 172
<211> LENGTH: 8
<212> TYPE: PRT
<213> ORGANISM: Artificial Sequence
<220> FEATURE:
<223> OTHER INFORMATION: Synthetic

<400> SEQUENCE: 172

Leu Asp Gly Ser Leu Asp Phe Lys
1               5

<210> SEQ ID NO 173
<211> LENGTH: 10
<212> TYPE: PRT
<213> ORGANISM: Artificial Sequence
<220> FEATURE:
<223> OTHER INFORMATION: Synthetic

<400> SEQUENCE: 173

Leu Arg Asp Ser Leu Phe Asn Tyr Gln Lys
1               5                   10

<210> SEQ ID NO 174
<211> LENGTH: 11
<212> TYPE: PRT
<213> ORGANISM: Artificial Sequence
<220> FEATURE:
<223> OTHER INFORMATION: Synthetic

<400> SEQUENCE: 174

Glu Ser Gly Leu Tyr Phe Ile Arg Pro Leu Lys
1               5                   10

<210> SEQ ID NO 175
<211> LENGTH: 16
<212> TYPE: PRT
<213> ORGANISM: Artificial Sequence
<220> FEATURE:
<223> OTHER INFORMATION: Synthetic

<400> SEQUENCE: 175

Arg His Pro Tyr Phe Tyr Ala Pro Glu Leu Leu Tyr Tyr Ala Asn Lys
1               5                   10                  15

<210> SEQ ID NO 176
<211> LENGTH: 15
<212> TYPE: PRT
<213> ORGANISM: Artificial Sequence
<220> FEATURE:
<223> OTHER INFORMATION: Synthetic

<400> SEQUENCE: 176

Ile Gln Ala Leu Leu Asp Lys Tyr Asn Glu Glu Lys Pro Lys Asn
1               5                   10                  15

<210> SEQ ID NO 177

```
<211> LENGTH: 9
<212> TYPE: PRT
<213> ORGANISM: Artificial Sequence
<220> FEATURE:
<223> OTHER INFORMATION: Synthetic

<400> SEQUENCE: 177

Cys Cys Thr Glu Ser Leu Val Asn Arg
1               5

<210> SEQ ID NO 178
<211> LENGTH: 7
<212> TYPE: PRT
<213> ORGANISM: Artificial Sequence
<220> FEATURE:
<223> OTHER INFORMATION: Synthetic

<400> SEQUENCE: 178

Ser Asn Leu Gln Leu Leu Arg
1               5

<210> SEQ ID NO 179
<211> LENGTH: 13
<212> TYPE: PRT
<213> ORGANISM: Artificial Sequence
<220> FEATURE:
<223> OTHER INFORMATION: Synthetic

<400> SEQUENCE: 179

Asn Leu Leu Phe Asn Asp Asn Thr Glu Cys Leu Ala Lys
1               5                   10

<210> SEQ ID NO 180
<211> LENGTH: 14
<212> TYPE: PRT
<213> ORGANISM: Artificial Sequence
<220> FEATURE:
<223> OTHER INFORMATION: Synthetic

<400> SEQUENCE: 180

Asn Thr Pro Glu Lys Gly Tyr Leu Ala Val Ala Val Val Lys
1               5                   10

<210> SEQ ID NO 181
<211> LENGTH: 7
<212> TYPE: PRT
<213> ORGANISM: Artificial Sequence
<220> FEATURE:
<223> OTHER INFORMATION: Synthetic

<400> SEQUENCE: 181

Leu Val Thr Asp Leu Thr Lys
1               5

<210> SEQ ID NO 182
<211> LENGTH: 10
<212> TYPE: PRT
<213> ORGANISM: Artificial Sequence
<220> FEATURE:
<223> OTHER INFORMATION: Synthetic

<400> SEQUENCE: 182

Asp Thr Asp Phe Lys Leu Asn Glu Leu Arg
1               5                   10

<210> SEQ ID NO 183
<211> LENGTH: 10
<212> TYPE: PRT
```

```
<213> ORGANISM: Artificial Sequence
<220> FEATURE:
<223> OTHER INFORMATION: Synthetic

<400> SEQUENCE: 183

Thr Ser Thr Ala Asp Tyr Ala Ser Phe Lys
1               5                   10

<210> SEQ ID NO 184
<211> LENGTH: 7
<212> TYPE: PRT
<213> ORGANISM: Artificial Sequence
<220> FEATURE:
<223> OTHER INFORMATION: Synthetic

<400> SEQUENCE: 184

Ile Gln Ala Leu Leu Asp Lys
1               5

<210> SEQ ID NO 185
<211> LENGTH: 8
<212> TYPE: PRT
<213> ORGANISM: Artificial Sequence
<220> FEATURE:
<223> OTHER INFORMATION: Synthetic

<400> SEQUENCE: 185

Leu Leu Ser Ala Ala Asp Phe Arg
1               5

<210> SEQ ID NO 186
<211> LENGTH: 9
<212> TYPE: PRT
<213> ORGANISM: Artificial Sequence
<220> FEATURE:
<223> OTHER INFORMATION: Synthetic

<400> SEQUENCE: 186

Leu Phe Ala Tyr Pro Asp Thr His Arg
1               5

<210> SEQ ID NO 187
<211> LENGTH: 6
<212> TYPE: PRT
<213> ORGANISM: Artificial Sequence
<220> FEATURE:
<223> OTHER INFORMATION: Synthetic

<400> SEQUENCE: 187

Glu Asp Leu Ile Trp Lys
1               5

<210> SEQ ID NO 188
<211> LENGTH: 7
<212> TYPE: PRT
<213> ORGANISM: Artificial Sequence
<220> FEATURE:
<223> OTHER INFORMATION: Synthetic

<400> SEQUENCE: 188

Val Phe Glu His Ile Gly Lys
1               5

<210> SEQ ID NO 189
<211> LENGTH: 12
<212> TYPE: PRT
<213> ORGANISM: Artificial Sequence
<220> FEATURE:
```

```
<223> OTHER INFORMATION: Synthetic

<400> SEQUENCE: 189

Gln Val Leu Leu His Gln Gln Ala Leu Phe Gly Lys
1               5                   10

<210> SEQ ID NO 190
<211> LENGTH: 20
<212> TYPE: PRT
<213> ORGANISM: Artificial Sequence
<220> FEATURE:
<223> OTHER INFORMATION: Synthetic

<400> SEQUENCE: 190

Glu Gly Phe Gly His Leu Ser Pro Thr Gly Asn Thr Glu Phe Trp Leu
1               5                   10                  15

Gly Asn Glu Lys
            20

<210> SEQ ID NO 191
<211> LENGTH: 8
<212> TYPE: PRT
<213> ORGANISM: Artificial Sequence
<220> FEATURE:
<223> OTHER INFORMATION: Synthetic

<400> SEQUENCE: 191

Asp Ala Gln Leu Phe Ile Gln Lys
1               5

<210> SEQ ID NO 192
<211> LENGTH: 20
<212> TYPE: PRT
<213> ORGANISM: Artificial Sequence
<220> FEATURE:
<223> OTHER INFORMATION: Synthetic

<400> SEQUENCE: 192

Gln Asn Gln Val Gln Asp Asn Glu Asn Val Val Asn Glu Tyr Ser Ser
1               5                   10                  15

His Leu Glu Lys
            20

<210> SEQ ID NO 193
<211> LENGTH: 12
<212> TYPE: PRT
<213> ORGANISM: Artificial Sequence
<220> FEATURE:
<223> OTHER INFORMATION: Synthetic

<400> SEQUENCE: 193

Leu Leu Ile Glu Met Glu Asp Trp Lys Gly Asp Lys
1               5                   10

<210> SEQ ID NO 194
<211> LENGTH: 11
<212> TYPE: PRT
<213> ORGANISM: Artificial Sequence
<220> FEATURE:
<223> OTHER INFORMATION: Synthetic

<400> SEQUENCE: 194

Ala Asn Glu Gly Leu Thr Trp Asn Ser Leu Lys
1               5                   10

<210> SEQ ID NO 195
```

```
<211> LENGTH: 12
<212> TYPE: PRT
<213> ORGANISM: Artificial Sequence
<220> FEATURE:
<223> OTHER INFORMATION: Synthetic

<400> SEQUENCE: 195

Val Val Trp Cys Ala Val Gly Pro Glu Glu Gln Lys
1               5                   10

<210> SEQ ID NO 196
<211> LENGTH: 6
<212> TYPE: PRT
<213> ORGANISM: Artificial Sequence
<220> FEATURE:
<223> OTHER INFORMATION: Synthetic

<400> SEQUENCE: 196

Ala Met Thr Asn Leu Arg
1               5

<210> SEQ ID NO 197
<211> LENGTH: 5
<212> TYPE: PRT
<213> ORGANISM: Artificial Sequence
<220> FEATURE:
<223> OTHER INFORMATION: Synthetic

<400> SEQUENCE: 197

Glu Asn Val Leu Arg
1               5

<210> SEQ ID NO 198
<211> LENGTH: 14
<212> TYPE: PRT
<213> ORGANISM: Artificial Sequence
<220> FEATURE:
<223> OTHER INFORMATION: Synthetic

<400> SEQUENCE: 198

Tyr Cys Gly Val Pro Gly Glu Tyr Trp Leu Gly Asn Asp Arg
1               5                   10

<210> SEQ ID NO 199
<211> LENGTH: 7
<212> TYPE: PRT
<213> ORGANISM: Artificial Sequence
<220> FEATURE:
<223> OTHER INFORMATION: Synthetic

<400> SEQUENCE: 199

Ser Ile Leu Glu Asn Leu Arg
1               5

<210> SEQ ID NO 200
<211> LENGTH: 10
<212> TYPE: PRT
<213> ORGANISM: Artificial Sequence
<220> FEATURE:
<223> OTHER INFORMATION: Synthetic

<400> SEQUENCE: 200

Asn Leu Arg Glu Thr Ala Glu Glu Val Lys
1               5                   10

<210> SEQ ID NO 201
<211> LENGTH: 15
<212> TYPE: PRT
```

<213> ORGANISM: Artificial Sequence
<220> FEATURE:
<223> OTHER INFORMATION: Synthetic

<400> SEQUENCE: 201

Met Lys Gly Leu Ile Asp Glu Val Asp Gln Asp Phe Thr Ser Arg
1               5                   10                  15

<210> SEQ ID NO 202
<211> LENGTH: 14
<212> TYPE: PRT
<213> ORGANISM: Artificial Sequence
<220> FEATURE:
<223> OTHER INFORMATION: Synthetic

<400> SEQUENCE: 202

Asp Asn Pro Gln Thr His Tyr Tyr Ala Val Ala Val Val Lys
1               5                   10

<210> SEQ ID NO 203
<211> LENGTH: 6
<212> TYPE: PRT
<213> ORGANISM: Artificial Sequence
<220> FEATURE:
<223> OTHER INFORMATION: Synthetic

<400> SEQUENCE: 203

Ser Ile Glu Asp Leu Arg
1               5

<210> SEQ ID NO 204
<211> LENGTH: 10
<212> TYPE: PRT
<213> ORGANISM: Artificial Sequence
<220> FEATURE:
<223> OTHER INFORMATION: Synthetic

<400> SEQUENCE: 204

His Gln Leu Tyr Ile Asp Glu Thr Val Lys
1               5                   10

<210> SEQ ID NO 205
<211> LENGTH: 8
<212> TYPE: PRT
<213> ORGANISM: Artificial Sequence
<220> FEATURE:
<223> OTHER INFORMATION: Synthetic

<400> SEQUENCE: 205

Asp Asp Ser Pro Asp Leu Pro Lys
1               5

<210> SEQ ID NO 206
<211> LENGTH: 9
<212> TYPE: PRT
<213> ORGANISM: Artificial Sequence
<220> FEATURE:
<223> OTHER INFORMATION: Synthetic

<400> SEQUENCE: 206

Gln Ser Pro Val Asp Ile Asp Thr Lys
1               5

<210> SEQ ID NO 207
<211> LENGTH: 5
<212> TYPE: PRT
<213> ORGANISM: Artificial Sequence
<220> FEATURE:

<223> OTHER INFORMATION: Synthetic

<400> SEQUENCE: 207

Asp Leu Leu Phe Arg
1               5

<210> SEQ ID NO 208
<211> LENGTH: 5
<212> TYPE: PRT
<213> ORGANISM: Artificial Sequence
<220> FEATURE:
<223> OTHER INFORMATION: Synthetic

<400> SEQUENCE: 208

Lys Phe Trp Gly Lys
1               5

<210> SEQ ID NO 209
<211> LENGTH: 15
<212> TYPE: PRT
<213> ORGANISM: Artificial Sequence
<220> FEATURE:
<223> OTHER INFORMATION: Synthetic

<400> SEQUENCE: 209

Glu Thr Gly Trp Pro Phe Cys Ser Asp Glu Asp Trp Asn Thr Lys
1               5                   10                  15

<210> SEQ ID NO 210
<211> LENGTH: 8
<212> TYPE: PRT
<213> ORGANISM: Artificial Sequence
<220> FEATURE:
<223> OTHER INFORMATION: Synthetic

<400> SEQUENCE: 210

Asp Ser Leu Phe Asn Tyr Gln Lys
1               5

<210> SEQ ID NO 211
<211> LENGTH: 14
<212> TYPE: PRT
<213> ORGANISM: Artificial Sequence
<220> FEATURE:
<223> OTHER INFORMATION: Synthetic

<400> SEQUENCE: 211

His Ser Thr Val Phe Asp Asn Leu Pro Asn Pro Glu Asp Arg
1               5                   10

<210> SEQ ID NO 212
<211> LENGTH: 22
<212> TYPE: PRT
<213> ORGANISM: Artificial Sequence
<220> FEATURE:
<223> OTHER INFORMATION: Synthetic

<400> SEQUENCE: 212

Gly Arg Gln Asn Gln Val Gln Asp Asn Glu Asn Val Val Asn Glu Tyr
1               5                   10                  15

Ser Ser His Leu Glu Lys
            20

<210> SEQ ID NO 213
<211> LENGTH: 13
<212> TYPE: PRT
<213> ORGANISM: Artificial Sequence

```
<220> FEATURE:
<223> OTHER INFORMATION: Synthetic

<400> SEQUENCE: 213

Lys Gly Ser Asn Phe Gln Leu Asp Gln Leu Gln Gly Arg
1               5                   10

<210> SEQ ID NO 214
<211> LENGTH: 7
<212> TYPE: PRT
<213> ORGANISM: Artificial Sequence
<220> FEATURE:
<223> OTHER INFORMATION: Synthetic

<400> SEQUENCE: 214

Asp Gln Leu Val Asp Met Lys
1               5

<210> SEQ ID NO 215
<211> LENGTH: 18
<212> TYPE: PRT
<213> ORGANISM: Artificial Sequence
<220> FEATURE:
<223> OTHER INFORMATION: Synthetic

<400> SEQUENCE: 215

Asp Gln Thr Val Ile Gln Asn Thr Asp Gly Asn Asn Asn Glu Ala Trp
1               5                   10                  15

Ala Lys

<210> SEQ ID NO 216
<211> LENGTH: 13
<212> TYPE: PRT
<213> ORGANISM: Artificial Sequence
<220> FEATURE:
<223> OTHER INFORMATION: Synthetic

<400> SEQUENCE: 216

Ala Val Leu Lys Asp Gly Pro Leu Thr Gly Thr Tyr Arg
1               5                   10

<210> SEQ ID NO 217
<211> LENGTH: 12
<212> TYPE: PRT
<213> ORGANISM: Artificial Sequence
<220> FEATURE:
<223> OTHER INFORMATION: Synthetic

<400> SEQUENCE: 217

Asp Leu Glu Glu Gly Ile Gln Thr Leu Met Gly Arg
1               5                   10

<210> SEQ ID NO 218
<211> LENGTH: 6
<212> TYPE: PRT
<213> ORGANISM: Artificial Sequence
<220> FEATURE:
<223> OTHER INFORMATION: Synthetic

<400> SEQUENCE: 218

Ala Trp Ser Val Ala Arg
1               5

<210> SEQ ID NO 219
<211> LENGTH: 21
<212> TYPE: PRT
<213> ORGANISM: Artificial Sequence
```

```
<220> FEATURE:
<223> OTHER INFORMATION: Synthetic

<400> SEQUENCE: 219

Phe Tyr Thr Glu Asp Gly Asn Trp Asp Leu Val Gly Asn Asn Thr Pro
1               5                   10                  15

Ile Phe Phe Ile Arg
            20

<210> SEQ ID NO 220
<211> LENGTH: 16
<212> TYPE: PRT
<213> ORGANISM: Artificial Sequence
<220> FEATURE:
<223> OTHER INFORMATION: Synthetic

<400> SEQUENCE: 220

Gly Ala Gly Ala Phe Gly Tyr Phe Glu Val Thr His Asp Ile Thr Arg
1               5                   10                  15

<210> SEQ ID NO 221
<211> LENGTH: 14
<212> TYPE: PRT
<213> ORGANISM: Artificial Sequence
<220> FEATURE:
<223> OTHER INFORMATION: Synthetic

<400> SEQUENCE: 221

Tyr Asn Gly Val Phe Gln Glu Cys Cys Gln Ala Glu Asp Lys
1               5                   10

<210> SEQ ID NO 222
<211> LENGTH: 7
<212> TYPE: PRT
<213> ORGANISM: Artificial Sequence
<220> FEATURE:
<223> OTHER INFORMATION: Synthetic

<400> SEQUENCE: 222

Gly Ala Cys Leu Leu Pro Lys
1               5

<210> SEQ ID NO 223
<211> LENGTH: 15
<212> TYPE: PRT
<213> ORGANISM: Artificial Sequence
<220> FEATURE:
<223> OTHER INFORMATION: Synthetic

<400> SEQUENCE: 223

Asp Asp Pro His Ala Cys Tyr Ser Thr Val Phe Asp Lys Leu Lys
1               5                   10                  15

<210> SEQ ID NO 224
<211> LENGTH: 18
<212> TYPE: PRT
<213> ORGANISM: Artificial Sequence
<220> FEATURE:
<223> OTHER INFORMATION: Synthetic

<400> SEQUENCE: 224

Gly Glu Ala Asp Ala Leu Asn Leu Asp Gly Gly Tyr Ile Tyr Thr Ala
1               5                   10                  15

Gly Lys

<210> SEQ ID NO 225
```

```
<211> LENGTH: 9
<212> TYPE: PRT
<213> ORGANISM: Artificial Sequence
<220> FEATURE:
<223> OTHER INFORMATION: Synthetic

<400> SEQUENCE: 225

Asp Gly Pro Leu Thr Gly Thr Tyr Arg
1               5

<210> SEQ ID NO 226
<211> LENGTH: 5
<212> TYPE: PRT
<213> ORGANISM: Artificial Sequence
<220> FEATURE:
<223> OTHER INFORMATION: Synthetic

<400> SEQUENCE: 226

Asp Leu Leu Phe Lys
1               5

<210> SEQ ID NO 227
<211> LENGTH: 11
<212> TYPE: PRT
<213> ORGANISM: Artificial Sequence
<220> FEATURE:
<223> OTHER INFORMATION: Synthetic

<400> SEQUENCE: 227

Trp Cys Thr Ile Ser Thr His Glu Ala Asn Lys
1               5                   10

<210> SEQ ID NO 228
<211> LENGTH: 17
<212> TYPE: PRT
<213> ORGANISM: Artificial Sequence
<220> FEATURE:
<223> OTHER INFORMATION: Synthetic

<400> SEQUENCE: 228

Cys Ala Cys Ser Asn His Glu Pro Tyr Phe Gly Tyr Ser Gly Ala Phe
1               5                   10                  15

Lys

<210> SEQ ID NO 229
<211> LENGTH: 24
<212> TYPE: PRT
<213> ORGANISM: Artificial Sequence
<220> FEATURE:
<223> OTHER INFORMATION: Synthetic

<400> SEQUENCE: 229

Lys Pro Pro Asp Ala Asp Gly Cys Leu His Ala Asp Pro Asp Leu Gly
1               5                   10                  15

Val Leu Cys Pro Thr Gly Cys Lys
            20

<210> SEQ ID NO 230
<211> LENGTH: 16
<212> TYPE: PRT
<213> ORGANISM: Artificial Sequence
<220> FEATURE:
<223> OTHER INFORMATION: Synthetic

<400> SEQUENCE: 230

Val Thr Ala Leu Tyr Glu Gly Phe Thr Val Gln Asn Glu Ala Asn Lys
1               5                   10                  15
```

```
<210> SEQ ID NO 231
<211> LENGTH: 10
<212> TYPE: PRT
<213> ORGANISM: Artificial Sequence
<220> FEATURE:
<223> OTHER INFORMATION: Synthetic

<400> SEQUENCE: 231

Val Asp Ser Ala Leu Tyr Leu Gly Ser Arg
1               5                   10

<210> SEQ ID NO 232
<211> LENGTH: 6
<212> TYPE: PRT
<213> ORGANISM: Artificial Sequence
<220> FEATURE:
<223> OTHER INFORMATION: Synthetic

<400> SEQUENCE: 232

Ile Asn Leu Leu Gln Lys
1               5

<210> SEQ ID NO 233
<211> LENGTH: 13
<212> TYPE: PRT
<213> ORGANISM: Artificial Sequence
<220> FEATURE:
<223> OTHER INFORMATION: Synthetic

<400> SEQUENCE: 233

Val Val Trp Cys Ala Val Gly Pro Glu Glu Gln Lys Lys
1               5                   10

<210> SEQ ID NO 234
<211> LENGTH: 15
<212> TYPE: PRT
<213> ORGANISM: Artificial Sequence
<220> FEATURE:
<223> OTHER INFORMATION: Synthetic

<400> SEQUENCE: 234

His Ser Thr Val Phe Asp Asn Leu Pro Asn Pro Glu Asp Arg Lys
1               5                   10                  15

<210> SEQ ID NO 235
<211> LENGTH: 11
<212> TYPE: PRT
<213> ORGANISM: Artificial Sequence
<220> FEATURE:
<223> OTHER INFORMATION: Synthetic

<400> SEQUENCE: 235

His Met Asp Gly Tyr Gly Ser His Thr Phe Lys
1               5                   10

<210> SEQ ID NO 236
<211> LENGTH: 8
<212> TYPE: PRT
<213> ORGANISM: Artificial Sequence
<220> FEATURE:
<223> OTHER INFORMATION: Synthetic

<400> SEQUENCE: 236

Asp Leu Gly Glu Glu His Phe Lys
1               5
```

```
<210> SEQ ID NO 237
<211> LENGTH: 8
<212> TYPE: PRT
<213> ORGANISM: Artificial Sequence
<220> FEATURE:
<223> OTHER INFORMATION: Synthetic

<400> SEQUENCE: 237

Glu Leu Leu Ile Asp Asn Glu Lys
1               5

<210> SEQ ID NO 238
<211> LENGTH: 8
<212> TYPE: PRT
<213> ORGANISM: Artificial Sequence
<220> FEATURE:
<223> OTHER INFORMATION: Synthetic

<400> SEQUENCE: 238

Leu Leu Cys Leu Asp Gly Thr Arg
1               5

<210> SEQ ID NO 239
<211> LENGTH: 17
<212> TYPE: PRT
<213> ORGANISM: Artificial Sequence
<220> FEATURE:
<223> OTHER INFORMATION: Synthetic

<400> SEQUENCE: 239

Glu Glu Gly Ser Val Ser Ser Gly Thr Lys Gln Glu Phe His Thr Gly
1               5                   10                  15

Lys

<210> SEQ ID NO 240
<211> LENGTH: 13
<212> TYPE: PRT
<213> ORGANISM: Artificial Sequence
<220> FEATURE:
<223> OTHER INFORMATION: Synthetic

<400> SEQUENCE: 240

Asp Ala Leu Leu Phe Pro Ser Phe Ile His Ser Gln Lys
1               5                   10

<210> SEQ ID NO 241
<211> LENGTH: 15
<212> TYPE: PRT
<213> ORGANISM: Artificial Sequence
<220> FEATURE:
<223> OTHER INFORMATION: Synthetic

<400> SEQUENCE: 241

Leu Ala Ile Gly Glu Gly Gln Gln His Gln Leu Gly Gly Ala Lys
1               5                   10                  15

<210> SEQ ID NO 242
<211> LENGTH: 12
<212> TYPE: PRT
<213> ORGANISM: Artificial Sequence
<220> FEATURE:
<223> OTHER INFORMATION: Synthetic

<400> SEQUENCE: 242

Ser Leu His Thr Leu Phe Gly Asp Glu Leu Cys Lys
1               5                   10
```

```
<210> SEQ ID NO 243
<211> LENGTH: 9
<212> TYPE: PRT
<213> ORGANISM: Artificial Sequence
<220> FEATURE:
<223> OTHER INFORMATION: Synthetic

<400> SEQUENCE: 243

Asp Phe Pro Ile Ala Asn Gly Glu Arg
1               5

<210> SEQ ID NO 244
<211> LENGTH: 9
<212> TYPE: PRT
<213> ORGANISM: Artificial Sequence
<220> FEATURE:
<223> OTHER INFORMATION: Synthetic

<400> SEQUENCE: 244

Arg Leu Asp Gly Ser Leu Asp Phe Lys
1               5

<210> SEQ ID NO 245
<211> LENGTH: 15
<212> TYPE: PRT
<213> ORGANISM: Artificial Sequence
<220> FEATURE:
<223> OTHER INFORMATION: Synthetic

<400> SEQUENCE: 245

Lys Tyr Cys Gly Val Pro Gly Glu Tyr Trp Leu Gly Asn Asp Arg
1               5                   10                  15

<210> SEQ ID NO 246
<211> LENGTH: 8
<212> TYPE: PRT
<213> ORGANISM: Artificial Sequence
<220> FEATURE:
<223> OTHER INFORMATION: Synthetic

<400> SEQUENCE: 246

Thr Ser His Met Asp Cys Ile Lys
1               5

<210> SEQ ID NO 247
<211> LENGTH: 11
<212> TYPE: PRT
<213> ORGANISM: Artificial Sequence
<220> FEATURE:
<223> OTHER INFORMATION: Synthetic

<400> SEQUENCE: 247

Cys Gly Leu Val Pro Val Leu Ala Glu Asn Arg
1               5                   10

<210> SEQ ID NO 248
<211> LENGTH: 9
<212> TYPE: PRT
<213> ORGANISM: Artificial Sequence
<220> FEATURE:
<223> OTHER INFORMATION: Synthetic

<400> SEQUENCE: 248

Asp Asn Cys Cys Ile Leu Asp Glu Arg
1               5

<210> SEQ ID NO 249
<211> LENGTH: 12
```

```
<212> TYPE: PRT
<213> ORGANISM: Artificial Sequence
<220> FEATURE:
<223> OTHER INFORMATION: Synthetic

<400> SEQUENCE: 249

Lys Asn Tyr Glu Leu Leu Cys Gly Asp Asn Thr Arg
1               5                   10

<210> SEQ ID NO 250
<211> LENGTH: 13
<212> TYPE: PRT
<213> ORGANISM: Artificial Sequence
<220> FEATURE:
<223> OTHER INFORMATION: Synthetic

<400> SEQUENCE: 250

Asp Asp Pro His Ala Cys Tyr Ser Thr Val Phe Asp Lys
1               5                   10

<210> SEQ ID NO 251
<211> LENGTH: 15
<212> TYPE: PRT
<213> ORGANISM: Artificial Sequence
<220> FEATURE:
<223> OTHER INFORMATION: Synthetic

<400> SEQUENCE: 251

Phe Asp Glu Phe Phe Ser Ala Gly Cys Ala Pro Gly Ser Pro Arg
1               5                   10                  15

<210> SEQ ID NO 252
<211> LENGTH: 8
<212> TYPE: PRT
<213> ORGANISM: Artificial Sequence
<220> FEATURE:
<223> OTHER INFORMATION: Synthetic

<400> SEQUENCE: 252

Asp Ser Ala Leu Gly Phe Leu Arg
1               5

<210> SEQ ID NO 253
<211> LENGTH: 14
<212> TYPE: PRT
<213> ORGANISM: Artificial Sequence
<220> FEATURE:
<223> OTHER INFORMATION: Synthetic

<400> SEQUENCE: 253

Gln Gly Phe Gly Asn Ile Ala Thr Asn Ala Glu Gly Lys Lys
1               5                   10

<210> SEQ ID NO 254
<211> LENGTH: 17
<212> TYPE: PRT
<213> ORGANISM: Artificial Sequence
<220> FEATURE:
<223> OTHER INFORMATION: Synthetic

<400> SEQUENCE: 254

Cys Cys Ala Ala Asp Asp Lys Glu Ala Cys Phe Ala Val Glu Gly Pro
1               5                   10                  15

Lys

<210> SEQ ID NO 255
<211> LENGTH: 7
```

```
<212> TYPE: PRT
<213> ORGANISM: Artificial Sequence
<220> FEATURE:
<223> OTHER INFORMATION: Synthetic

<400> SEQUENCE: 255

Ala Pro Val Asp Ala Phe Lys
1               5

<210> SEQ ID NO 256
<211> LENGTH: 11
<212> TYPE: PRT
<213> ORGANISM: Artificial Sequence
<220> FEATURE:
<223> OTHER INFORMATION: Synthetic

<400> SEQUENCE: 256

Asn Tyr Glu Leu Leu Cys Gly Asp Asn Thr Arg
1               5                   10

<210> SEQ ID NO 257
<211> LENGTH: 21
<212> TYPE: PRT
<213> ORGANISM: Artificial Sequence
<220> FEATURE:
<223> OTHER INFORMATION: Synthetic

<400> SEQUENCE: 257

Ala Val Val Gln Asp Pro Ala Leu Lys Pro Leu Ala Leu Val Tyr Gly
1               5                   10                  15

Glu Ala Thr Ser Arg
            20

<210> SEQ ID NO 258
<211> LENGTH: 9
<212> TYPE: PRT
<213> ORGANISM: Artificial Sequence
<220> FEATURE:
<223> OTHER INFORMATION: Synthetic

<400> SEQUENCE: 258

Gly Asn Leu Asp Asp Phe Phe His Arg
1               5

<210> SEQ ID NO 259
<211> LENGTH: 10
<212> TYPE: PRT
<213> ORGANISM: Artificial Sequence
<220> FEATURE:
<223> OTHER INFORMATION: Synthetic

<400> SEQUENCE: 259

Glu Cys Cys Asp Lys Pro Leu Leu Glu Lys
1               5                   10

<210> SEQ ID NO 260
<211> LENGTH: 19
<212> TYPE: PRT
<213> ORGANISM: Artificial Sequence
<220> FEATURE:
<223> OTHER INFORMATION: Synthetic

<400> SEQUENCE: 260

Ala Ala Gln Lys Pro Asp Val Leu Thr Thr Gly Gly Gly Asn Pro Val
1               5                   10                  15

Gly Asp Lys
```

<210> SEQ ID NO 261
<211> LENGTH: 10
<212> TYPE: PRT
<213> ORGANISM: Artificial Sequence
<220> FEATURE:
<223> OTHER INFORMATION: Synthetic

<400> SEQUENCE: 261

Lys Gln Thr Ala Leu Val Glu Leu Leu Lys
1               5                   10

<210> SEQ ID NO 262
<211> LENGTH: 12
<212> TYPE: PRT
<213> ORGANISM: Artificial Sequence
<220> FEATURE:
<223> OTHER INFORMATION: Synthetic

<400> SEQUENCE: 262

Arg His Pro Glu Tyr Ala Val Ser Val Leu Leu Arg
1               5                   10

<210> SEQ ID NO 263
<211> LENGTH: 10
<212> TYPE: PRT
<213> ORGANISM: Artificial Sequence
<220> FEATURE:
<223> OTHER INFORMATION: Synthetic

<400> SEQUENCE: 263

Asn Cys Pro Asp Lys Phe Cys Leu Phe Lys
1               5                   10

<210> SEQ ID NO 264
<211> LENGTH: 11
<212> TYPE: PRT
<213> ORGANISM: Artificial Sequence
<220> FEATURE:
<223> OTHER INFORMATION: Synthetic

<400> SEQUENCE: 264

Ser Val Asp Gly Lys Glu Asp Leu Ile Trp Lys
1               5                   10

<210> SEQ ID NO 265
<211> LENGTH: 12
<212> TYPE: PRT
<213> ORGANISM: Artificial Sequence
<220> FEATURE:
<223> OTHER INFORMATION: Synthetic

<400> SEQUENCE: 265

Lys Ala Asn Glu Gly Leu Thr Trp Asn Ser Leu Lys
1               5                   10

<210> SEQ ID NO 266
<211> LENGTH: 19
<212> TYPE: PRT
<213> ORGANISM: Artificial Sequence
<220> FEATURE:
<223> OTHER INFORMATION: Synthetic

<400> SEQUENCE: 266

Gly Asp Lys Val Thr Ala Leu Tyr Glu Gly Phe Thr Val Gln Asn Glu
1               5                   10                  15

Ala Asn Lys

<210> SEQ ID NO 267
<211> LENGTH: 28
<212> TYPE: PRT
<213> ORGANISM: Artificial Sequence
<220> FEATURE:
<223> OTHER INFORMATION: Synthetic

<400> SEQUENCE: 267

Ala Ala Gln Lys Pro Asp Val Leu Thr Thr Gly Gly Asn Pro Val
1               5                   10                  15

Gly Asp Lys Leu Asn Ser Leu Thr Val Gly Pro Arg
            20                  25

<210> SEQ ID NO 268
<211> LENGTH: 10
<212> TYPE: PRT
<213> ORGANISM: Artificial Sequence
<220> FEATURE:
<223> OTHER INFORMATION: Synthetic

<400> SEQUENCE: 268

Glu Asp Gly Gly Gly Trp Trp Tyr Asn Arg
1               5                   10

<210> SEQ ID NO 269
<211> LENGTH: 14
<212> TYPE: PRT
<213> ORGANISM: Artificial Sequence
<220> FEATURE:
<223> OTHER INFORMATION: Synthetic

<400> SEQUENCE: 269

Glu Cys Cys His Gly Asp Leu Leu Glu Cys Ala Asp Asp Arg
1               5                   10

<210> SEQ ID NO 270
<211> LENGTH: 11
<212> TYPE: PRT
<213> ORGANISM: Artificial Sequence
<220> FEATURE:
<223> OTHER INFORMATION: Synthetic

<400> SEQUENCE: 270

Gly Asp Lys Glu Leu Leu Ile Asp Asn Glu Lys
1               5                   10

<210> SEQ ID NO 271
<211> LENGTH: 13
<212> TYPE: PRT
<213> ORGANISM: Artificial Sequence
<220> FEATURE:
<223> OTHER INFORMATION: Synthetic

<400> SEQUENCE: 271

Ala Asn Glu Gly Leu Thr Trp Asn Ser Leu Lys Asp Lys
1               5                   10

<210> SEQ ID NO 272
<211> LENGTH: 12
<212> TYPE: PRT
<213> ORGANISM: Artificial Sequence
<220> FEATURE:
<223> OTHER INFORMATION: Synthetic

<400> SEQUENCE: 272

Cys Gly Leu Val Pro Val Leu Ala Glu Asn Arg Lys
1               5                   10

```
<210> SEQ ID NO 273
<211> LENGTH: 6
<212> TYPE: PRT
<213> ORGANISM: Artificial Sequence
<220> FEATURE:
<223> OTHER INFORMATION: Synthetic

<400> SEQUENCE: 273

Thr Gly Gln Ile Phe Lys
1               5

<210> SEQ ID NO 274
<211> LENGTH: 9
<212> TYPE: PRT
<213> ORGANISM: Artificial Sequence
<220> FEATURE:
<223> OTHER INFORMATION: Synthetic

<400> SEQUENCE: 274

Gln Asp Gly Ser Val Asp Phe Gly Arg
1               5

<210> SEQ ID NO 275
<211> LENGTH: 15
<212> TYPE: PRT
<213> ORGANISM: Artificial Sequence
<220> FEATURE:
<223> OTHER INFORMATION: Synthetic

<400> SEQUENCE: 275

Glu Ser Lys Pro Pro Asp Ser Ser Lys Asp Glu Cys Met Val Lys
1               5                   10                  15

<210> SEQ ID NO 276
<211> LENGTH: 13
<212> TYPE: PRT
<213> ORGANISM: Artificial Sequence
<220> FEATURE:
<223> OTHER INFORMATION: Synthetic

<400> SEQUENCE: 276

Gln Gly Phe Gly Asn Ile Ala Thr Asn Ala Glu Gly Lys
1               5                   10

<210> SEQ ID NO 277
<211> LENGTH: 9
<212> TYPE: PRT
<213> ORGANISM: Artificial Sequence
<220> FEATURE:
<223> OTHER INFORMATION: Synthetic

<400> SEQUENCE: 277

Ser His Cys Ile Ala Glu Val Glu Lys
1               5

<210> SEQ ID NO 278
<211> LENGTH: 22
<212> TYPE: PRT
<213> ORGANISM: Artificial Sequence
<220> FEATURE:
<223> OTHER INFORMATION: Synthetic

<400> SEQUENCE: 278

Val His Lys Glu Cys Cys His Gly Asp Leu Leu Glu Cys Ala Asp Asp
1               5                   10                  15

Arg Ala Asp Leu Ala Lys
```

-continued

20

<210> SEQ ID NO 279
<211> LENGTH: 14
<212> TYPE: PRT
<213> ORGANISM: Artificial Sequence
<220> FEATURE:
<223> OTHER INFORMATION: Synthetic

<400> SEQUENCE: 279

Asp Ala Leu Leu Phe Pro Ser Phe Ile His Ser Gln Lys Arg
1               5                   10

<210> SEQ ID NO 280
<211> LENGTH: 9
<212> TYPE: PRT
<213> ORGANISM: Artificial Sequence
<220> FEATURE:
<223> OTHER INFORMATION: Synthetic

<400> SEQUENCE: 280

Ala Leu Leu Glu Met Gln Gln Thr Lys
1               5

<210> SEQ ID NO 281
<211> LENGTH: 14
<212> TYPE: PRT
<213> ORGANISM: Artificial Sequence
<220> FEATURE:
<223> OTHER INFORMATION: Synthetic

<400> SEQUENCE: 281

Lys Ala Asn Glu Gly Leu Thr Trp Asn Ser Leu Lys Asp Lys
1               5                   10

<210> SEQ ID NO 282
<211> LENGTH: 12
<212> TYPE: PRT
<213> ORGANISM: Artificial Sequence
<220> FEATURE:
<223> OTHER INFORMATION: Synthetic

<400> SEQUENCE: 282

Asp Ser Ala Asp Gly Phe Leu Lys Ile Pro Ser Lys
1               5                   10

<210> SEQ ID NO 283
<211> LENGTH: 12
<212> TYPE: PRT
<213> ORGANISM: Artificial Sequence
<220> FEATURE:
<223> OTHER INFORMATION: Synthetic

<400> SEQUENCE: 283

Asn Tyr Glu Leu Leu Cys Gly Asp Asn Thr Arg Lys
1               5                   10

<210> SEQ ID NO 284
<211> LENGTH: 13
<212> TYPE: PRT
<213> ORGANISM: Artificial Sequene
<220> FEATURE:
<223> OTHER INFORMATION: Synthetic

<400> SEQUENCE: 284

Met Val Leu Glu Thr Phe Gly Gly Asp Gly His Ala Arg
1               5                   10

```
<210> SEQ ID NO 285
<211> LENGTH: 11
<212> TYPE: PRT
<213> ORGANISM: Artificial Sequence
<220> FEATURE:
<223> OTHER INFORMATION: Synthetic

<400> SEQUENCE: 285

Ala Arg Pro Ala Thr Ala Thr Val Gly Gln Lys
1               5                   10

<210> SEQ ID NO 286
<211> LENGTH: 12
<212> TYPE: PRT
<213> ORGANISM: Artificial Sequence
<220> FEATURE:
<223> OTHER INFORMATION: Synthetic

<400> SEQUENCE: 286

Ser Phe Gln Leu Phe Gly Ser Pro Pro Gly Gln Arg
1               5                   10

<210> SEQ ID NO 287
<211> LENGTH: 21
<212> TYPE: PRT
<213> ORGANISM: Artificial Sequence
<220> FEATURE:
<223> OTHER INFORMATION: Synthetic

<400> SEQUENCE: 287

Ser Glu Asp Gly Ser Asp Cys Gly Asp Ala Asp Phe Asp Trp His His
1               5                   10                  15

Thr Phe Pro Ser Arg
            20

<210> SEQ ID NO 288
<211> LENGTH: 15
<212> TYPE: PRT
<213> ORGANISM: Artificial Sequence
<220> FEATURE:
<223> OTHER INFORMATION: Synthetic

<400> SEQUENCE: 288

Asp Lys Pro Asp Asn Phe Gln Leu Phe Gln Ser Pro His Gly Lys
1               5                   10                  15

<210> SEQ ID NO 289
<211> LENGTH: 19
<212> TYPE: PRT
<213> ORGANISM: Artificial Sequence
<220> FEATURE:
<223> OTHER INFORMATION: Synthetic

<400> SEQUENCE: 289

Glu Asp Gly Ser Asp Pro Pro Ser Gly Asp Phe Leu Thr Glu Gly Gly
1               5                   10                  15

Gly Val Arg

<210> SEQ ID NO 290
<211> LENGTH: 9
<212> TYPE: PRT
<213> ORGANISM: Artificial Sequence
<220> FEATURE:
<223> OTHER INFORMATION: Synthetic

<400> SEQUENCE: 290
```

```
Glu Cys Val Pro Asn Ser Asn Glu Arg
1               5

<210> SEQ ID NO 291
<211> LENGTH: 8
<212> TYPE: PRT
<213> ORGANISM: Artificial Sequence
<220> FEATURE:
<223> OTHER INFORMATION: Synthetic

<400> SEQUENCE: 291

Asp Lys Asp Asp Phe Phe Thr Arg
1               5

<210> SEQ ID NO 292
<211> LENGTH: 12
<212> TYPE: PRT
<213> ORGANISM: Artificial Sequence
<220> FEATURE:
<223> OTHER INFORMATION: Synthetic

<400> SEQUENCE: 292

Gly Glu Gly Glu Asn Gln Cys Ala Cys Ser Ser Arg
1               5                   10

<210> SEQ ID NO 293
<211> LENGTH: 9
<212> TYPE: PRT
<213> ORGANISM: Artificial Sequence
<220> FEATURE:
<223> OTHER INFORMATION: Synthetic

<400> SEQUENCE: 293

Lys Glu Asn Phe Glu Val Leu Cys Lys
1               5

<210> SEQ ID NO 294
<211> LENGTH: 9
<212> TYPE: PRT
<213> ORGANISM: Artificial Sequence
<220> FEATURE:
<223> OTHER INFORMATION: Synthetic

<400> SEQUENCE: 294

Val Thr Gly Glu Asn Asp Lys Tyr Arg
1               5

<210> SEQ ID NO 295
<211> LENGTH: 7
<212> TYPE: PRT
<213> ORGANISM: Artificial Sequence
<220> FEATURE:
<223> OTHER INFORMATION: Synthetic

<400> SEQUENCE: 295

Val Leu Asn Glu Glu Gln Arg
1               5

<210> SEQ ID NO 296
<211> LENGTH: 17
<212> TYPE: PRT
<213> ORGANISM: Artificial Sequence
<220> FEATURE:
<223> OTHER INFORMATION: Synthetic

<400> SEQUENCE: 296

Val His Lys Glu Cys Cys His Gly Asp Leu Leu Glu Cys Ala Asp Asp
1               5                   10                  15
```

```
<210> SEQ ID NO 297
<211> LENGTH: 8
<212> TYPE: PRT
<213> ORGANISM: Artificial Sequence
<220> FEATURE:
<223> OTHER INFORMATION: Synthetic

<400> SEQUENCE: 297

Asp Ser Ala Asp Gly Phe Leu Lys
1               5

<210> SEQ ID NO 298
<211> LENGTH: 19
<212> TYPE: PRT
<213> ORGANISM: Artificial Sequence
<220> FEATURE:
<223> OTHER INFORMATION: Synthetic

<400> SEQUENCE: 298

Thr Gly Leu Ala Pro Glu Phe Ala Ala Leu Gly Glu Ser Gly Ser Ser
1               5                   10                  15

Ser Ser Lys

<210> SEQ ID NO 299
<211> LENGTH: 5
<212> TYPE: PRT
<213> ORGANISM: Artificial Sequence
<220> FEATURE:
<223> OTHER INFORMATION: Synthetic

<400> SEQUENCE: 299

Cys Leu Val Glu Lys
1               5

<210> SEQ ID NO 300
<211> LENGTH: 13
<212> TYPE: PRT
<213> ORGANISM: Artificial Sequence
<220> FEATURE:
<223> OTHER INFORMATION: Synthetic

<400> SEQUENCE: 300

Thr Cys Val Ala Asp Glu Ser His Ala Gly Cys Glu Lys
1               5                   10

<210> SEQ ID NO 301
<211> LENGTH: 13
<212> TYPE: PRT
<213> ORGANISM: Artificial Sequence
<220> FEATURE:
<223> OTHER INFORMATION: Synthetic

<400> SEQUENCE: 301

Gly Thr Gly Lys Glu Cys Val Pro Asn Ser Asn Glu Arg
1               5                   10
```